United States Patent
DeRosa et al.

(10) Patent No.: US 12,016,954 B2
(45) Date of Patent: Jun. 25, 2024

(54) CNS DELIVERY OF mRNA AND USES THEREOF

(71) Applicant: Translate Bio, Inc., Lexington, MA (US)

(72) Inventors: Frank DeRosa, Lexington, MA (US); Michael Heartlein, Lexington, MA (US); Shrirang Karve, Lexington, MA (US)

(73) Assignee: TRANSLATE BIO, INC., Waltham, MA (US)

(*) Notice: Subject to any disclaimer, the term of this patent is extended or adjusted under 35 U.S.C. 154(b) by 612 days.

(21) Appl. No.: 17/002,460

(22) Filed: Aug. 25, 2020

(65) Prior Publication Data

US 2021/0196633 A1    Jul. 1, 2021

Related U.S. Application Data

(62) Division of application No. 15/676,570, filed on Aug. 14, 2017, now Pat. No. 10,780,052, which is a division of application No. 14/521,168, filed on Oct. 22, 2014, now abandoned.

(60) Provisional application No. 62/020,161, filed on Jul. 2, 2014, provisional application No. 61/894,246, filed on Oct. 22, 2013.

(51) Int. Cl.
| | | |
|---|---|---|
| C07H 21/02 | (2006.01) | |
| A61K 9/127 | (2006.01) | |
| A61K 38/17 | (2006.01) | |
| A61K 48/00 | (2006.01) | |
| C12N 15/88 | (2006.01) | |
| A61P 25/00 | (2006.01) | |

(52) U.S. Cl.
CPC ........ *A61K 9/1272* (2013.01); *A61K 38/1709* (2013.01); *A61K 48/0033* (2013.01); *C12N 15/88* (2013.01); *A61K 48/005* (2013.01); *A61P 25/00* (2018.01); *C07H 21/02* (2013.01)

(58) Field of Classification Search
CPC ....... A61K 9/1272; C12N 15/88; C07H 21/02
See application file for complete search history.

(56) References Cited

U.S. PATENT DOCUMENTS

| | | | |
|---|---|---|---|
| 5,705,385 A | 1/1998 | Bally et al. | |
| 5,965,434 A | 10/1999 | Wolff et al. | |
| 5,976,567 A | 11/1999 | Wheeler et al. | |
| 5,981,501 A | 11/1999 | Wheeler et al. | |
| 6,214,804 B1 | 4/2001 | Felgner et al. | |
| 6,534,484 B1 | 3/2003 | Wheeler et al. | |
| 6,815,432 B2 | 11/2004 | Wheeler et al. | |
| 7,422,902 B1 | 9/2008 | Wheeler et al. | |
| 7,745,651 B2 | 6/2010 | Heyes et al. | |
| 7,799,565 B2 | 9/2010 | MacLachlan et al. | |
| 7,803,397 B2 | 9/2010 | Heyes et al. | |
| 7,901,708 B2 | 3/2011 | MacLachlan et al. | |
| 8,101,741 B2 | 1/2012 | MacLachlan et al. | |
| 8,188,263 B2 | 5/2012 | MacLachlan et al. | |
| 8,236,943 B2 | 8/2012 | Lee et al. | |
| 8,329,070 B2 | 12/2012 | MacLachlan et al. | |
| 8,513,403 B2 | 8/2013 | MacLachlan et al. | |
| 8,569,256 B2 | 10/2013 | Heyes et al. | |
| 8,710,200 B2 | 4/2014 | Schrum et al. | |
| 8,822,663 B2 | 8/2014 | Chen et al. | |
| 8,853,377 B2 | 10/2014 | Guild et al. | |
| 8,883,202 B2 | 11/2014 | Manoharan et al. | |
| 8,936,942 B2 | 1/2015 | Heyes et al. | |
| 8,980,864 B2 | 3/2015 | Hoge et al. | |
| 8,999,351 B2 | 4/2015 | Manoharan et al. | |
| 8,999,380 B2 | 4/2015 | Bancel et al. | |
| 8,999,950 B2 | 4/2015 | MacLachlan et al. | |
| 9,018,187 B2 | 4/2015 | Heyes et al. | |
| 9,051,567 B2 | 6/2015 | Fitzgerald et al. | |
| 9,061,059 B2 | 6/2015 | Chakraborty et al. | |
| 9,074,208 B2 | 7/2015 | MacLachlan et al. | |
| 9,089,604 B2 | 7/2015 | Chakraborty et al. | |
| 9,095,552 B2 | 8/2015 | Chakraborty et al. | |
| 9,107,886 B2 | 8/2015 | Chakraborty et al. | |
| 9,114,113 B2 | 8/2015 | Chakraborty et al. | |
| 9,181,319 B2 | 11/2015 | Schrum et al. | |
| 9,186,325 B2 | 11/2015 | Manoharan et al. | |
| 9,186,372 B2 | 11/2015 | de Fougerolles et al. | |
| 9,187,748 B2 | 11/2015 | Geisbert et al. | |
| 9,192,651 B2 | 11/2015 | Chakraborty et al. | |
| 9,220,755 B2 | 12/2015 | Chakraborty et al. | |
| 9,220,792 B2 | 12/2015 | Chakraborty et al. | |
| 9,233,141 B2 | 1/2016 | Chakraborty et al. | |
| 9,254,311 B2 | 2/2016 | Bancel et al. | |
| 9,295,689 B2 | 3/2016 | de Fougerolles et al. | |
| 9,301,993 B2 | 4/2016 | Chakraborty et al. | |

(Continued)

FOREIGN PATENT DOCUMENTS

| | | |
|---|---|---|
| CA | 2 807 552 A1 | 9/2012 |
| EP | 1 519 714 B1 | 10/2010 |

(Continued)

OTHER PUBLICATIONS

Ishida et al., "Interaction of Liposomes with Cell Membrane," Membrane, 2007, vol. 32 No. 1, p. 18-24, Abstract.

(Continued)

*Primary Examiner* — Shin Lin Chen
(74) *Attorney, Agent, or Firm* — LATHROP GPM LLP; James H. Velema, Esq.

(57) ABSTRACT

The present invention provides, among other things, methods and compositions for effective delivery of messenger RNA (mRNA) to the central system (CNS). In particular, the present invention provides methods and compositions for administering intrathecally to a subject in need of delivery a composition comprising an mRNA encoding a protein, encapsulated within a liposome, such that the administering of the composition results in the intracellular delivery of mRNA in neurons in the brain and/or spinal cord. The present invention is particularly useful for the treatment of CNS diseases, disorders or conditions, such as spinal muscular atrophy.

24 Claims, 51 Drawing Sheets
Specification includes a Sequence Listing.

(56) References Cited

U.S. PATENT DOCUMENTS

| | | |
|---|---|---|
| 9,303,079 B2 | 4/2016 | Chakraborty et al. |
| 9,334,328 B2 | 5/2016 | Schrum et al. |
| 9,345,780 B2 | 5/2016 | Manoharan et al. |
| 9,352,042 B2 | 5/2016 | Heyes et al. |
| 9,352,048 B2 | 5/2016 | Manoharan et al. |
| 9,364,435 B2 | 6/2016 | Yaworski et al. |
| 9,370,581 B2 | 6/2016 | Manoharan et al. |
| 9,370,582 B2 | 6/2016 | Manoharan et al. |
| 9,394,234 B2 | 7/2016 | Chen et al. |
| 9,404,127 B2 | 8/2016 | Yaworski et al. |
| 9,428,751 B2 | 8/2016 | MacDonald et al. |
| 9,464,124 B2 | 10/2016 | Bancel et al. |
| 2002/0192651 A1 | 12/2002 | Wheeler et al. |
| 2003/0181410 A1 | 9/2003 | Wheeler et al. |
| 2004/0142025 A1 | 7/2004 | MacLachlan et al. |
| 2006/0008910 A1 | 1/2006 | MacLachlan et al. |
| 2006/0083780 A1 | 4/2006 | Heyes et al. |
| 2007/0135372 A1 | 6/2007 | MacLachlan et al. |
| 2009/0270481 A1 | 10/2009 | MacLachlan et al. |
| 2010/0041152 A1 | 2/2010 | Wheeler et al. |
| 2010/0158869 A1 | 6/2010 | Kaemmerer |
| 2010/0249208 A1 | 9/2010 | Hecker et al. |
| 2011/0244026 A1 | 10/2011 | Guild et al. |
| 2011/0256175 A1 | 10/2011 | Hope et al. |
| 2011/0294226 A1 | 12/2011 | Melki et al. |
| 2011/0311583 A1 | 12/2011 | Manoharan et al. |
| 2012/0065252 A1 | 3/2012 | Schrum et al. |
| 2012/0128760 A1 | 5/2012 | Manoharan et al. |
| 2012/0142756 A1 | 6/2012 | Guild et al. |
| 2012/0202871 A1 | 8/2012 | Heyes et al. |
| 2012/0237975 A1 | 9/2012 | Schrum et al. |
| 2012/0251618 A1 | 10/2012 | Schrum et al. |
| 2012/0328668 A1 | 12/2012 | MacLachlan et al. |
| 2013/0195967 A1 | 8/2013 | Guild et al. |
| 2013/0237594 A1 | 9/2013 | de Fougerolles et al. |
| 2013/0259923 A1 | 10/2013 | Bancel et al. |
| 2013/0259924 A1 | 10/2013 | Bancel et al. |
| 2013/0266640 A1 | 10/2013 | de Fougerolles et al. |
| 2014/0010861 A1 | 1/2014 | Bancel et al. |
| 2014/0044772 A1 | 2/2014 | MacLachlan et al. |
| 2014/0105964 A1 | 4/2014 | Bancel et al. |
| 2014/0105965 A1 | 4/2014 | Bancel et al. |
| 2014/0147432 A1 | 5/2014 | Bancel et al. |
| 2014/0147454 A1 | 5/2014 | Chakraborty et al. |
| 2014/0148502 A1 | 5/2014 | Bancel et al. |
| 2014/0155472 A1 | 6/2014 | Bancel et al. |
| 2014/0155473 A1 | 6/2014 | Bancel et al. |
| 2014/0155474 A1 | 6/2014 | Bancel et al. |
| 2014/0155475 A1 | 6/2014 | Bancel et al. |
| 2014/0171485 A1 | 6/2014 | Bancel et al. |
| 2014/0179756 A1 | 6/2014 | MacLachlan et al. |
| 2014/0179771 A1 | 6/2014 | Bancel et al. |
| 2014/0186432 A1 | 7/2014 | Bancel et al. |
| 2014/0193482 A1 | 7/2014 | Bancel et al. |
| 2014/0194494 A1 | 7/2014 | Bancel et al. |
| 2014/0199371 A1 | 7/2014 | Bancel et al. |
| 2014/0200261 A1 | 7/2014 | Hoge et al. |
| 2014/0200262 A1 | 7/2014 | Bancel et al. |
| 2014/0200263 A1 | 7/2014 | Bancel et al. |
| 2014/0200264 A1 | 7/2014 | Bancel et al. |
| 2014/0206752 A1 | 7/2014 | Afeyan et al. |
| 2014/0206753 A1 | 7/2014 | Guild et al. |
| 2014/0206755 A1 | 7/2014 | Bancel et al. |
| 2014/0206852 A1 | 7/2014 | Hoge et al. |
| 2014/0212434 A1 | 7/2014 | Blaney et al. |
| 2014/0221465 A1 | 8/2014 | Bancel et al. |
| 2014/0243399 A1 | 8/2014 | Schrum et al. |
| 2014/0249208 A1 | 9/2014 | Bancel et al. |
| 2014/0255467 A1 | 9/2014 | Bancel et al. |
| 2014/0255468 A1 | 9/2014 | Bancel et al. |
| 2014/0275227 A1 | 9/2014 | Hoge et al. |
| 2014/0275229 A1 | 9/2014 | Bancel et al. |
| 2014/0294937 A1 | 10/2014 | MacLachlan et al. |
| 2014/0343129 A1 | 11/2014 | de Fougerolles et al. |
| 2015/0005372 A1 | 1/2015 | Hoge et al. |
| 2015/0017211 A1 | 1/2015 | de Fougerolles et al. |
| 2015/0038556 A1 | 2/2015 | Heartlein et al. |
| 2015/0044277 A1 | 2/2015 | Bancel et al. |
| 2015/0050354 A1 | 2/2015 | Bouchon et al. |
| 2015/0051268 A1 | 2/2015 | Bancel et al. |
| 2015/0056253 A1 | 2/2015 | Bancel et al. |
| 2015/0064235 A1 | 3/2015 | Bancel et al. |
| 2015/0064236 A1 | 3/2015 | Bancel et al. |
| 2015/0064242 A1 | 3/2015 | Heyes et al. |
| 2015/0064725 A1 | 3/2015 | Schrum et al. |
| 2015/0086614 A1 | 3/2015 | Bancel et al. |
| 2015/0111248 A1 | 4/2015 | Bancel et al. |
| 2015/0111945 A1 | 4/2015 | Geisbert et al. |
| 2015/0166465 A1 | 6/2015 | Chen et al. |
| 2015/0190515 A1 | 7/2015 | Manoharan et al. |
| 2015/0265708 A1 | 9/2015 | Manoharan et al. |
| 2015/0315541 A1 | 11/2015 | Bancel et al. |
| 2015/0315584 A1 | 11/2015 | MacDonald et al. |
| 2015/0366997 A1 | 12/2015 | Guild et al. |
| 2016/0095924 A1 | 4/2016 | Hope et al. |
| 2016/0114011 A1 | 4/2016 | Bancel et al. |
| 2016/0115477 A1 | 4/2016 | MacLachlan et al. |
| 2016/0115483 A1 | 4/2016 | MacLachlan et al. |
| 2016/0136236 A1 | 5/2016 | Hoge et al. |
| 2016/0151284 A1 | 6/2016 | Heyes et al. |
| 2016/0158385 A1 | 6/2016 | Bancel et al. |
| 2016/0193299 A1 | 7/2016 | de Fougerolles et al. |
| 2016/0194368 A1 | 7/2016 | Hoge et al. |
| 2016/0194625 A1 | 7/2016 | Hoge et al. |
| 2016/0199485 A1 | 7/2016 | Manoharan et al. |
| 2016/0213785 A1 | 7/2016 | Manoharan et al. |
| 2016/0237108 A1 | 8/2016 | Fraley et al. |
| 2016/0237134 A1 | 8/2016 | Hoge et al. |
| 2016/0250354 A1 | 9/2016 | Manoharan et al. |
| 2016/0251681 A1 | 9/2016 | Yaworski et al. |
| 2016/0256567 A1 | 9/2016 | Heyes et al. |
| 2016/0256568 A1 | 9/2016 | Heyes et al. |
| 2016/0264971 A1 | 9/2016 | Geisbert et al. |
| 2016/0274089 A1 | 9/2016 | Ciufolini et al. |
| 2016/0304552 A1 | 10/2016 | Roy et al. |
| 2016/0317647 A1 | 11/2016 | Ciaramella et al. |
| 2016/0317676 A1 | 11/2016 | Hope et al. |

FOREIGN PATENT DOCUMENTS

| | | |
|---|---|---|
| EP | 2 449 106 A0 | 5/2012 |
| EP | 2 338 478 A1 | 6/2013 |
| EP | 2 823 809 A1 | 1/2015 |
| WO | WO1996/10391 | 4/1996 |
| WO | WO2004/011647 A1 | 2/2004 |
| WO | WO2005/026372 | 3/2005 |
| WO | WO2005/026372 A1 | 3/2005 |
| WO | WO2005/115481 A1 | 12/2005 |
| WO | WO2005/121348 A1 | 12/2005 |
| WO | WO2009/127060 A1 | 10/2009 |
| WO | WO2009/142892 A1 | 11/2009 |
| WO | WO2010/042877 A1 | 4/2010 |
| WO | WO2011/068810 A1 | 6/2011 |
| WO | WO2011/141705 A1 | 11/2011 |
| WO | WO2012/019168 A1 | 2/2012 |
| WO | WO2012/135805 A2 | 10/2012 |
| WO | WO2012/170889 | 12/2012 |
| WO | WO2012/170930 A1 | 12/2012 |
| WO | WO2013/039857 A1 | 3/2013 |
| WO | WO2013/039861 A2 | 3/2013 |
| WO | WO2013/063468 | 5/2013 |
| WO | WO2013/090186 A1 | 6/2013 |
| WO | WO2013/101690 A1 | 7/2013 |
| WO | WO2013/126803 A1 | 8/2013 |
| WO | WO2013/130161 A1 | 9/2013 |
| WO | WO2013/149140 A1 | 10/2013 |
| WO | WO2013/149141 A1 | 10/2013 |
| WO | WO2013/151663 A1 | 10/2013 |
| WO | WO2013/151664 A1 | 10/2013 |
| WO | WO2013/151666 A2 | 10/2013 |
| WO | WO2013/151667 A1 | 10/2013 |
| WO | WO2013/151668 A2 | 10/2013 |
| WO | WO2013/151670 A2 | 10/2013 |
| WO | WO2013/151671 A1 | 10/2013 |

(56) References Cited

FOREIGN PATENT DOCUMENTS

| WO | WO2013/151672 A2 | 10/2013 |
| WO | WO2013/151736 A2 | 10/2013 |
| WO | WO2014/089486 A1 | 6/2014 |
| WO | WO2014/113089 A2 | 7/2014 |
| WO | WO2014/144039 A1 | 9/2014 |
| WO | WO2014/144196 A1 | 9/2014 |
| WO | WO2014/144711 A1 | 9/2014 |
| WO | WO2014/144767 A1 | 9/2014 |
| WO | WO2014/152027 A1 | 9/2014 |
| WO | WO2014/152030 A1 | 9/2014 |
| WO | WO2014/152031 A1 | 9/2014 |
| WO | WO2014/152211 A1 | 9/2014 |
| WO | WO2014/152540 A1 | 9/2014 |
| WO | WO2014/158795 A1 | 10/2014 |
| WO | WO2014/159813 A1 | 10/2014 |
| WO | WO2015/006747 A2 | 1/2015 |
| WO | WO2015/011633 A1 | 4/2015 |
| WO | WO2015/048744 | 4/2015 |
| WO | WO2015/051169 | 4/2015 |
| WO | WO2015/051173 | 4/2015 |
| WO | WO2015/085318 | 6/2015 |
| WO | WO2015/089511 | 6/2015 |
| WO | WO2015/058069 | 4/2016 |
| WO | WO2016/054421 | 4/2016 |
| WO | WO2016/071857 A1 | 5/2016 |
| WO | WO2016/077123 A1 | 5/2016 |
| WO | WO2016/077125 A1 | 5/2016 |
| WO | WO2016/100812 A1 | 6/2016 |
| WO | WO2016/118724 | 7/2016 |
| WO | WO2016/118725 | 7/2016 |
| WO | WO2016/154127 | 9/2016 |
| WO | WO2016/164762 | 10/2016 |
| WO | WO2019/207060 A1 | 10/2019 |

OTHER PUBLICATIONS

Office Action for Canadian Patent Application No. 2,928,040, 3 pages, dated Oct. 18, 2022.
Alton et al., "A randomised, double-blind, placebo-controlled trial of repeated nebulisation of non-viral cystic fibrosis transmembrane conductance regulator (CFTR) gene therapy in patients with cystic fibrosis", National Institute for Health Research, vol. 3, Issue 5, (2016).
Anderson, Dua M. et al., Stability of mRNA/Cationic Lipid Lipoplexes in Human and Rat Cerebrospinal Fluid: Methods and Evidence for Nonviral mRNA Gene Delivery to the Central Nervous System, Human Gene Therapy, 14:191-202, Feb. 10, 2003 (Feb. 10, 2003), pp. 191-202.
Benkhelifa-Ziyyat et al., "Intramuscular scAAV9-SMN Injection Mediates Widespread Gene Delivery to the Spinal Cord and Decreases Disease Severity in SMA Mice", Molecular Therapy, 21(2): 282-290 (2013).
Ewert et al., "Cationic lipid-DNA complexes for non-viral gene therapy: relating supramolecular structures to cellular pathways", Expert Opinion on Biological Therapy, 5(1): 33-53 (2005).
Huang et al., "Thiocholesterol-Based Lipids for Ordered Assembly of Bioresponsive Gene Carriers", Molecular Therapy, 11(3): 409-417 (2005).
International Search Report and Written Opinion for PCT/US2014/061786 dated Feb. 6, 2015.
Kariko, K., et al., In vivo protein expression from mRNA delivered into adult rat brain, Journal Of Neuroscience Methods, 105 Jan. 2001 (Jan. 30, 2001), pp. 77-86.
Karthigasan, J., et al., Protein and Lipid Composition of Radial Component-Enriched CNS Myelin. Journal of Neurochemistry Journal of Neurochemistry, 1994, 62:1203-1213.
Kumar et al., Asian Journal of Pharmaceutical Technology & Innovation, 2015, vol. 3, No. 12, p. 57-68.
Liu, Y. et al., Designer Lipids Advance Systemic siRNA Delivery, Molecular Therapy, vol. 18 No. 4, Apr. 2010, pp. 669-670.
Mukai et al., "2-5A Antisense Telomerase RNA Therapy for Intracranial Malignant Gliomas", Cancer Research, 60: 4461-4467 (2000).
Mulcahy et al., Human Gene Therapy, 2014, vol. 25, p. 575-586.
Syvennerholm, L., et al., Membrane lipids of human peripheral nerve and spinal cord. Biochimica et Biophysica Acta, 1992, 1128: 1-7.
Webb, M. S., et al., Sphingomyel In-Cholesterol Liposomes Significantly Enhance the Pharmacokinetic and Therapeutic Properties of Vincristine in Murine and Human Tumour Models, British Journal of Cancer, vol. 72, No. 4, Jan. 1, 1995 (Jan. 1, 1995), pp. 896-904.
Williams, DJ, et al., A Simple, Highly Efficient Method for Heterologous Expression in Mammalian Primary Neurons Using Cationic Lipid-mediated mRNA Transfection, Frontiers In Neuroscience, vol. 4, Article 181, Nov. 2010 (Nov. 4, 2010), p. 1-20.
Zou S., et al., Lipid-Mediated Delivery of RNA Is More Efficient Than Delivery of DNA in Non-Dividing Cells, International Journal of Pharmaceutics, vol. 389, No. 1-2, Apr. 15, 2010 (Apr. 15, 2010), pp. 232-243.
Office Action for Canadian Patent Application No. 2,928,040, 4 pages, dated Dec. 15, 2020.
Office Action for Canadian Patent Application No. 2,928,040, 4 pages, dated Nov. 25, 2021.
Office Action for European Patent Application No. 14792712.3, 3 pages, dated Nov. 18, 2020.

Detection of hSMN-1 mRNA in Spinal Tissue

Detection of hSMN-1 mRNA in Spinal Tissue

Detection of hSMN-1 mRNA in Spinal Tissue

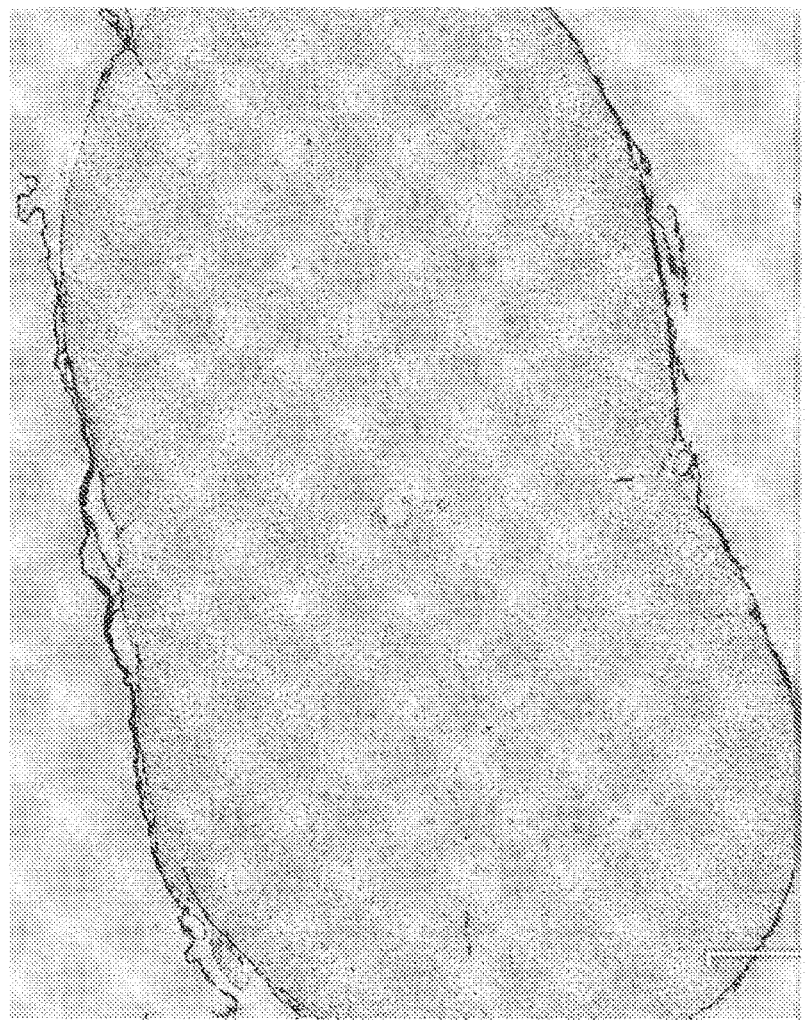
Figure 8A — Detection of hSMN-1 mRNA in Spinal Tissue

Detection of hSMN-1 mRNA in Spinal Tissue

Detection of hSMN-1 mRNA in Spinal Tissue

Detection of hSMN-1 mRNA in Spinal Tissue

Detection of hSMN-1 mRNA in Spinal Tissue

Detection of hSMN-1 mRNA in Spinal Tissue

Detection of hSMN-1 mRNA in Spinal Tissue

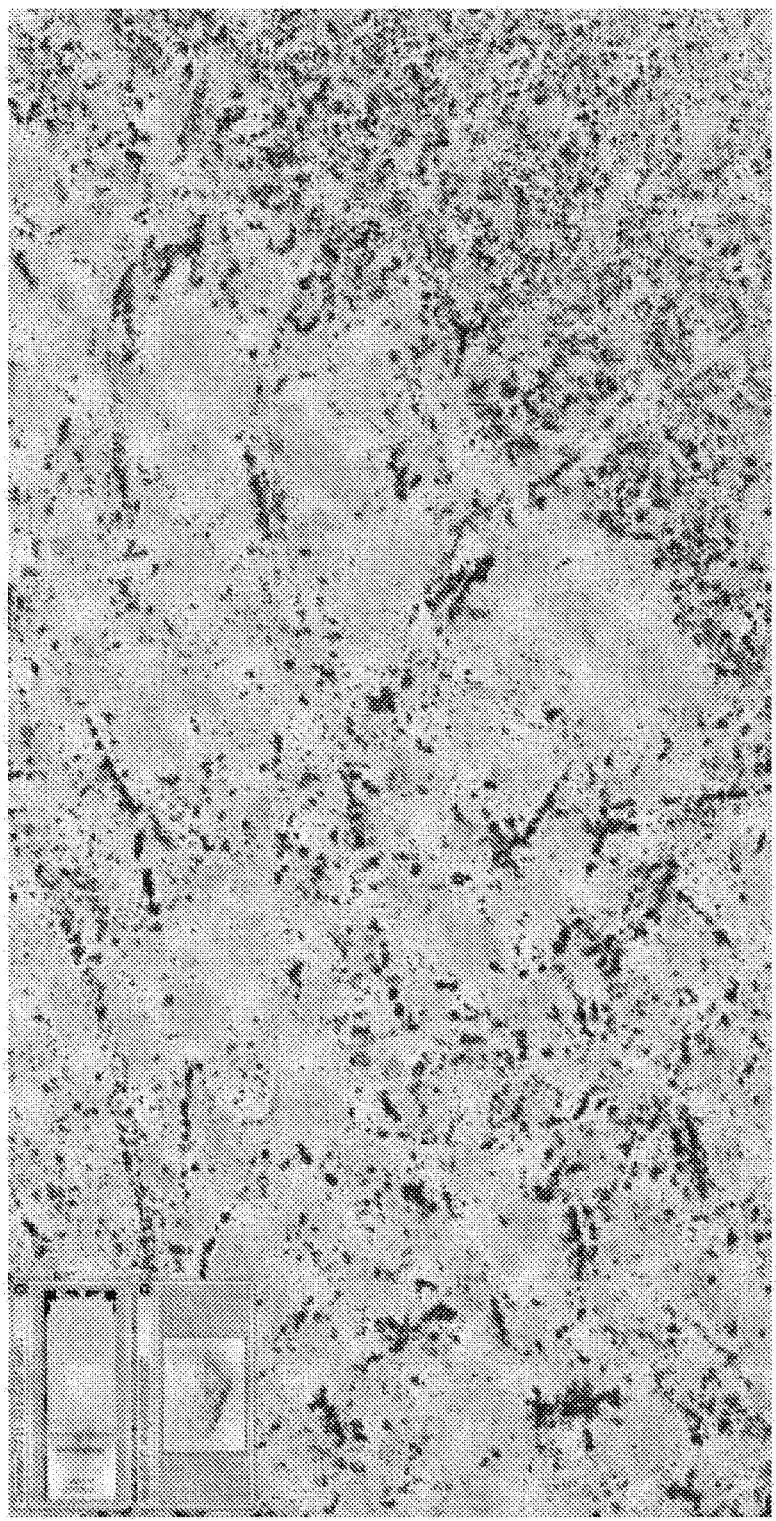
Figure 13A — Detection of hSMN-1 mRNA in Spinal Tissue

Detection of hSMN-1 mRNA in Spinal Tissue

Figure 18 — Staining for UbC in Spinal Tissue (Positive Control)

Figure 19: Detection of hSMN-1 mRNA in Spinal Tissue

Detection of hSMN-1 Protein in Rat Spinal Tissue

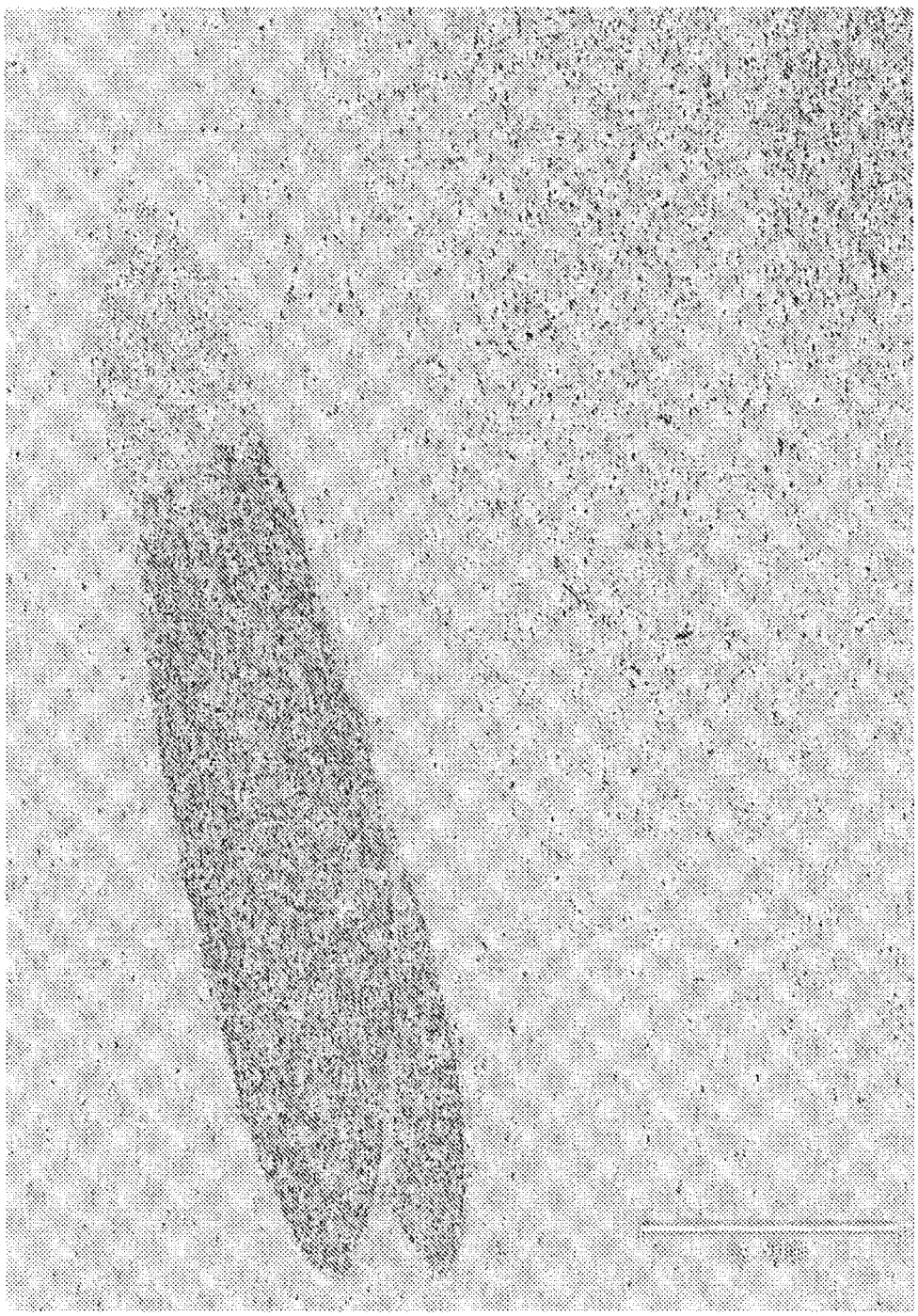
Figure 23C — Magnification of Section 2

CNS DELIVERY OF mRNA AND USES THEREOF

CROSS REFERENCE TO RELATED APPLICATIONS

This application is a division of U.S. application Ser. No. 15/676,570, filed Aug. 14, 2017, which is a division of U.S. application Ser. No. 14/521,168, now abandoned, filed on Oct. 22, 2014, which claims priority to U.S. Provisional Application Ser. No. 62/020,161, filed Jul. 2, 2014 and U.S. Provisional Application No. 61/894,246, filed Oct. 22, 2013, the disclosures of which are hereby incorporated by reference.

INCORPORATION BY REFERENCE OF SEQUENCE LISTING

The contents of the file named "MRT-1123US3_SequenceListing.txt", which was created on Aug. 24, 2020 and is 19,617 bytes in size, are hereby incorporated by reference in their entirety.

BACKGROUND

Effective therapies are still needed for the treatment of CNS diseases, such as those diseases directly or indirectly resulting from the loss, aberrant expression or dysregulation of a neuronal cellular protein. Several hurdles exist in implementing an effective treatment strategy for CNS diseases, mainly due to the isolation and sequestration of the CNS tissues by the impermeable blood brain barrier (BBB).

Fox example, spinal muscular atrophy represents a CNS disease resulting from a protein deficiency. Typically, a healthy individual has functional copies of each of the survival of motor neuron (SMN) genes (SMN-1 and SMN-2), which are nearly identical in sequence. Patients diagnosed with spinal muscular atrophy typically fail to express a full-length SMN-1 protein, relying solely on low level expression of full length SMN-2, which not sufficient to prevent motor neuron death in the brain.

In recent years, messenger RNA (mRNA) therapy has become an increasingly important option for treatment of various diseases, in particular, for those associated with deficiency of one or more proteins. While promising for non-neuronal diseases, those skilled in the art have been dissuaded from implementing such an approach for treating a CNS disease, due to the inability of liposomes to permeate the BBB, as well as the unique and complex membrane composition of neuronal cells which imposes unique challenges for delivering mRNA inside neuronal cells (Svennerhol et. al., Biochimica et Biophysica Acta, 1992, 1128:1-7; and Karthigasan et. al., Journal of Neurochemistry, 1994, 62:1203-1213).

SUMMARY

The present invention provides, among other things, improved methods and compositions for efficient delivery of mRNA, encoding a therapeutic protein, to neurons and other cell types of the CNS. The invention is based, in part, on the surprising discovery that mRNA loaded lipid or polymer based nanoparticles can be administered directly into the CNS space (e.g., via intrathecal administration) and effectively penetrate neuronal cell membrane, resulting in intracellular delivery of mRNA in neurons in the brain and/or spinal cord. Prior to the present invention, it was reported that the neuronal cell membranes are characterized with unique and complex lipid compositions, different than those of the non-neuronal cells (Svennerhol et. al., Biochimica et Biophysica Acta, 1992, 1128:1-7; and Karthigasan et. al., Journal of Neurochemistry, 1994, 62:1203-1213). Therefore, it was thought that neuronal cell membranes are hard to penetrate. Even those liposomes effective in delivering nucleic acids to non-neuronal cells were not expected to be effective in penetrating neuronal cell membranes. It was indeed surprising that the lipid or polymer based nanoparticles described herein can effectively deliver mRNA into neurons, even those located deep within the center of the brain and the spinal column and those hard to treat motor neurons. Thus, the present invention provides an improved and effective approach for the CNS delivery of mRNA and promises an effective mRNA therapy for treating various CNS diseases.

Thus, in one aspect, the invention provides methods of delivering an mRNA to the central nervous system (CNS). In some embodiments, an inventive method according to the present invention includes administering intrathecally to a subject in need of delivery a composition comprising an mRNA encoding a protein, encapsulated within a liposome such that the administering of the composition results in the intracellular delivery of mRNA in neurons in the brain and/or spinal cord; wherein the liposome comprises cationic or non-cationic lipid, cholesterol-based lipid and PEG-modified lipid.

In some embodiments, the mRNA is delivered to neurons located within the brain. In some embodiments, the mRNA is delivered to neurons located within the spinal cord. In some embodiments, the mRNA is delivered to motor neurons. In some embodiments, the mRNA is delivered to upper motor neurons and/or lower motor neurons. In some embodiments, the motor neurons are located within the anterior horn and/or dorsal root ganglia of the spinal cord.

In some embodiments, a suitable liposome comprises one or more cationic lipids, one or more neutral lipids, one or more cholesterol-based lipids and one or more PEG-modified lipids.

In some embodiments, suitable cationic lipids are selected from the group consisting of C12-200, MC3, DLinDMA, DLinkC2DMA, cKK-E12, ICE (Imidazol-based), HGT5000, HGT5001, DODAC, DDAB, DMRIE, DOSPA, DOGS, DODAP, DODMA and DMDMA, DODAC, DLenDMA, DMRIE, CLinDMA, CpLinDMA, DMOBA, DOcabDAP, DLinDAP, DLincarbDAP, DLinCDAP, KLin-K-DMA, DLin-K-XTC2-DMA, HGT4003. In some specific embodiments, the one or more cationic lipid comprises C12-200. In some specific embodiments, the cationic lipid comprises DLinK22DMA.

In certain embodiments, a cationic lipid suitable for the present invention has a structure of formula I-c1-a:

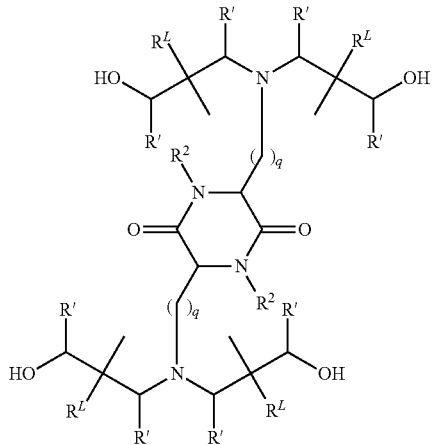

or a pharmaceutically acceptable salt thereof, wherein:
each $R^2$ independently is hydrogen or $C_{1-3}$ alkyl;
each q independently is 2 to 6;
each R' independently is hydrogen or $C_{1-3}$ alkyl;
and each $R^L$ independently is $C_{8-12}$ alkyl.

In certain embodiments, a suitable cationic lipid is cKK-E12:

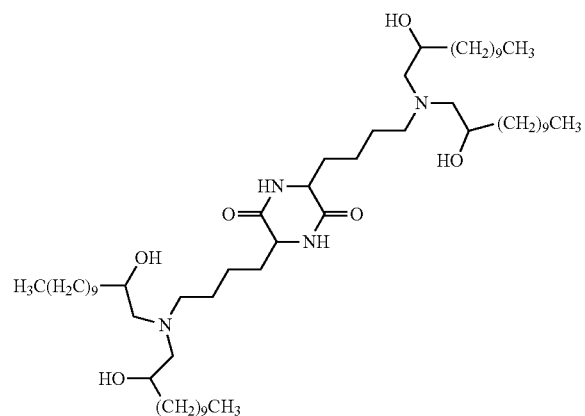

In some embodiments, suitable non-cationic lipids are selected from distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), phosphatidyl lipids or a mixture thereof.

In some embodiments, a suitable non-cationic lipid is a phosphatidyl lipid. In some embodiments, a suitable phosphatidyl lipid is a sphingolipid. In some specific embodiments, a suitable sphingolipid is sphingomylin.

In some embodiments, one or more cholesterol-based lipids suitable for the present invention are selected from cholesterol, PEGylated cholesterol and/or DC-Chol (N,N-dimethyl-N-ethylcarboxamidocholesterol), 1,4-bis(3-N-oleylamino-propyl)piperazine.

In some embodiments, one or more PEG-modified lipids suitable for the present invention comprise a poly(ethylene) glycol chain of up to 5 kDa in length covalently attached to a lipid with alkyl chain(s) of $C_6$-$C_{20}$ length. In some embodiments, a suitable PEG-modified lipid is a derivatized ceramide such as N-Octanoyl-Sphingosine-1-[Succinyl (Methoxy Polyethylene Glycol)-2000]. In some embodiments, a suitable PEG-modified or PEGylated lipid is PEGylated cholesterol or Dimyristoylglycerol (DMG)-PEG-2K. In some embodiments, the one or more PEG-modified lipids are selected form the group consisting of DMG-PEG, C8-PEG, DOG PEG, ceramide PEG, DSPE-PEG and combination thereof. In some embodiments, the one or more PEG-modified lipids constitute about 1-10% (e.g., about 1-8%, about 1-6%, or about 1-5%) by molar ratio of the total lipid compositions. In some embodiments, the one or more PEG-modified lipids constitute about 1, 2, 3, 4, 5, 6, 7, 8, 9 or 10% by molar ratio of the total lipid compositions. In some specific embodiments, the PEG-modified lipids constitute at least 5% by molar ratio of the total lipid composition.

In some embodiments, a suitable liposome comprises a combination selected from C12-200, sphingomyelin, DOPE, Cholesterol, and DMG PEG; C12-200, DOPE, cholesterol and DMG-PEG2K; cKK-E12, DOPE, cholesterol and DMG-PEG2K; cKK-E12, sphingomyelin, DOPE, cholesterol and DMG-PEG2K; HGT5001, DOPE, cholesterol and DMG-PEG2K; HGT4003, DOPE, cholesterol and DMG-PEG2K; DLinKC2DMA, DOPE, cholesterol and DMG-PEG2K; ICE, DOPE, cholesterol and DMG-PEG2K; or DODMA, DOPE, cholesterol and DMG-PEG2K; DODMA, sphingomyelin, DOPE, cholesterol and DMG-PEG2K; and/or combinations thereof.

In some embodiments, a suitable liposome comprises a commercial enhancer. In some embodiments, the liposome comprises a biodegradable lipid. In some embodiments, the liposome comprises a ionizable lipid. In some embodiments, the liposome comprises a cleavable lipid.

In some embodiments, a suitable liposome has a size of or less than about 250nm, 200 nm, 150 nm, 125 nm, 110 nm, 100 nm, 95 nm, 90 nm, 85 nm, 80 nm, 75 nm, 70 nm, 65nm, 60 nm, 55 nm, or 50 nm. In some embodiments, a suitable liposome has a size ranging from about 40-100 nm (e.g., about 40-90 nm, about 40-80 nm, about 40-70 nm, or about 40-60 nm). As used herein, the size of a liposome is determined by the length of the largest diameter of a liposome particle.

In some embodiments, the mRNA has a length of or greater than about 0.5 kb, 1kb, 1.5 kb, 2 kb, 2.5 kb, 3 kb, 3.5 kb, 4 kb, 4.5 kb, or 5 kb.

In some embodiments, the therapeutic protein encoded by the mRNA is a cytosolic protein. In some embodiments, the therapeutic protein encoded by the mRNA is a secreted protein. In some embodiments, the therapeutic protein encoded by the mRNA is an enzyme. In some embodiments, the enzyme is a lysosomal enzyme. In some embodiments, the therapeutic protein encoded by the mRNA is a protein associated with a CNS disease. In some embodiments, the therapeutic protein encoded by the mRNA normally functions in the neurons in the brain and/or spinal cord. In some embodiments, the therapeutic protein encoded by the mRNA normally functions in the motor neurons in the spinal cord.

In some embodiments, the therapeutic protein encoded by the mRNA is a survival of motor neuron protein. In some embodiments, the therapeutic protein encoded by the mRNA is a survival of motor neuron-1 protein. In some embodiments, the therapeutic protein encoded by the mRNA is a splice isoform, fragment or truncated version of a survival of motor neuron protein-1. In some embodiments, the SMN-1 protein comprises the amino acid sequence of SEQ ID NO:2. In some embodiments, the mRNA encoding the SMN-1 protein comprises the nucleic acid sequence of SEQ ID NO:1. In some embodiments, the mRNA encoding the SMN-1 protein is codon-optimized and comprises SEQ ID NO:3, SEQ ID NO:4, SEQ ID NO:10 or SEQ ID NO:11.

In some embodiments, the mRNA suitable for the present invention comprises a 5' UTR sequence. In some embodiments, the 5'UTR sequence comprises SEQ ID NO:7. In some embodiments, the mRNA comprises a 3' UTR. In some embodiments, the 3'UTR comprises SEQ ID NO:8 or SEQ ID NO:9. In some embodiments, the mRNA comprises a cap structure. In some embodiment, a suitable cap structure is selected from Cap 0, Cap 1, or Cap 2 structures. In some embodiments, a suitable cap structure is an Anti-Reverse Cap Analog (ARCA) or a modified ARCA.

In some embodiments, the mRNA encoding a therapeutic protein comprises one or more modified nucleotides. In some embodiments, the one or more nucleotides are selected from the group consisting of pseudouridine, 2-aminoadenosine, 2-thiouridine, inosine, pyrrolo-pyrimidine, 3-methyl adenosine, 5-mtehylcytidine, C-5 propynyl-cytidine, C-5 propynyl-uridine, 2-aminoadenosine, C5-bromouridine, C5-fluorouridine, C5-iodouridine, C5-propynyl-uridine, CS-propynyl-cytidine, C5-methylcytidine, 2-aminoadenosine, 7-deazaadenosine, 7-deazaguanosine, 8-oxoadenosine, 8-oxoguanosine, O(6)-methylguanine, N-1-methyl pseudouridine, 2-thiocytidine, and combinations thereof.

In some embodiments, the mRNA encoding a therapeutic protein is unmodified.

In some embodiments, intracellular delivery of the mRNA results in expression of the protein encoded by the mRNA. In some embodiments, the encoded protein is expressed within the cytosol of the neurons. In some embodiments, the encoded protein is expressed and secreted extracellularly form the neurons after expression.

In some embodiments, the mRNA is administered at a dose ranging from about 0 01-10.0 mg/kg body weight, for example, about 0.01-9.0, 0.01-8.0, 0.01-70, 0.01-6.0, 0.01-5.0, 0.01-4.0, 0.01-3.0, 0.01-2.5, 0.01-2.0, 0.01-1.5, 0.01-1.0, 0.01-0.5, 0.01-0.25, 0.01-0.1, 0.1-10.0, 0.1-5.0, 0.1-4.0, 0.1-3.0, 0.1-2.0, 0.1-1.0, 0.1-0.5 mg/kg body weight. In some embodiments, the mRNA is administered at a dose of or less than about 10.0, 9.0, 8.0, 7.0, 6.0, 5.0, 4.5, 4.0, 3.5, 3.0, 2.5, 2.0, 1.5, 1,0, 0.8, 0.6, 0.5, 0.4, 0.3, 0.2, 0.1, 0.05, 0.04, 0.03, 0.02, or 0.01 mg/kg body weight.

In some embodiments, the mRNA is delivered without inducing substantial toxicity or immune response.

In another aspect, the present invention provides methods of treating a disease, disorder or condition associated with deficiency of a protein in the central nervous system (CNS) by delivering a messenger RNS (mRNA) encoding the protein that is deficient to the CNS using a method described herein. In some embodiments, the CNS disease, disorder or condition is the result of a protein deficiency. In some embodiments, the CNS disease, disorder or condition is the result of a protein deficiency in the motor neurons.

Among other things, the present invention provides methods and compositions of treating spinal muscular atrophy.

In one aspect, the present invention provides a method of treating spinal muscular atrophy by delivering a messenger RNA (mRNA) encoding a Survival of Motor Neuron (SMN) protein to the CNS using a method described herein.

In another aspect, the present invention provides a composition for treating spinal muscular atrophy, comprising an mRNA encoding the Survival of Motor Neuron (SMN) protein, encapsulated within a liposome; wherein the mRNA comprises SEQ ID NO:3, SEQ ID NO:4, SEQ ID NO:10 or SEQ ID NO: 11 (corresponding to codon-optimized human SMN mRNA), and further wherein the liposome comprises cationic or non-cationic lipid, cholesterol-based lipid and PEG-modified lipid.

In a related aspect, the present invention provides a composition for treating spinal muscular atrophy, comprising an mRNA encoding the Survival of Motor Neuron (SMN) protein, encapsulated within a liposome, wherein the liposome comprises a cationic lipid of formula I-c1-a:

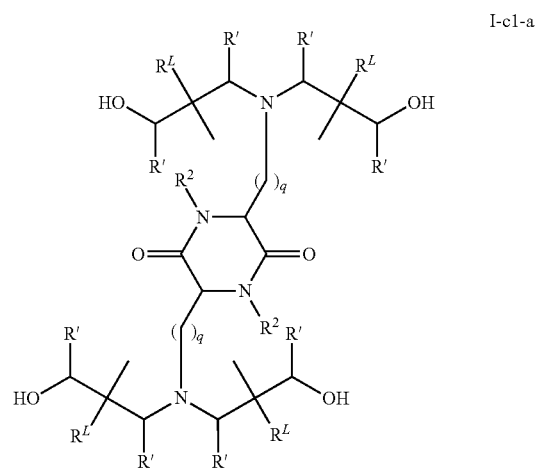

or a pharmaceutically acceptable salt thereof, wherein:
each $R^2$ independently is hydrogen or $C_{1-3}$ alkyl;
each q independently is 2 to 6;
each R' independently is hydrogen or $C_{1-3}$ alkyl;
and each $R^L$ independently is $C_{8-12}$ alkyl.

In some embodiments, a suitable cationic lipid is cKK-E12:

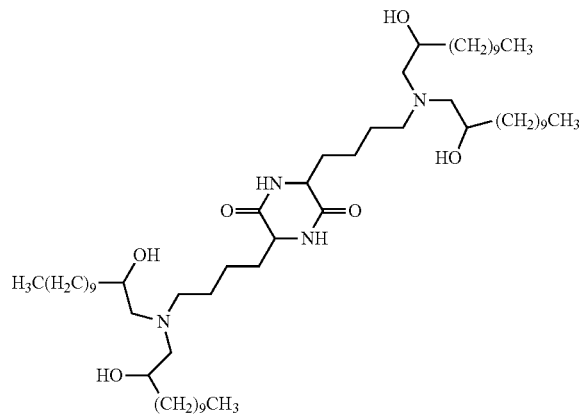

In some embodiments, the present invention provides a composition for treating spinal muscular atrophy, comprising an mRNA encoding the Survival of Motor Neuron (SMN) protein, encapsulated within a liposome; wherein the liposome comprises a combination selected from
  C12-200, sphingomyelin, DOPE, Cholesterol, and DMG PEG;
  C12-200, DOPE, cholesterol and DMG-PEG2K;
  cKK-E12, DOPE, cholesterol and DMG-PEG2K;
  cKK-E12, sphingomyelin, DOPE, cholesterol and DMG-PEG2K;
  HGT5001, DOPE, cholesterol and DMG-PEG2K;
  HGT4003, DOPE, cholesterol and DMG-PEG2K;
  DLinKC2DMA, DOPE, cholesterol and DMG-PEG2K;
  ICE, DOPE, cholesterol and DMG-PEG2K;
  DODMA, DOPE, cholesterol and DMG-PEG2K; or
  DODMA, sphingomyelin, DOPE, cholesterol and DMG-PEG2K.

Other features, objects, and advantages of the present invention are apparent in the detailed description, drawings and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

BRIEF DESCRIPTION OF THE FIGURES

The drawings are for illustration purposes only not for limitation.

FIG. 8A-C illustrates multiplex nucleic acid in situ detection of human Survival of Motor Neuron (hSMN-1) mRNA in (A) Cervical, (B) Thoracic and (C) Lumbar spinal tissue, 24 hours post intrathecal delivery using liposome formulation 7.

FIG. 13A-C illustrates multiplex nucleic acid in situ detection of human Survival of Motor Neuron (hSMN-1) mRNA in (A) Cervical, (B) Thoracic and (C) Lumbar spinal tissue, 24 hours post intrathecal delivery using liposome formulation 12.

DEFINITIONS

Figure 1:
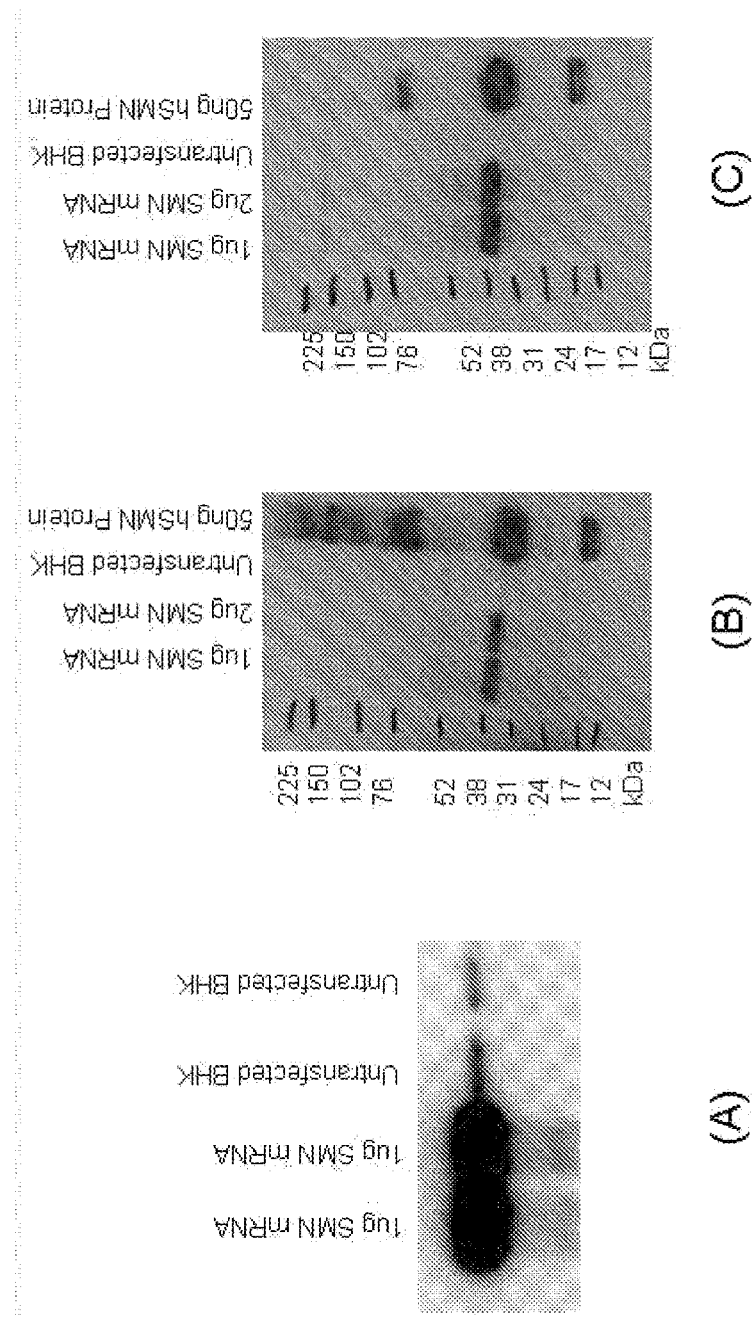
FIG. 1 illustrates detection via western blot of human SMN-1 protein derived from exogenous hSMN-1 mRNA that was transfected into BHK-21 cells. Various antibodies specific to human SMN were employed: (A) anti-SMN 4F11 antibody at 1:1,000 dilution; (B) Pierce PA5-27309 a-SMN antibody at 1:10,000 dilution; and (C) LSBio C138149 a-SMN antibody at 1:10,000 dilution.
Figure 2A:
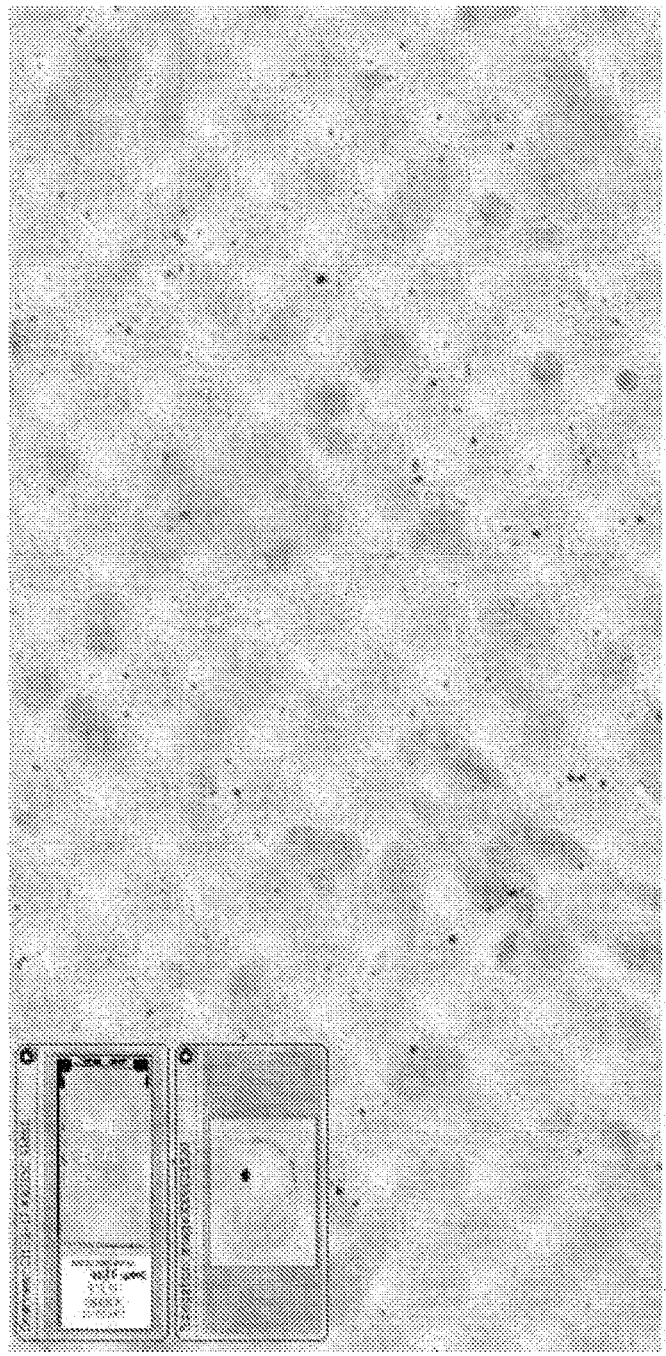
FIG. 2A-C illustrates multiplex nucleic acid in situ detection of human Survival of Motor Neuron (hSMN-1) mRNA in (A) Cervical, (B) Thoracic and (C) Lumbar spinal tissue, 24 hours post intrathecal delivery using liposome formulation 1.
Figure 2B:
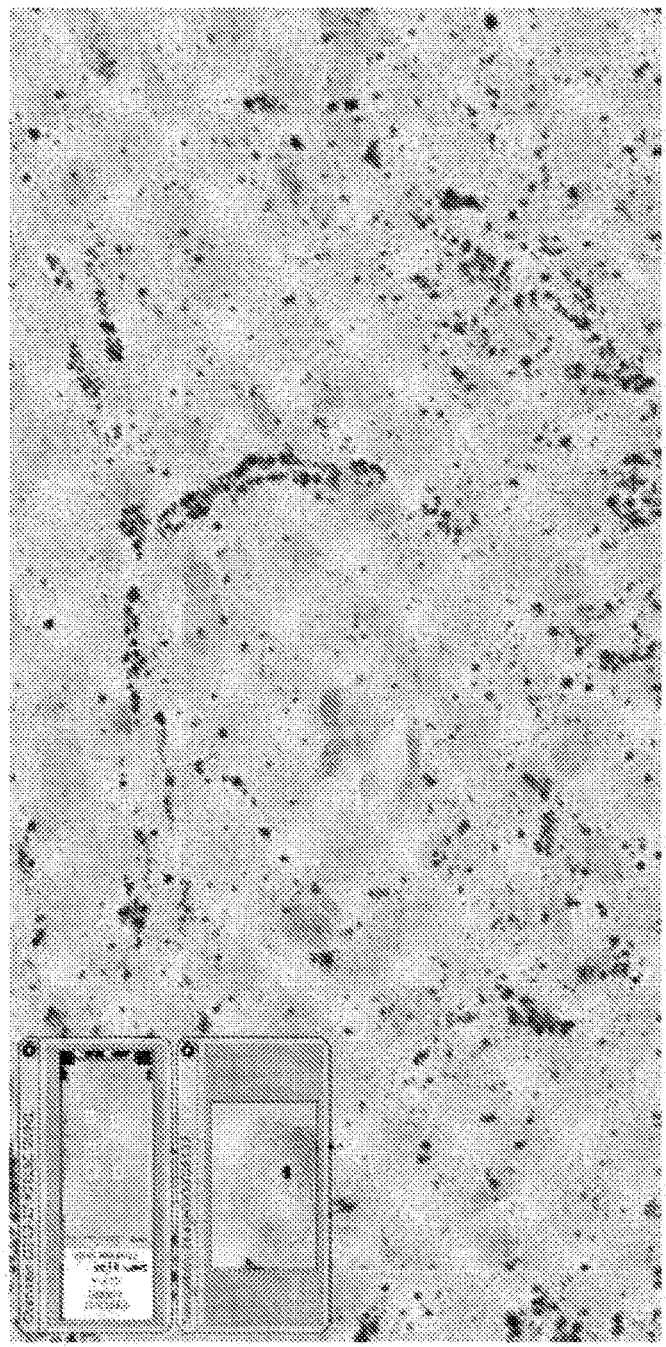
Figure 2C:
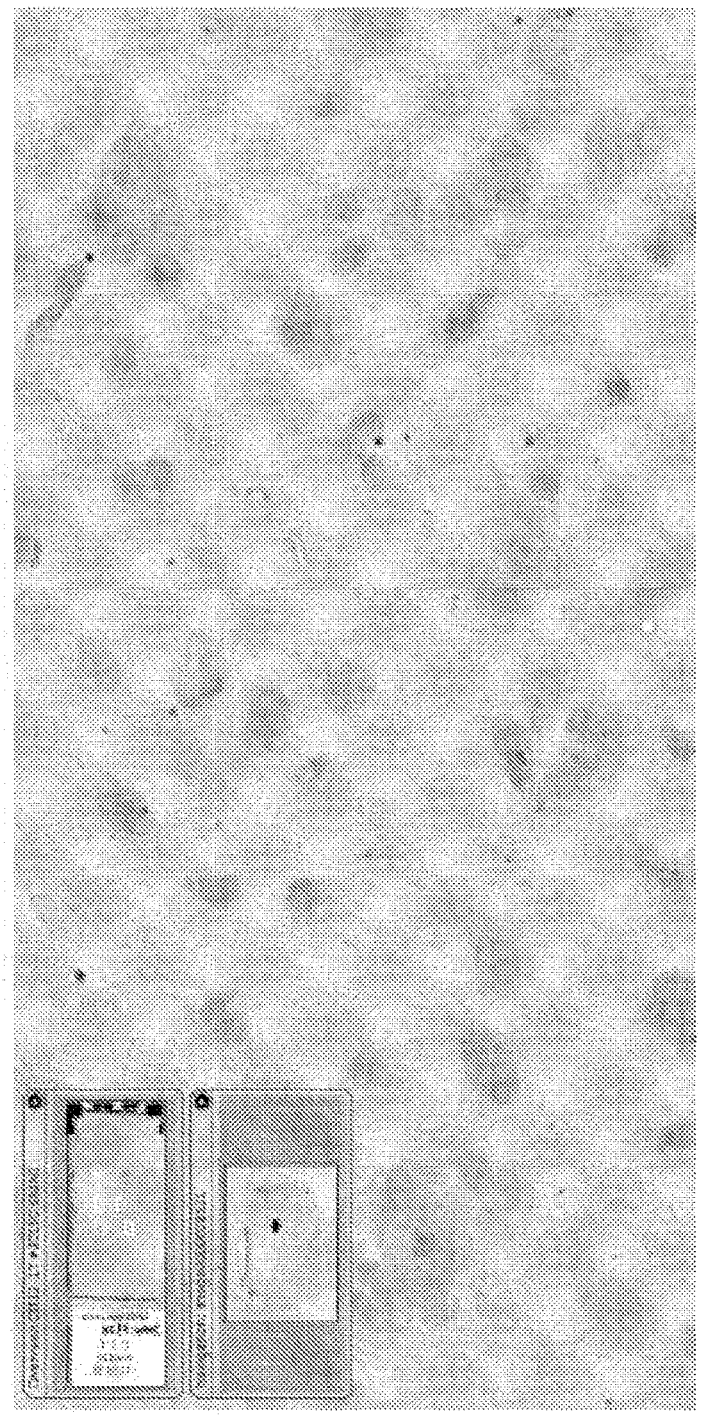
Figure 3A:
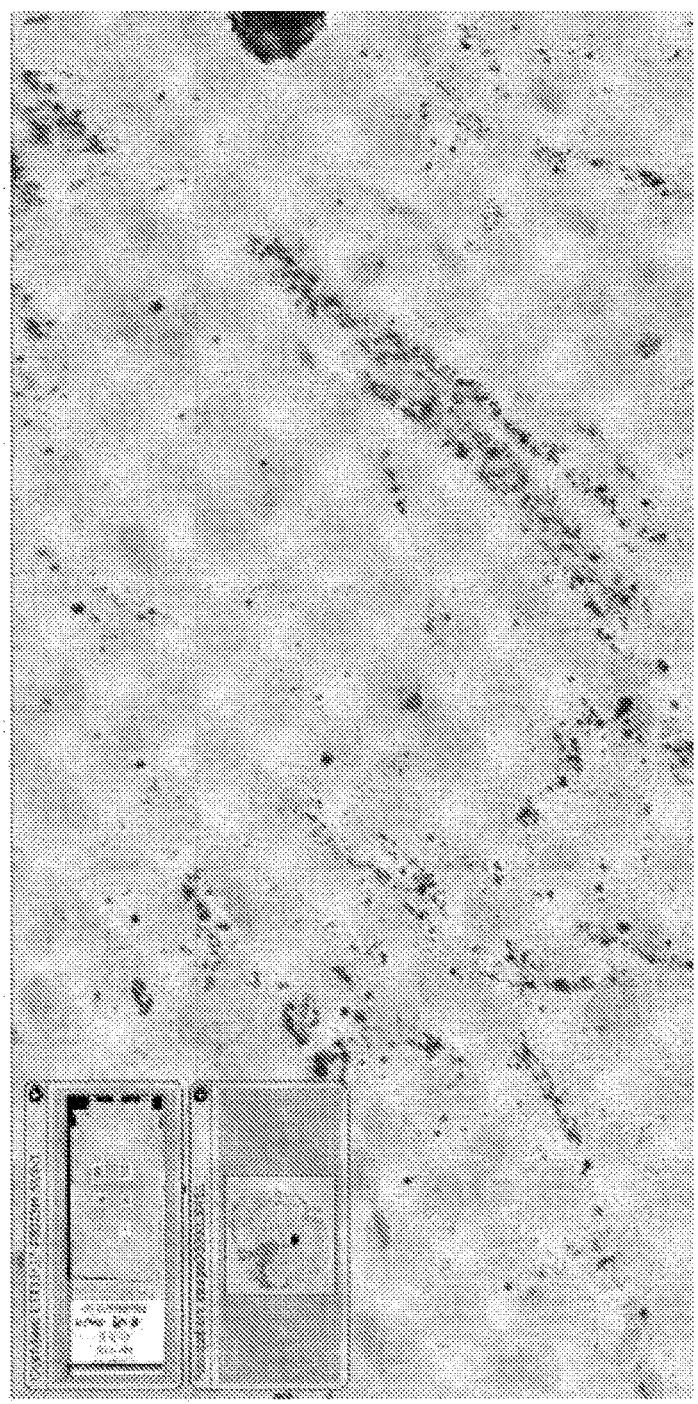
FIG. 3A-C illustrates multiplex nucleic acid in situ detection of human Survival of Motor Neuron (hSMN-1) mRNA in (A) Cervical, (B) Thoracic and (C) Lumbar spinal tissue, 24 hours post intrathecal delivery using liposome formulation 2.
Figure 3B:
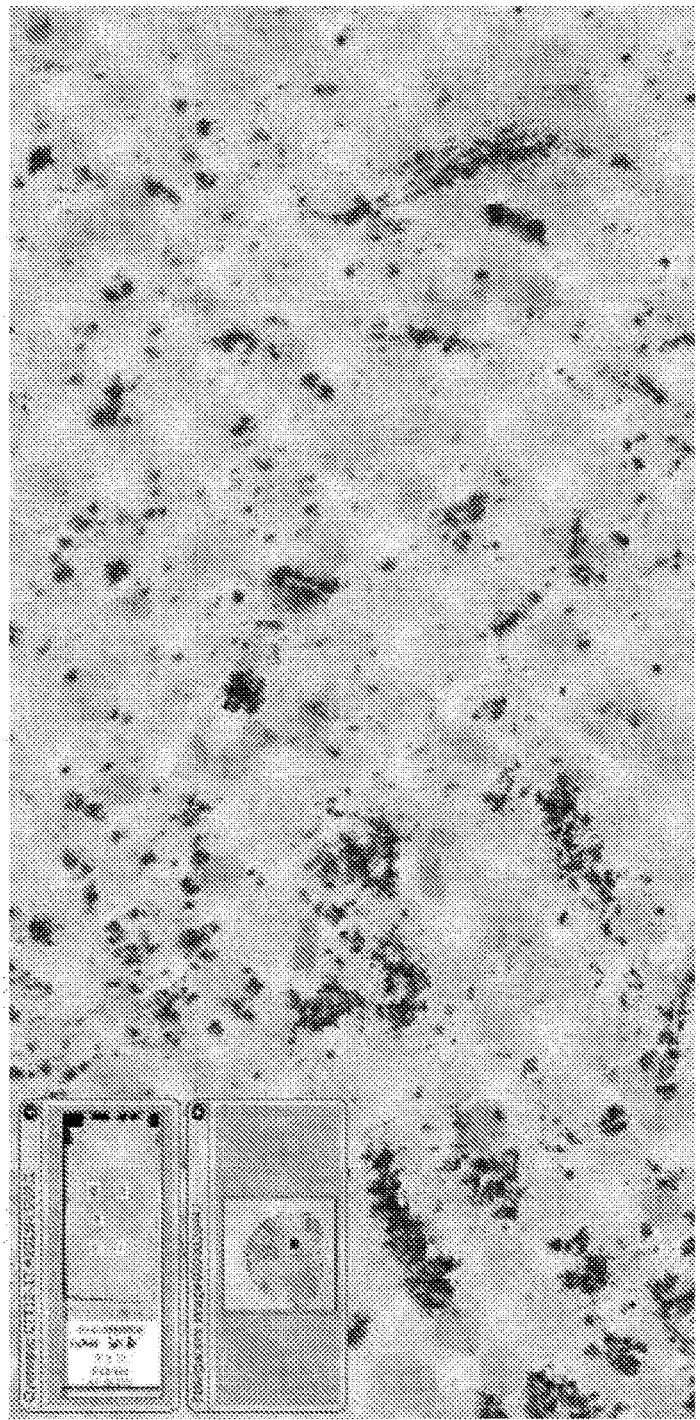
Figure 3C:
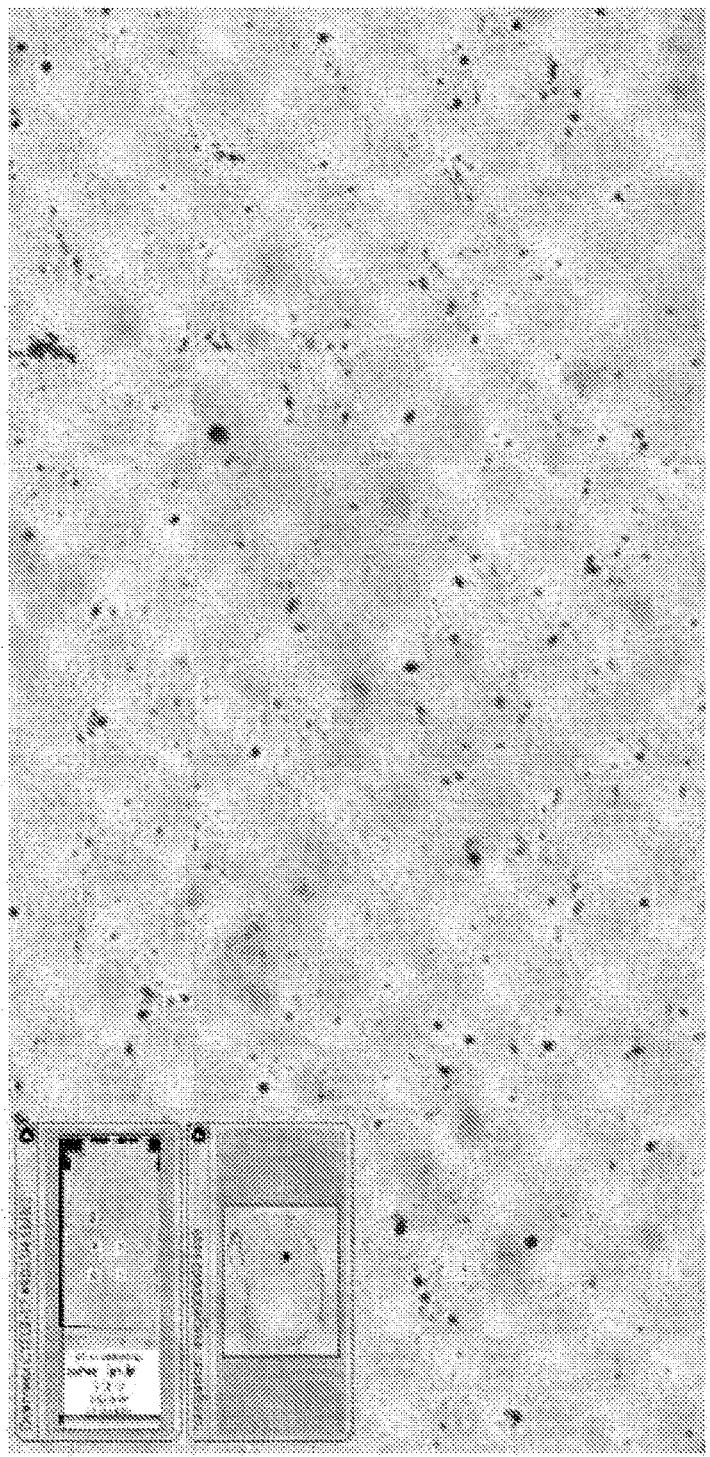
Figure 4A:
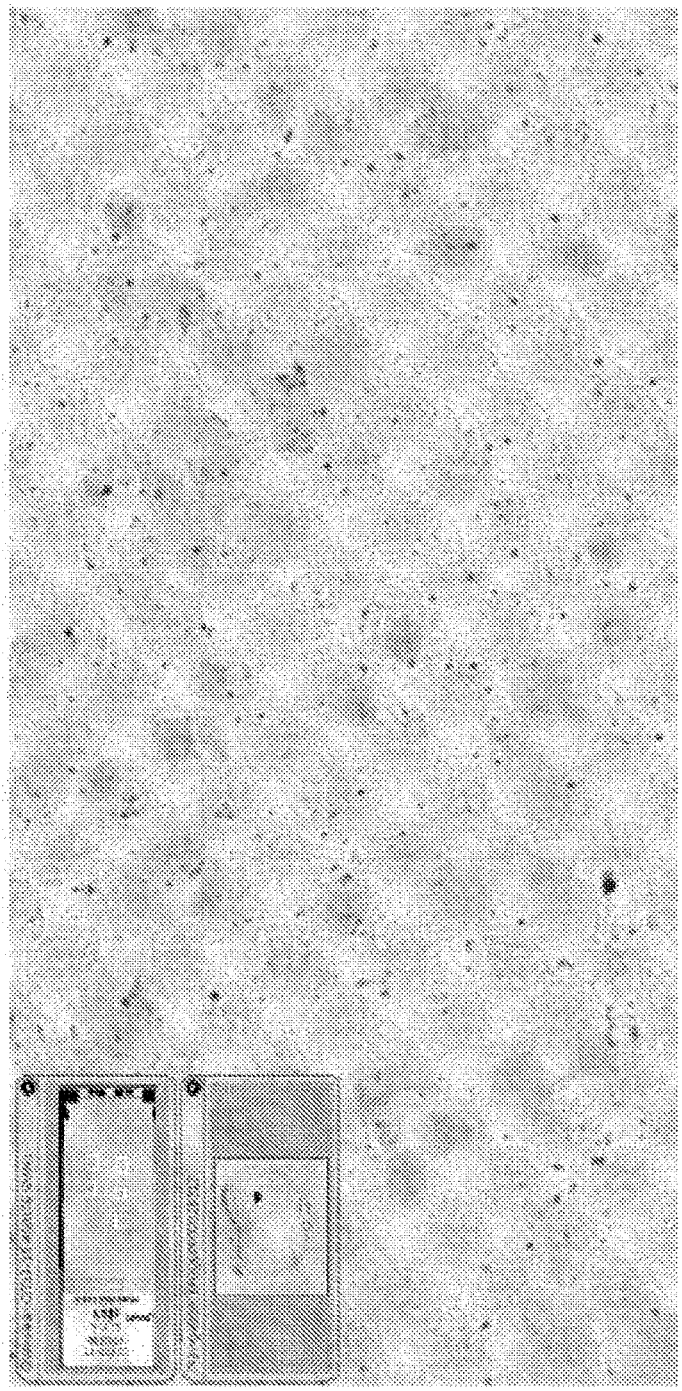
FIG. 4A-C illustrates multiplex nucleic acid in situ detection of human Survival of Motor Neuron (hSMN-1) mRNA in (A) Cervical, (B) Thoracic and (C) Lumbar spinal tissue, 24 hours post intrathecal delivery using liposome formulation 3.
Figure 4B:
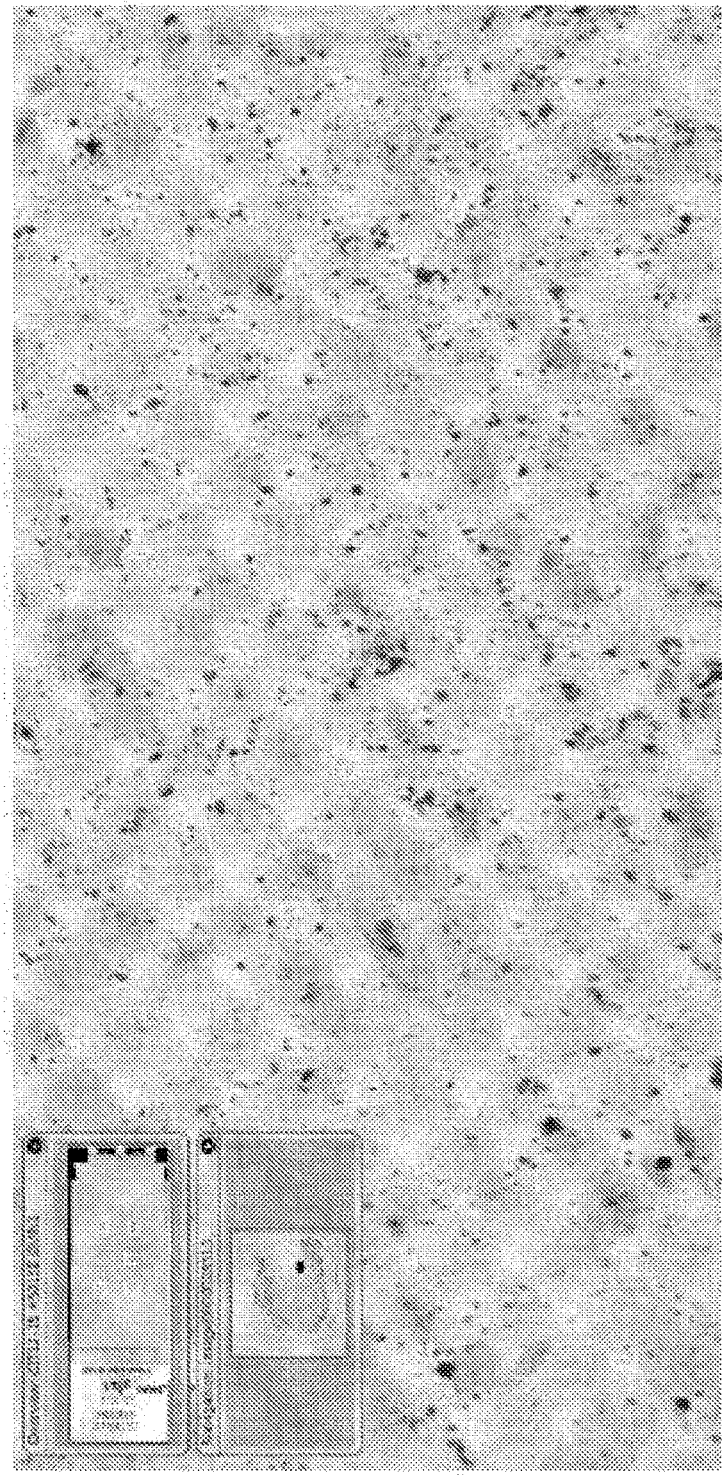
Figure 4C:
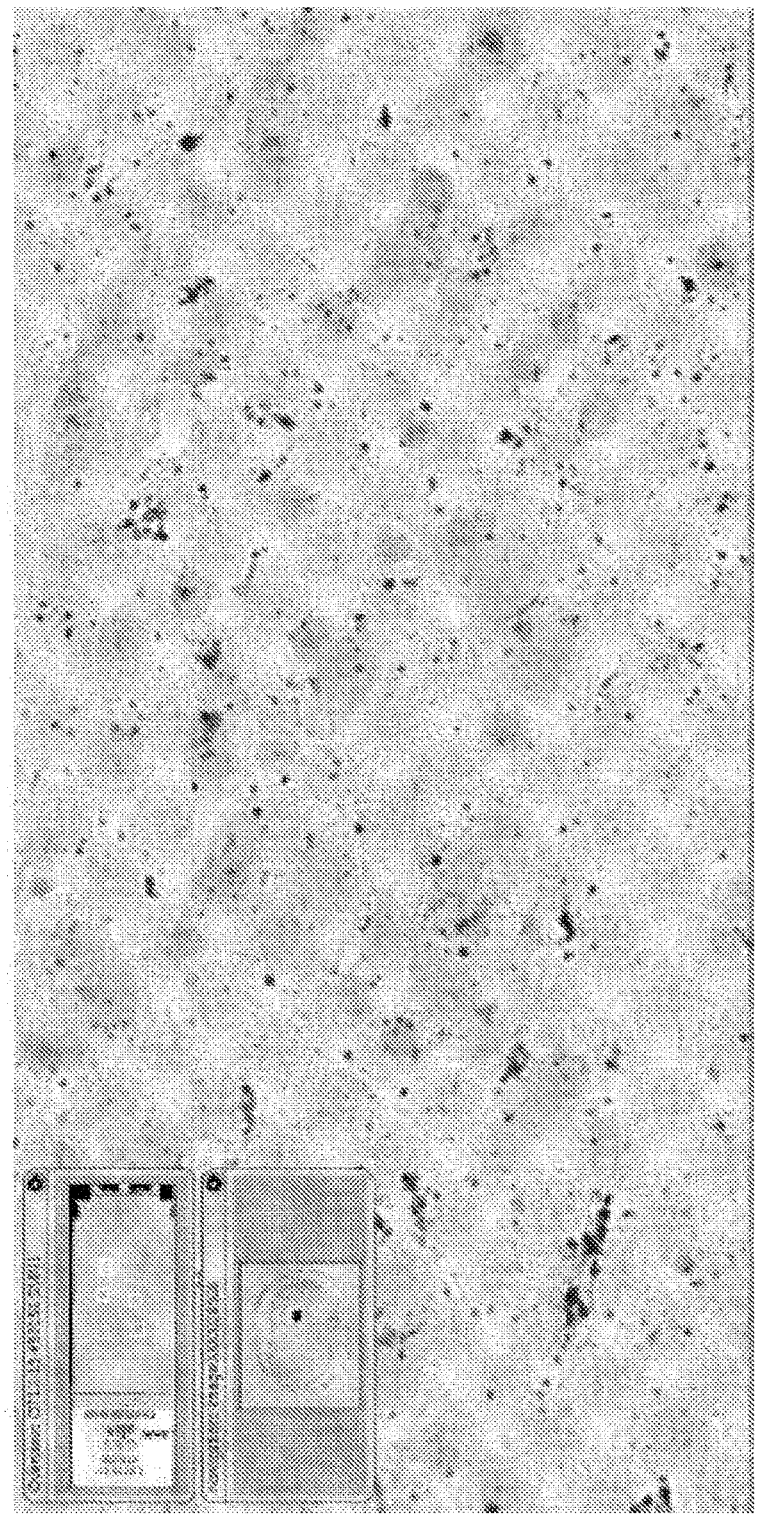
Figure 5A:
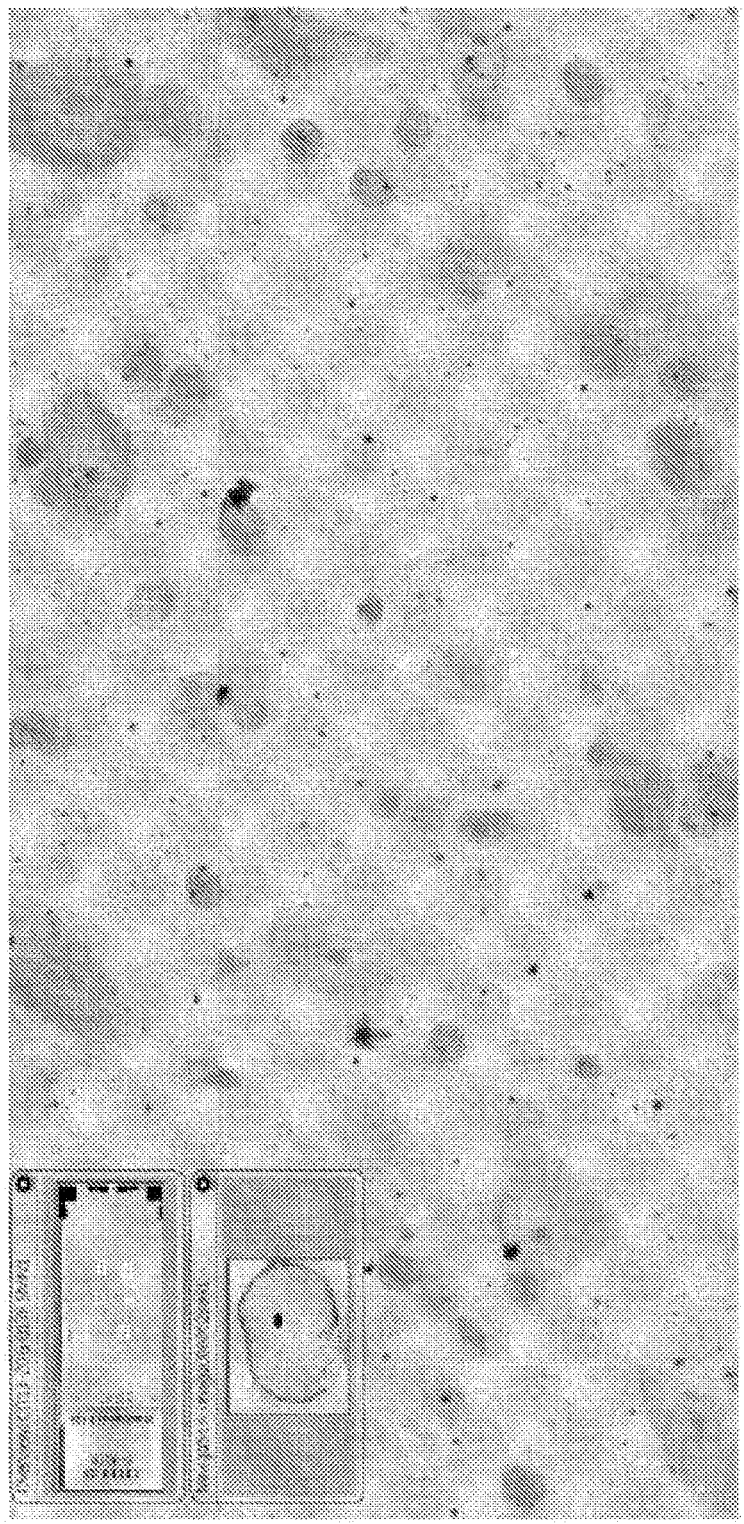
FIG. 5A-C illustrates multiplex nucleic acid in situ detection of human Survival of Motor Neuron (hSMN-1) mRNA in (A) Cervical, (B) Thoracic and (C) Lumbar spinal tissue, 24 hours post intrathecal delivery using liposome formulation 4.
Figure 5B:
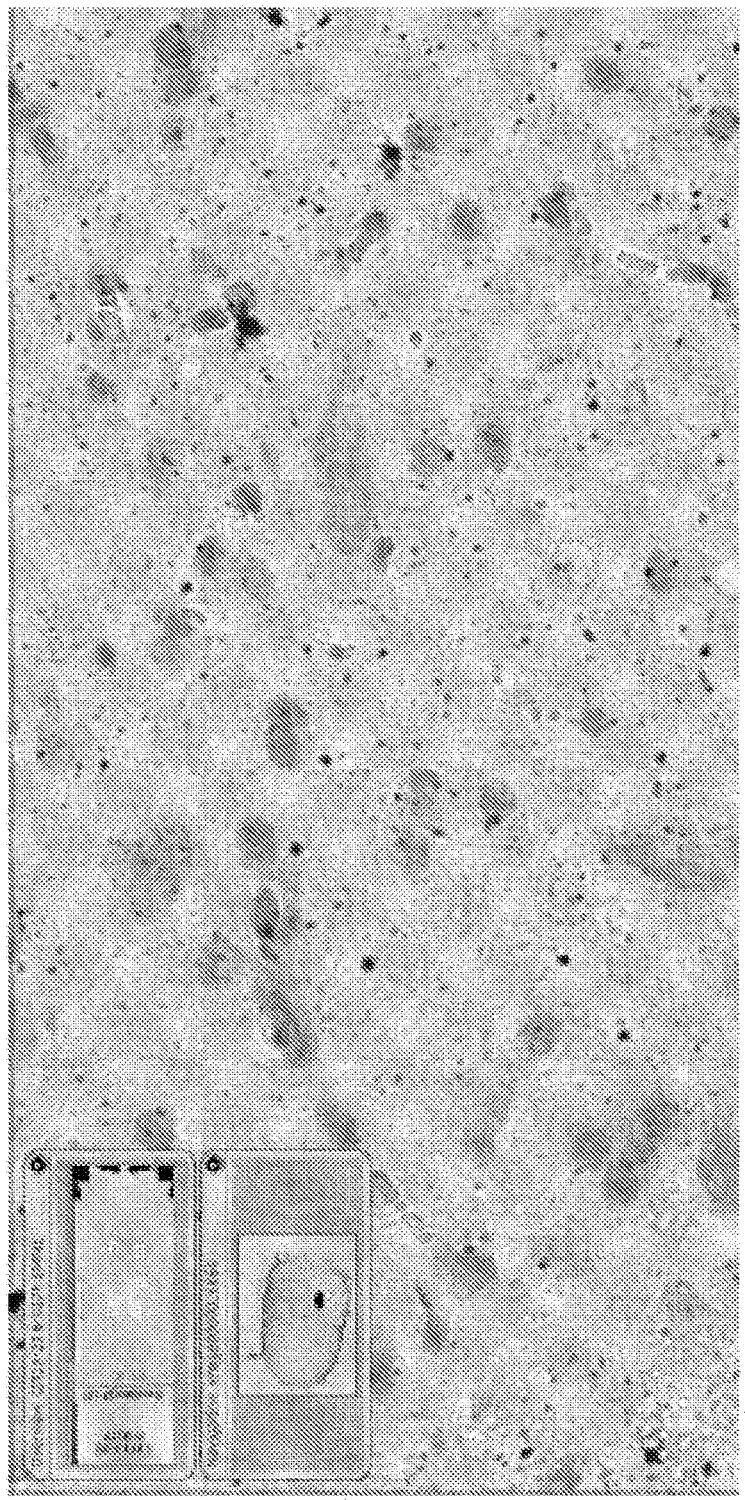
Figure 5C:
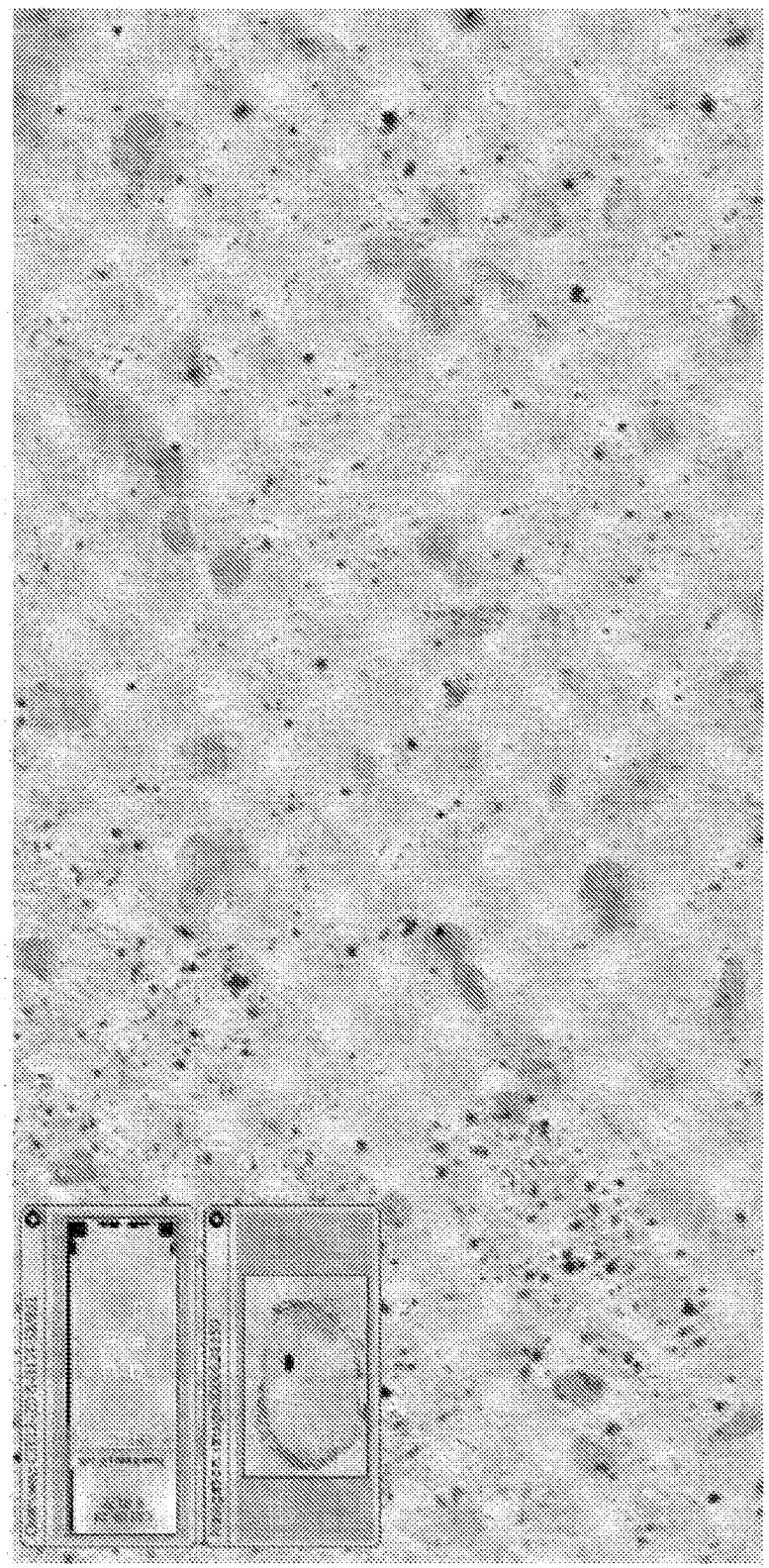
Figure 6A:
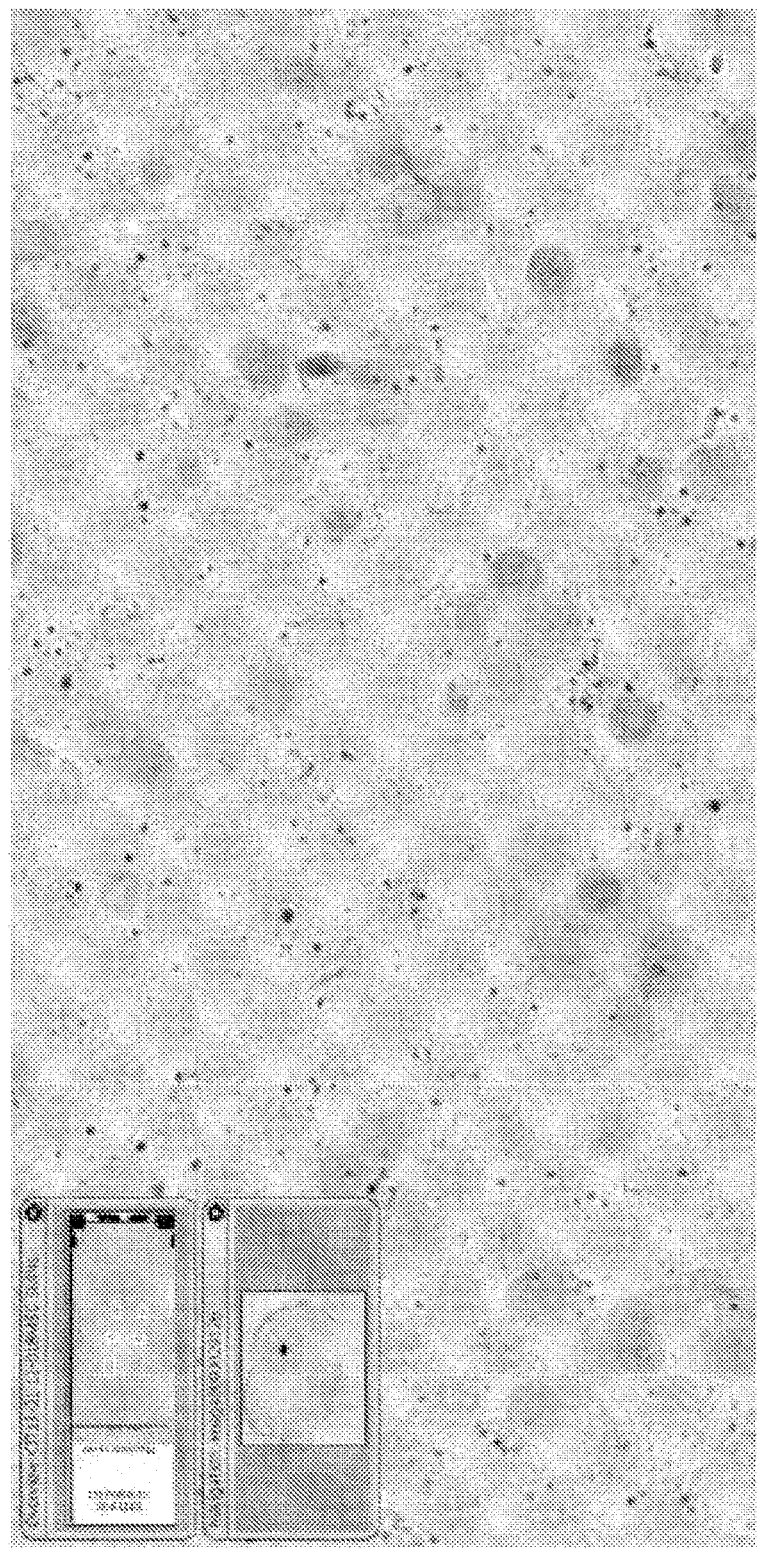
FIG. 6A-C illustrates multiplex nucleic acid in situ detection of human Survival of Motor Neuron (hSMN-1) mRNA in (A) Cervical, (B) Thoracic and (C) Lumbar spinal tissue, 24 hours post intrathecal delivery using liposome formulation 5.
Figure 6B:
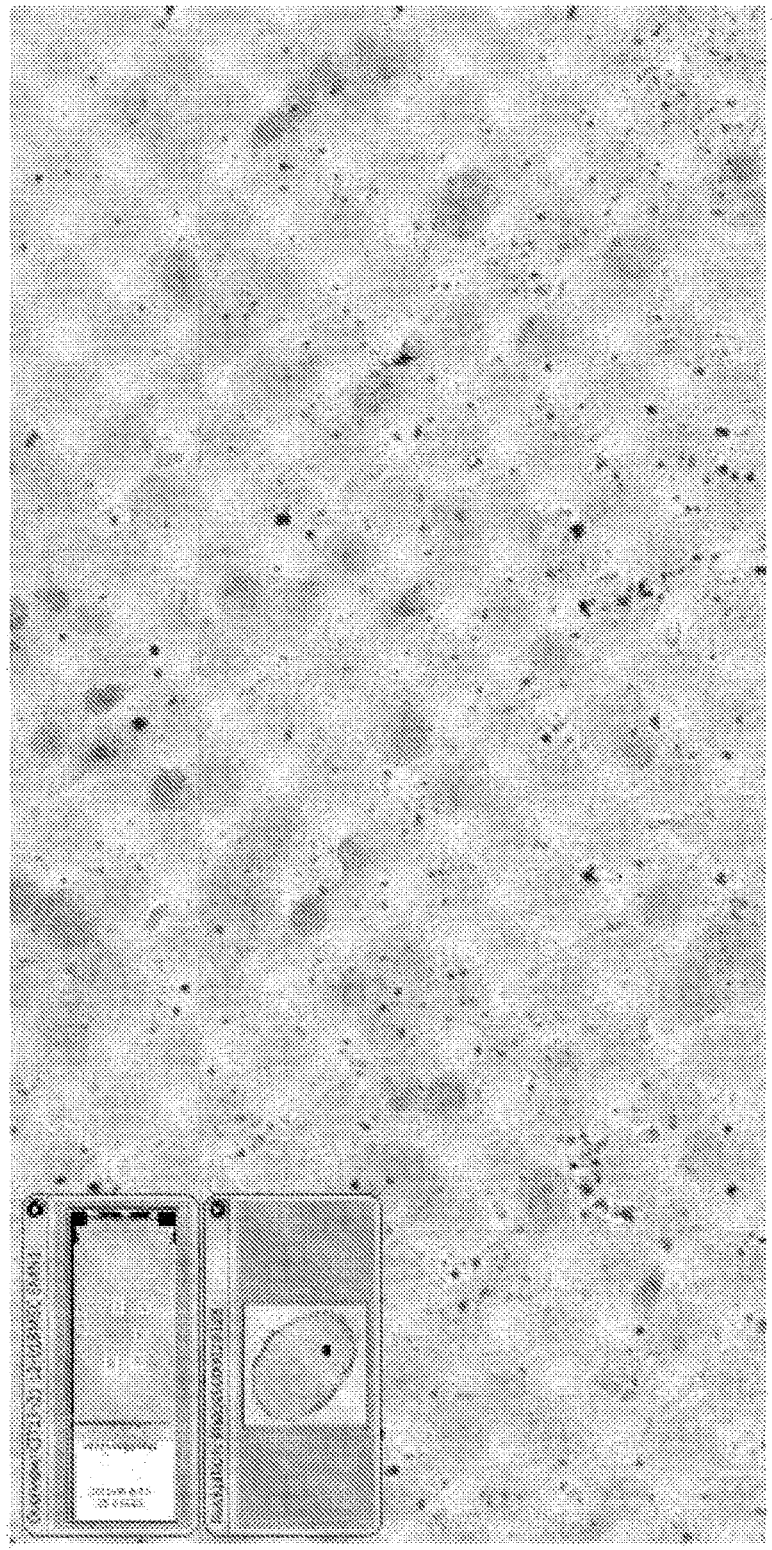
Figure 6C:
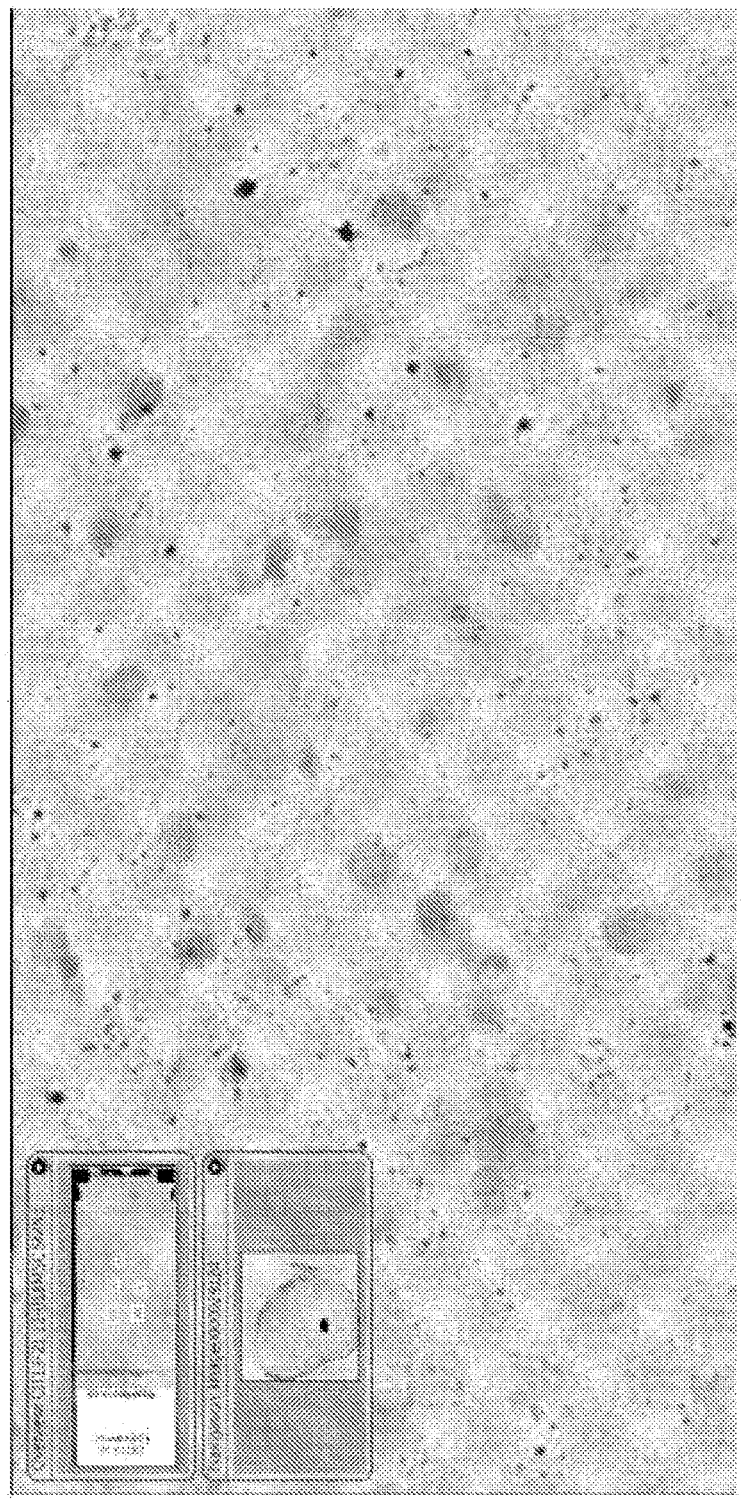
Figure 7A:
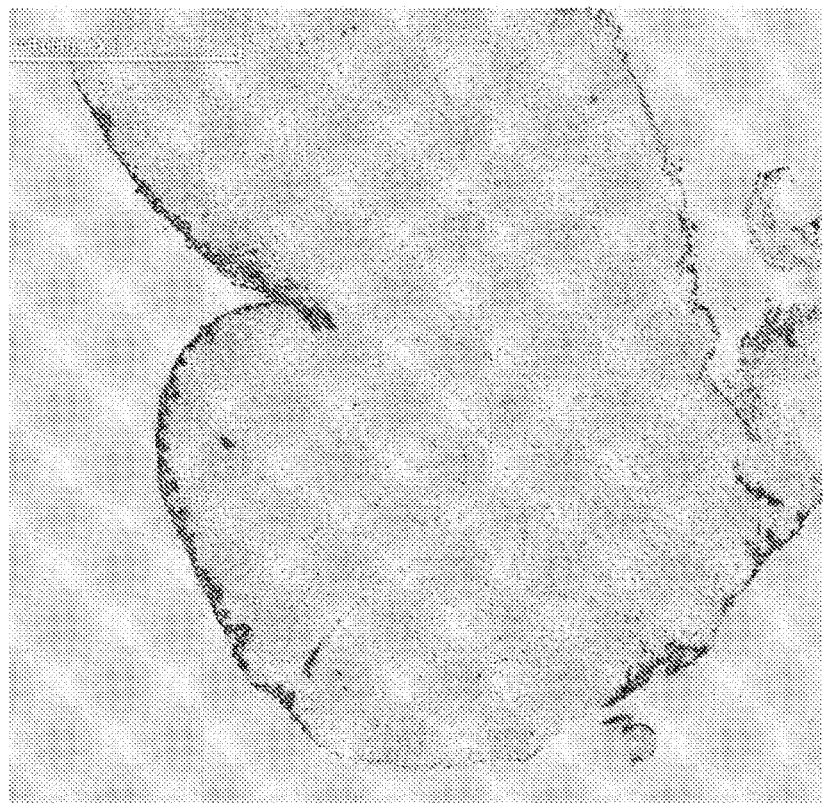
FIG. 7A-C illustrates multiplex nucleic acid in situ detection of human Survival of Motor Neuron (hSMN-1) m RNA in (A) Cervical, (B) Thoracic and (C) Lumbar spinal tissue, 24 hours post intrathecal delivery using liposome formulation 6.
Figure 7B:
Figure 7C:
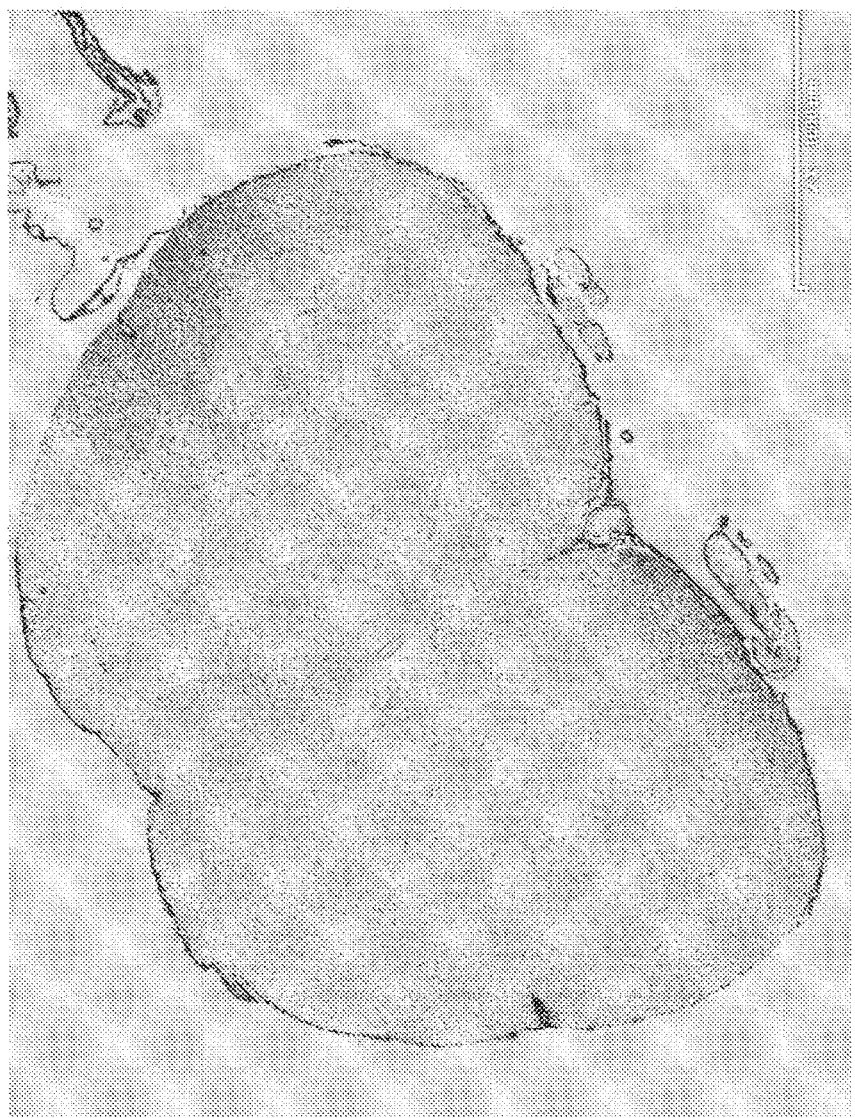
Figure 8B:
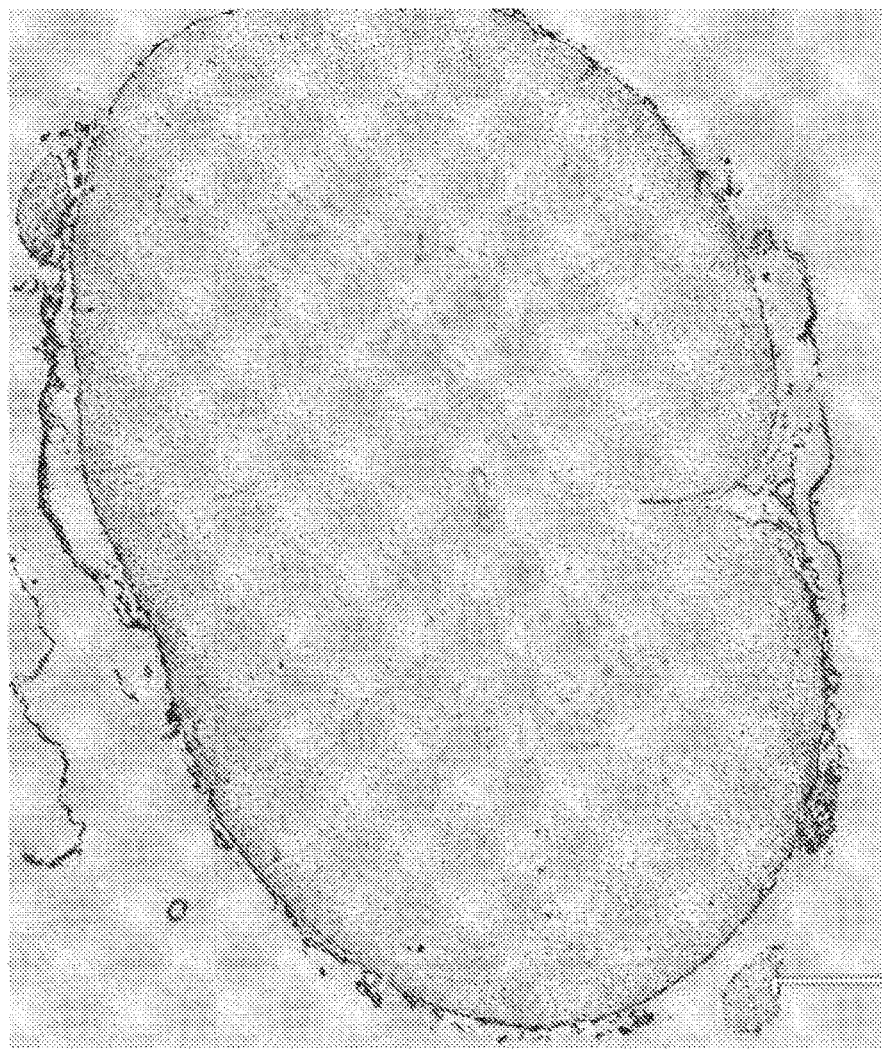
Figure 8C:
Figure 9A:
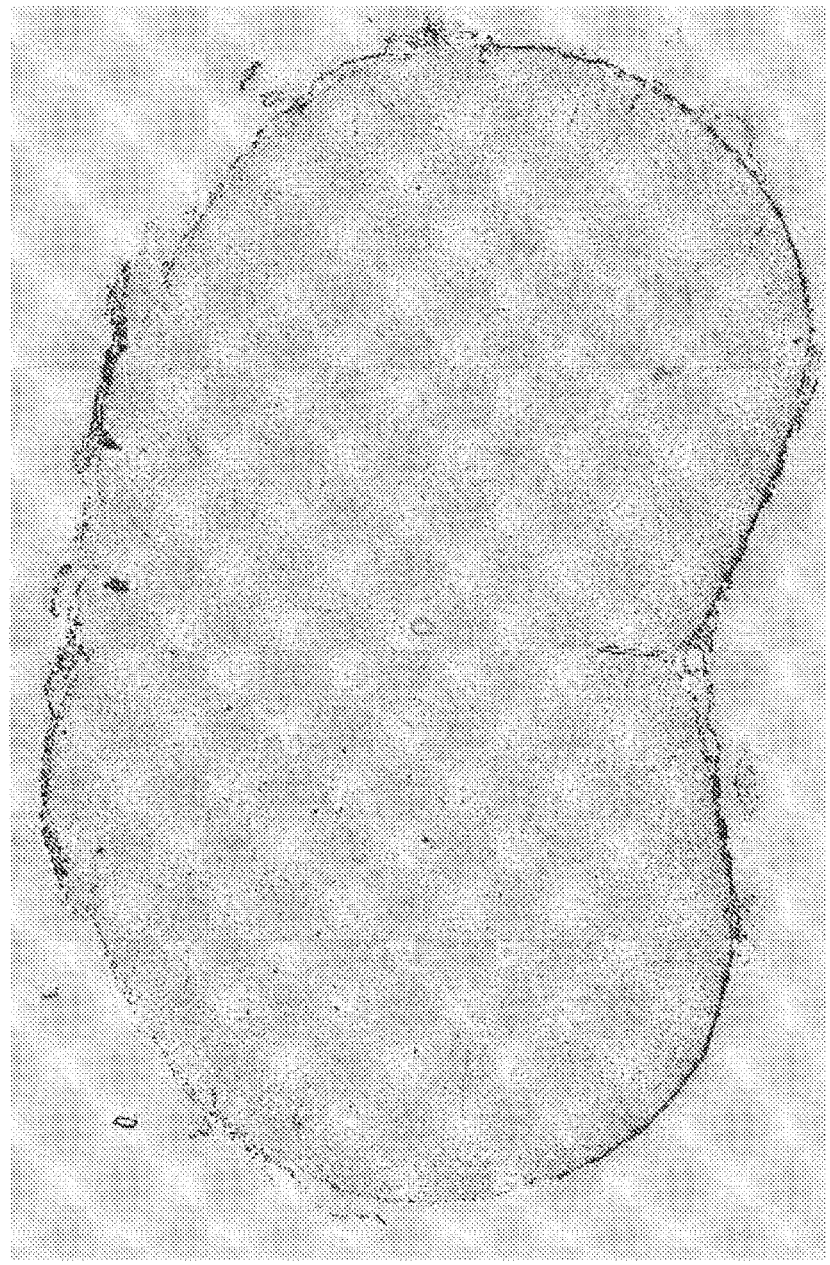
FIG. 9A-C illustrates multiplex nucleic acid in situ detection of human Survival of Motor Neuron (hSMN-1) mRNA in (A) Cervical, (B) Thoracic and (C) Lumbar spinal tissue, 24 hours post intrathecal delivery using liposome formulation 8.
Figure 9B:
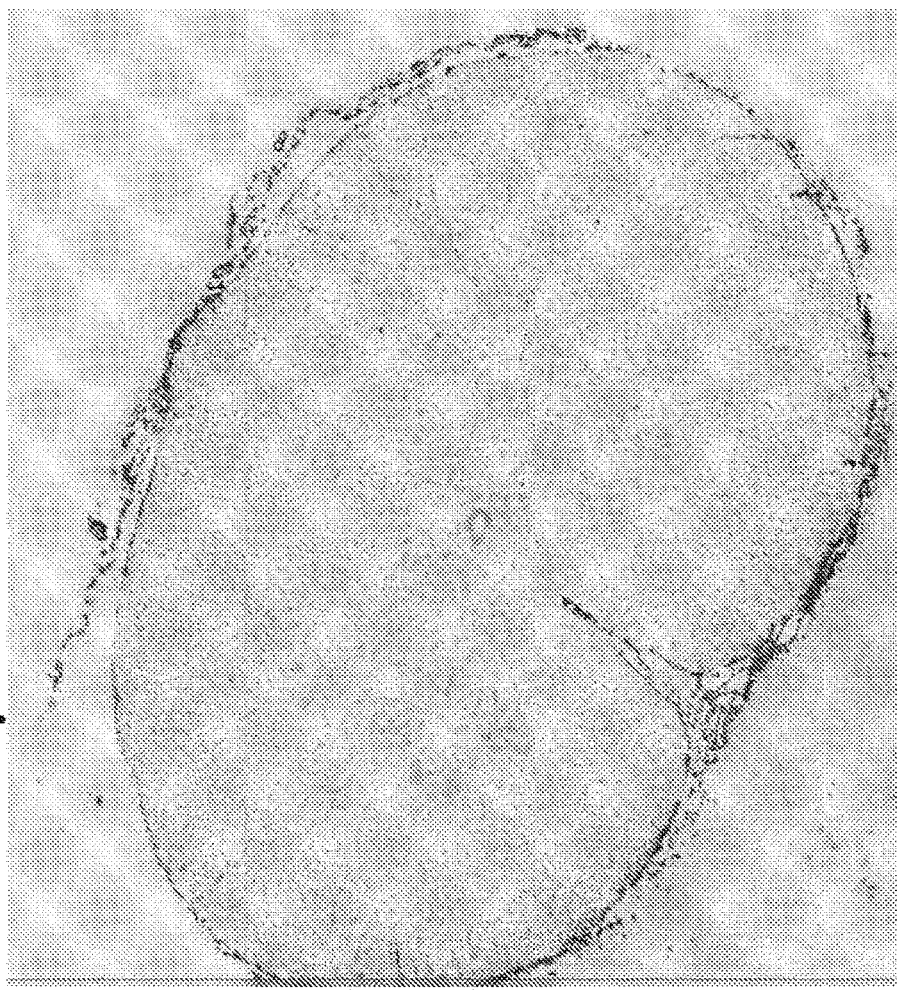
Figure 9C:
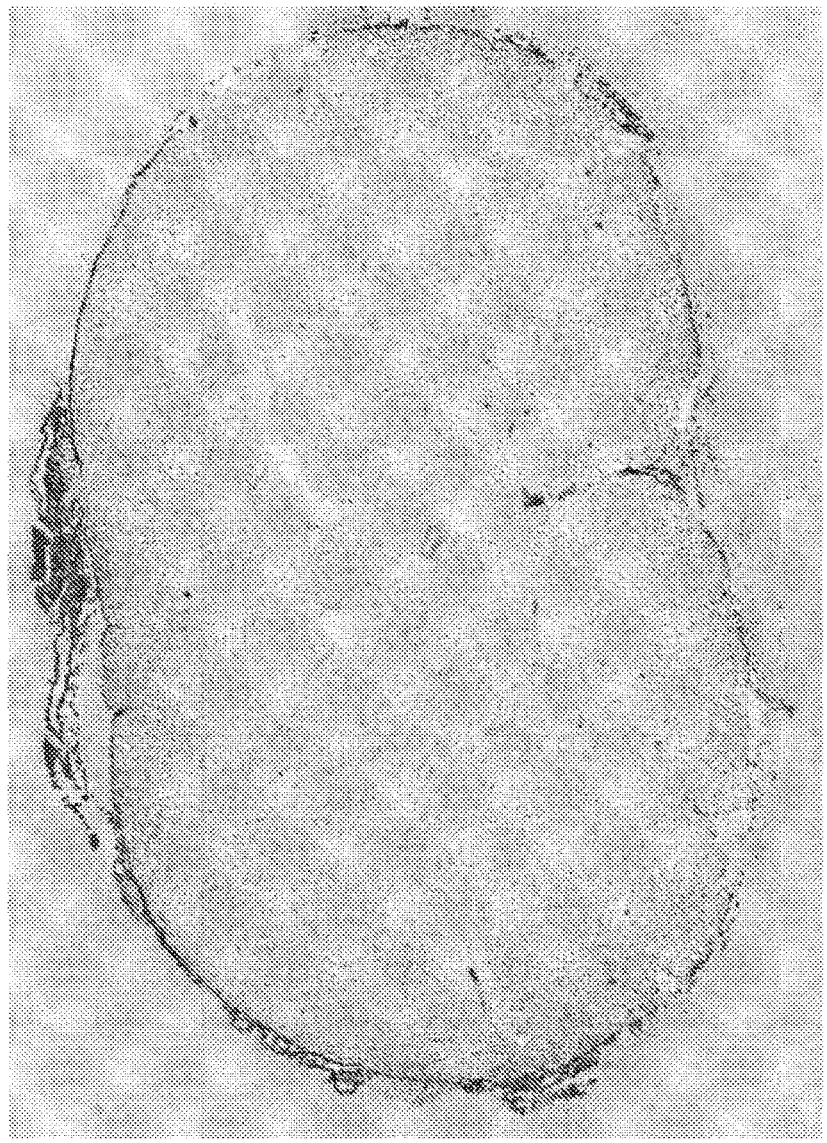
Figure 10A:
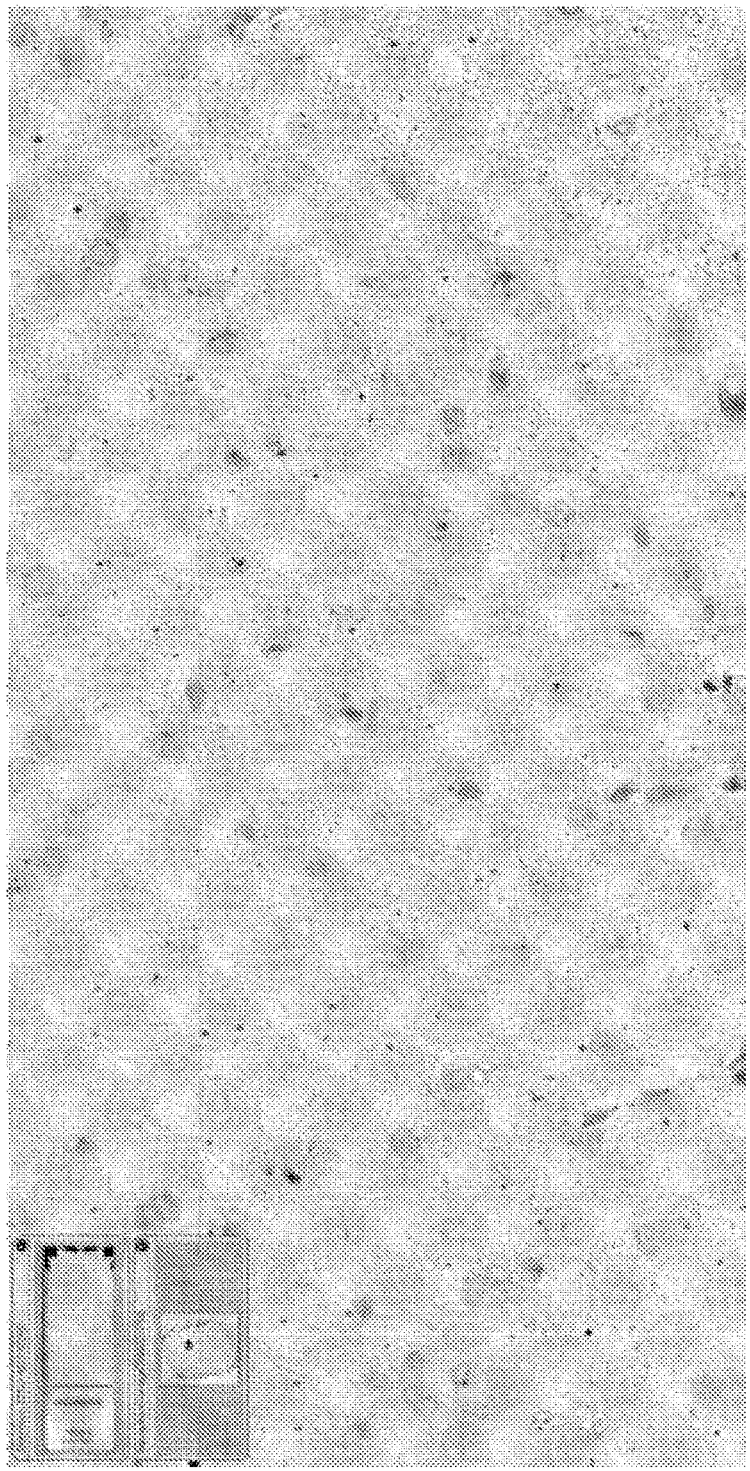
FIG. 10A-C illustrates multiplex nucleic acid in situ detection of human Survival of Motor Neuron (hSMN-1) mRNA in (A) Cervical, (B) Thoracic and (C) Lumbar spinal tissue, 24 hours post intrathecal delivery using liposome formulation 9.
Figure 10B:
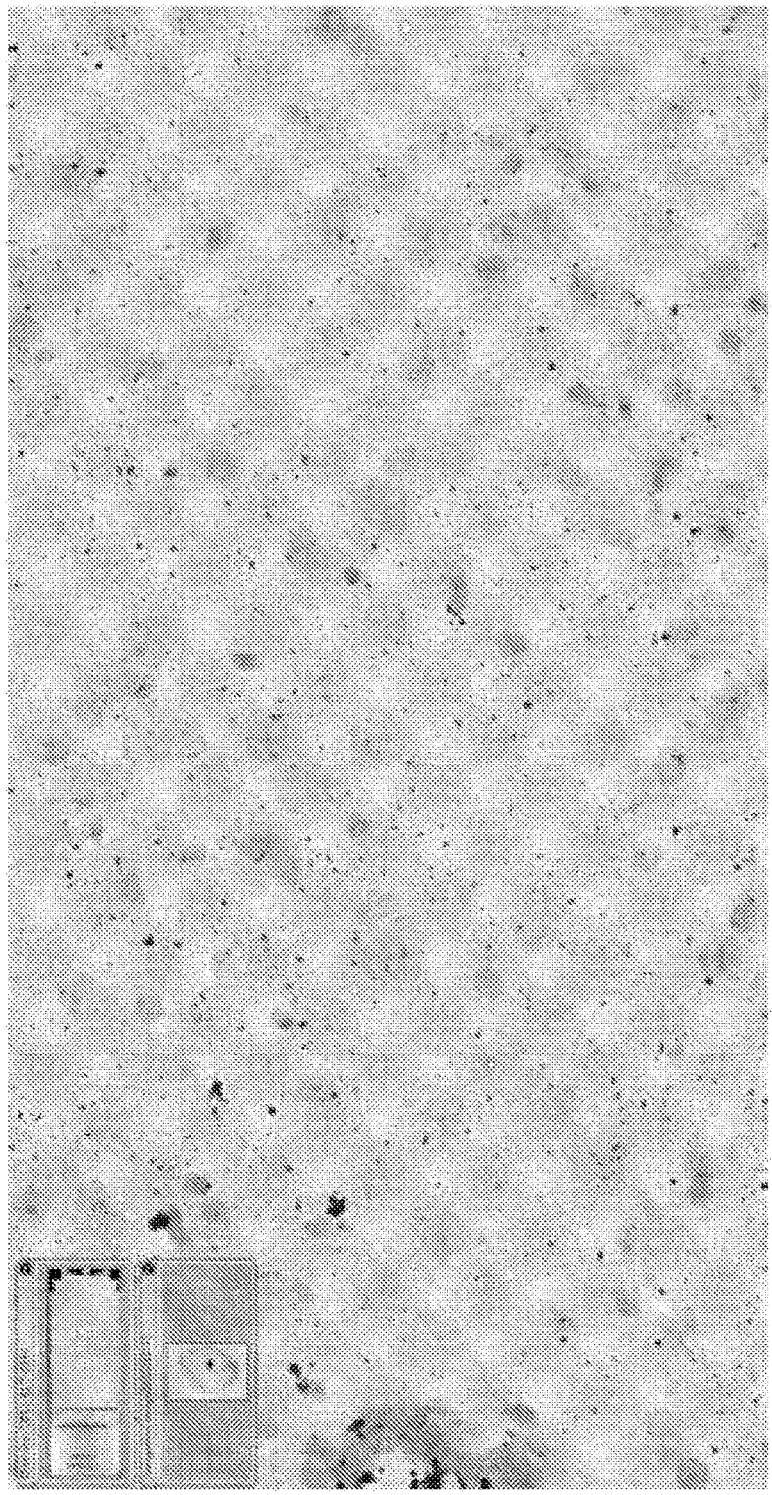
Figure 10C:
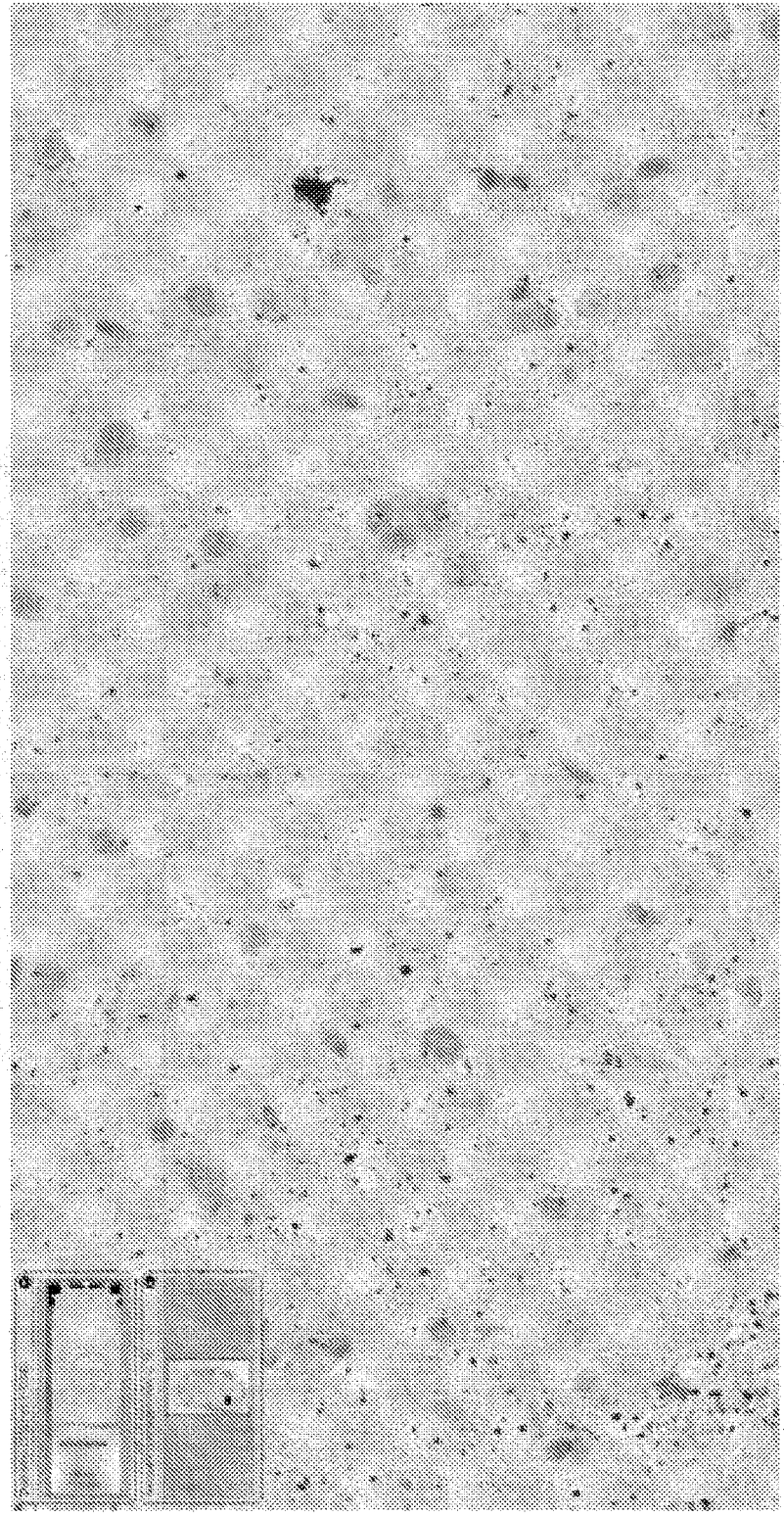
Figure 11A:
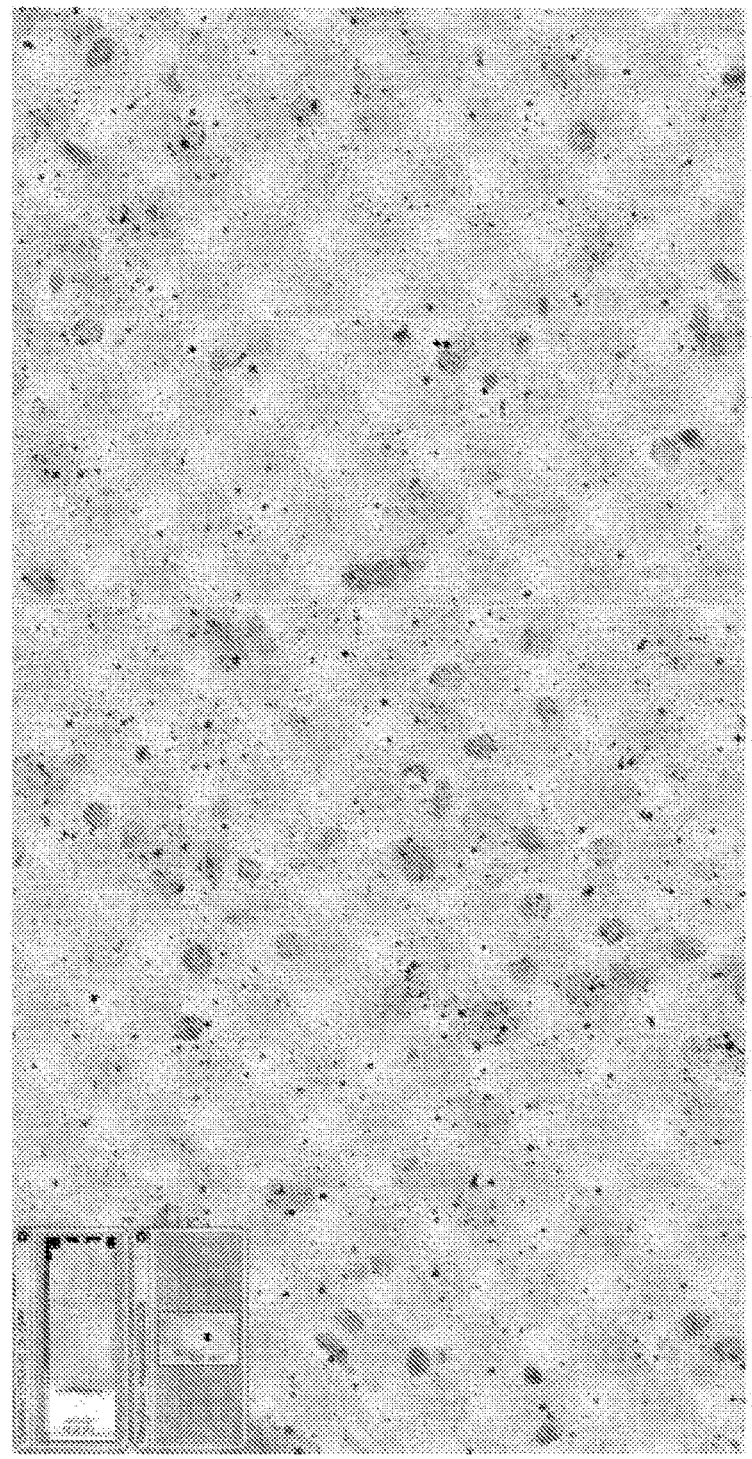
FIG. 11A-C illustrates multiplex nucleic acid in situ detection of human Survival of Motor Neuron (hSMN-1) mRNA in (A) Cervical, (B) Thoracic and (C) Lumbar spinal tissue, 24 hours post intrathecal delivery using liposome formulation 10.
Figure 11B:
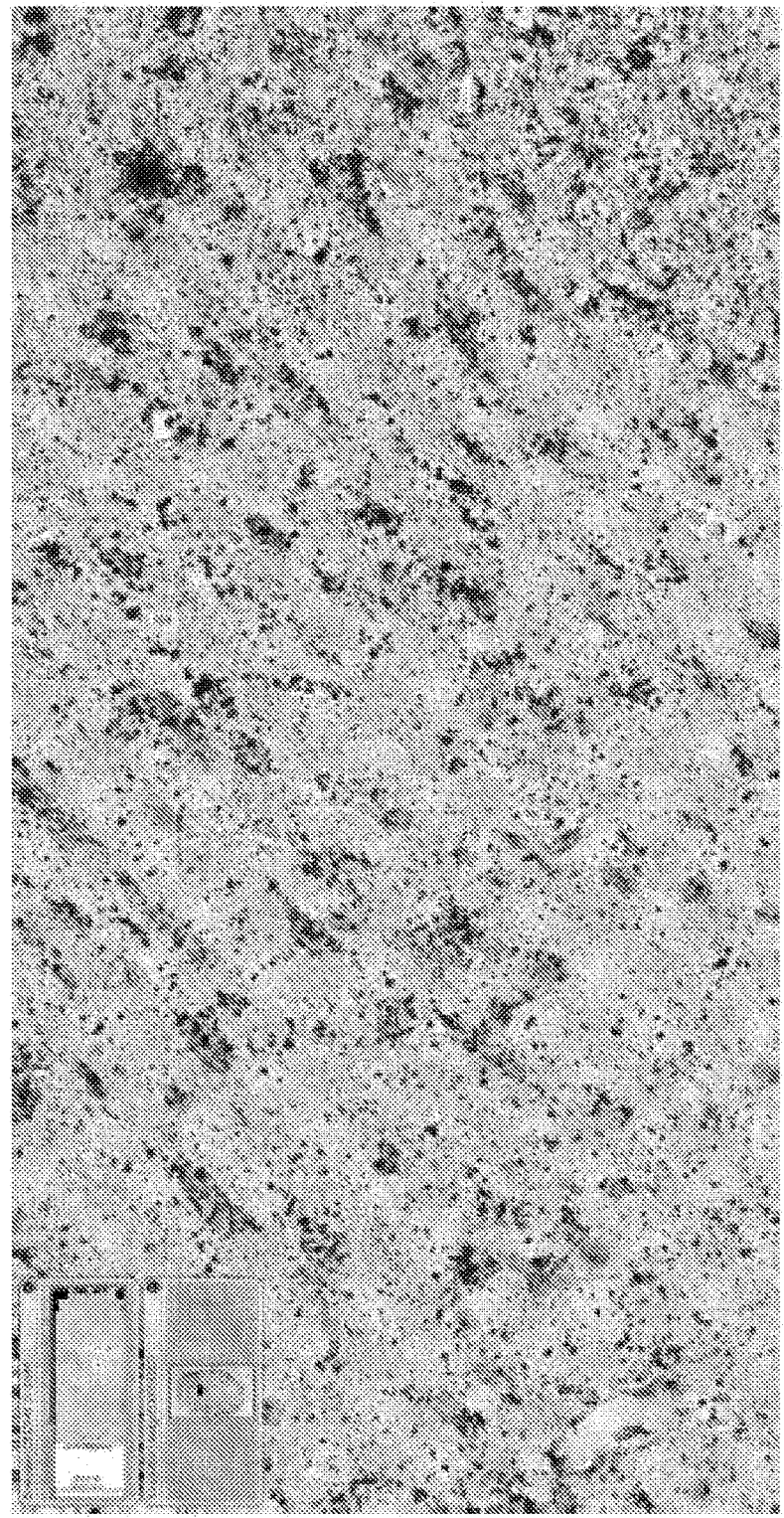
Figure 11C:
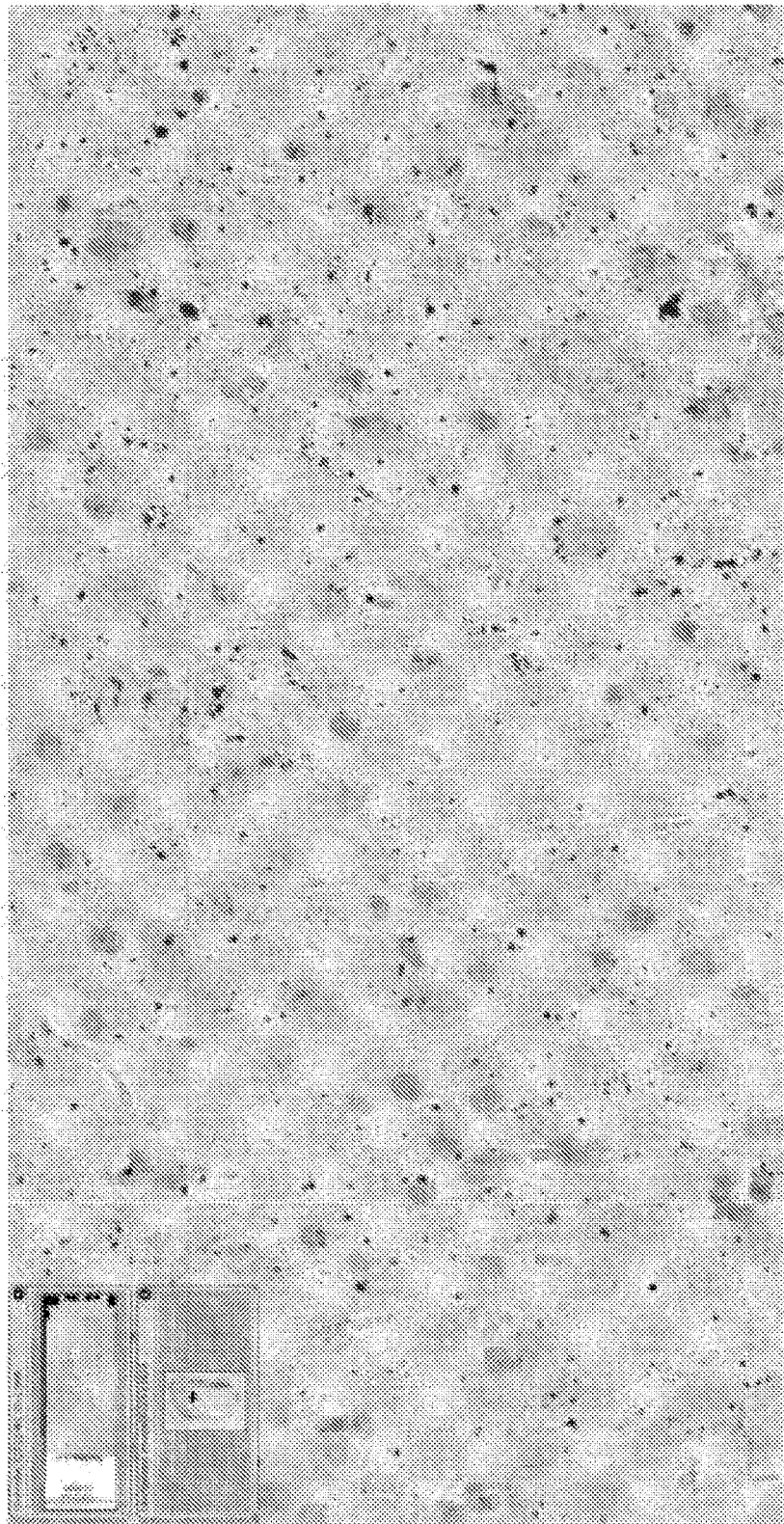
Figure 12A:
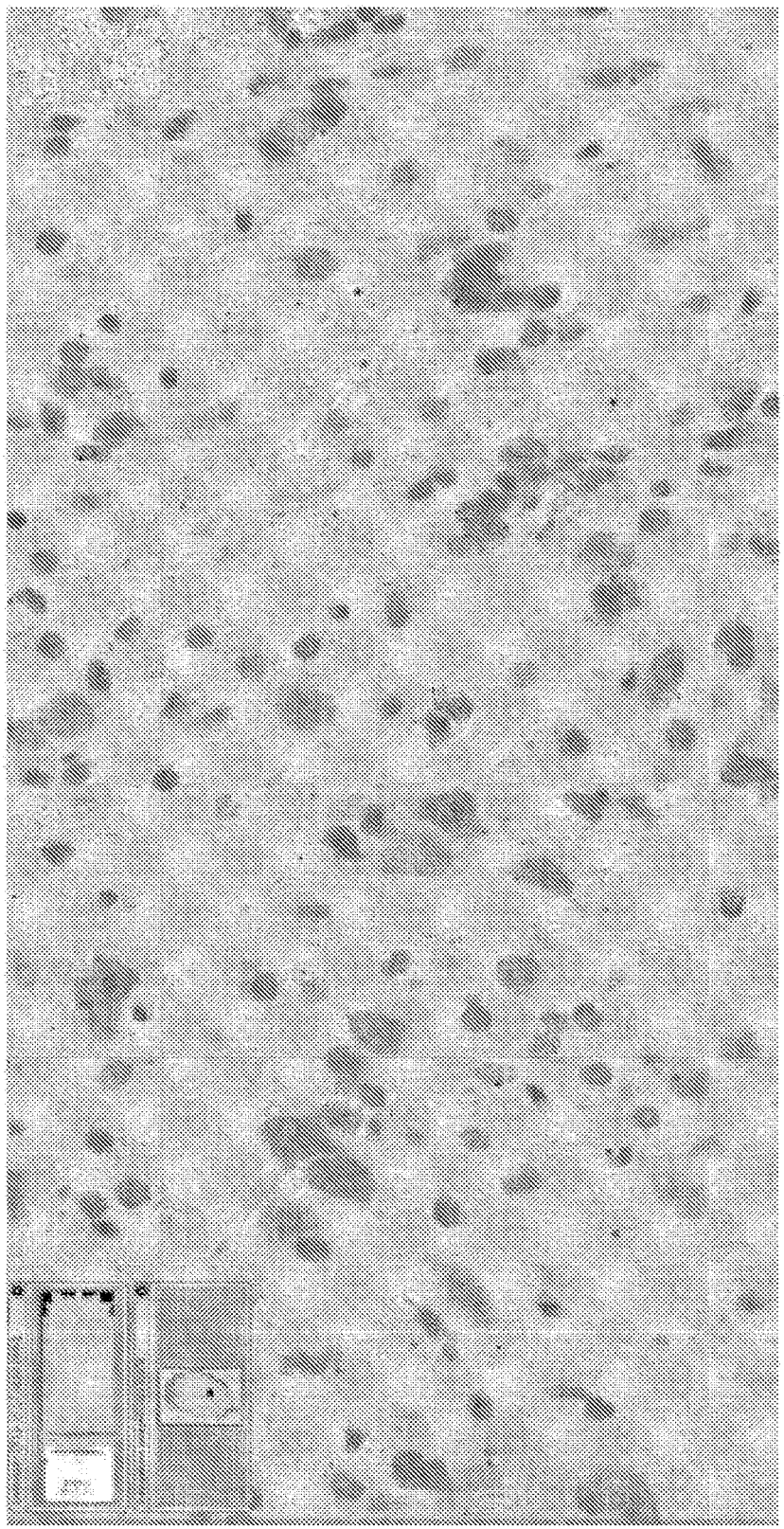
FIG. 12A-C illustrates multiplex nucleic acid in situ detection of human Survival of Motor Neuron (hSMN-1) mRNA in (A) Cervical, (B) Thoracic and (C) Lumbar spinal tissue, 24 hours post intrathecal delivery using liposome formulation 11.
Figure 12B:
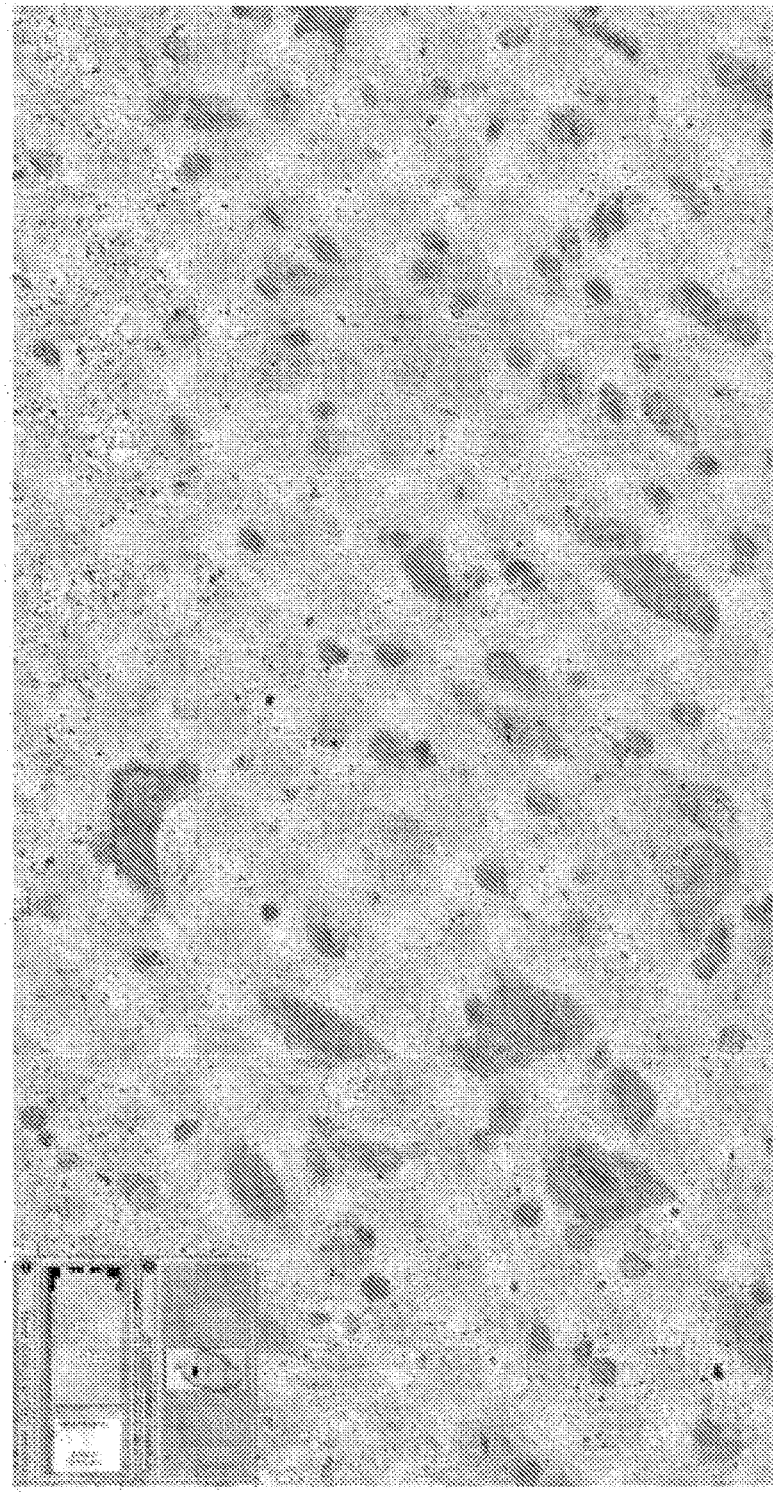
Figure 12C:
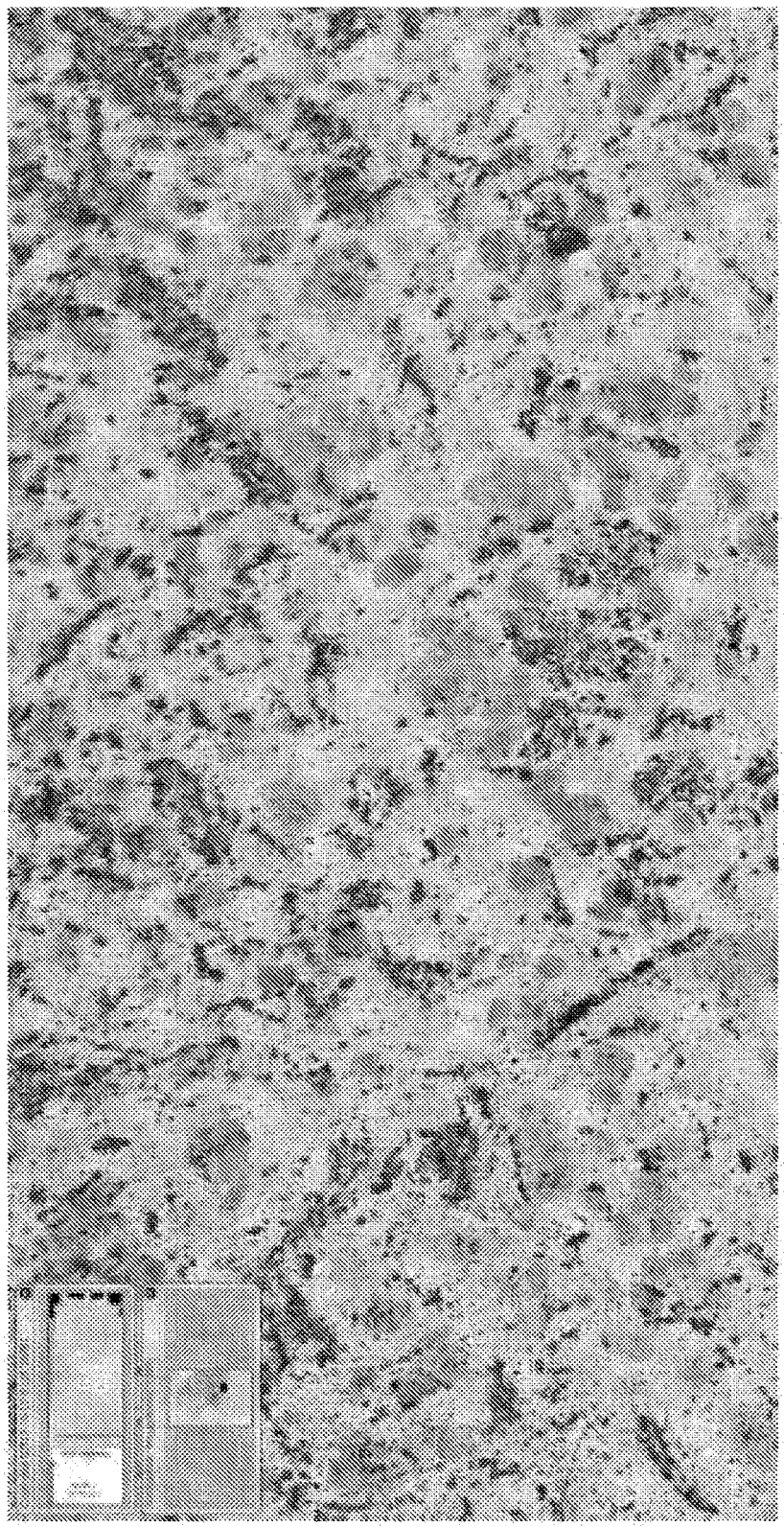
Figure 13B:
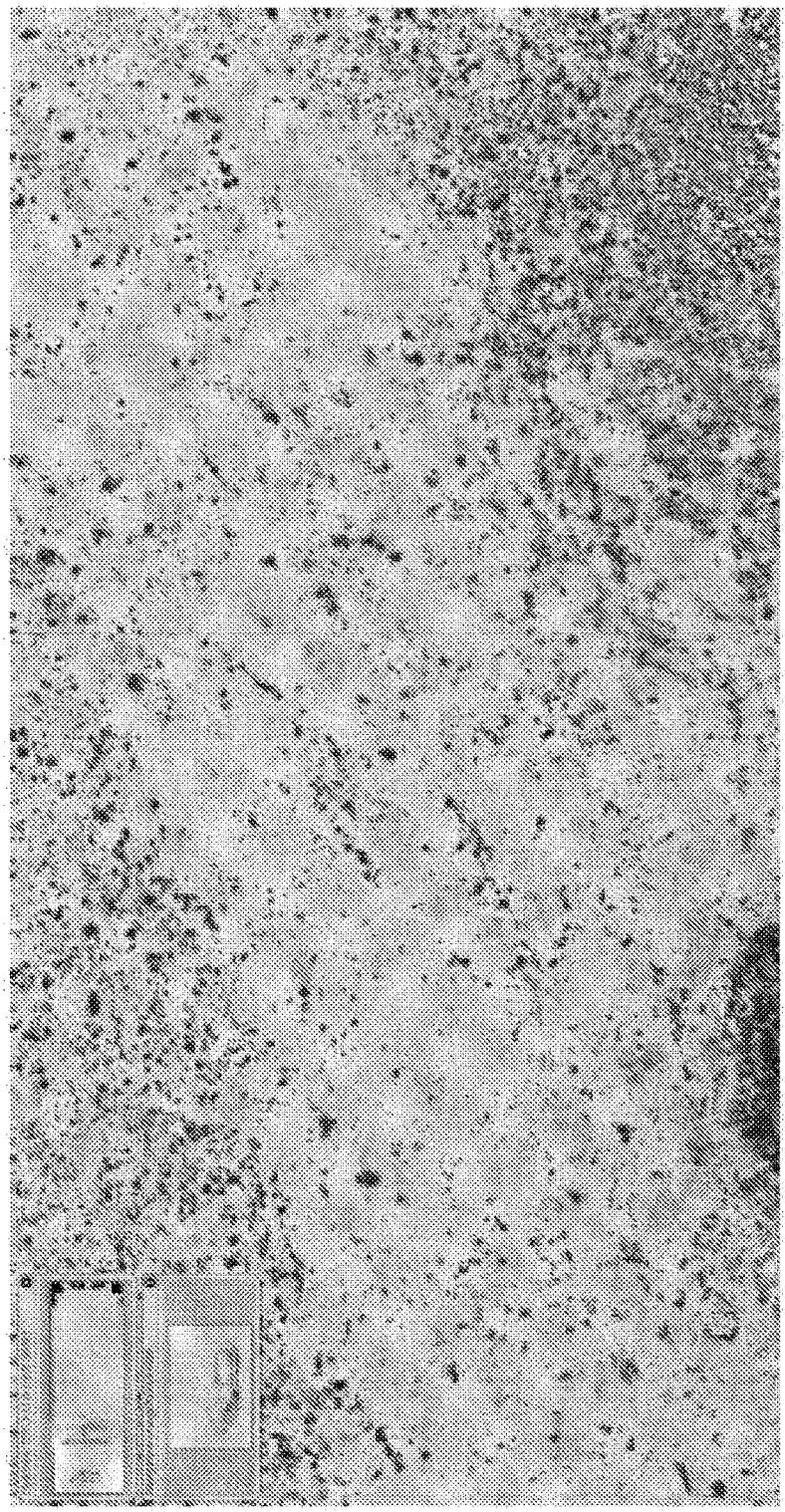
Figure 13C:
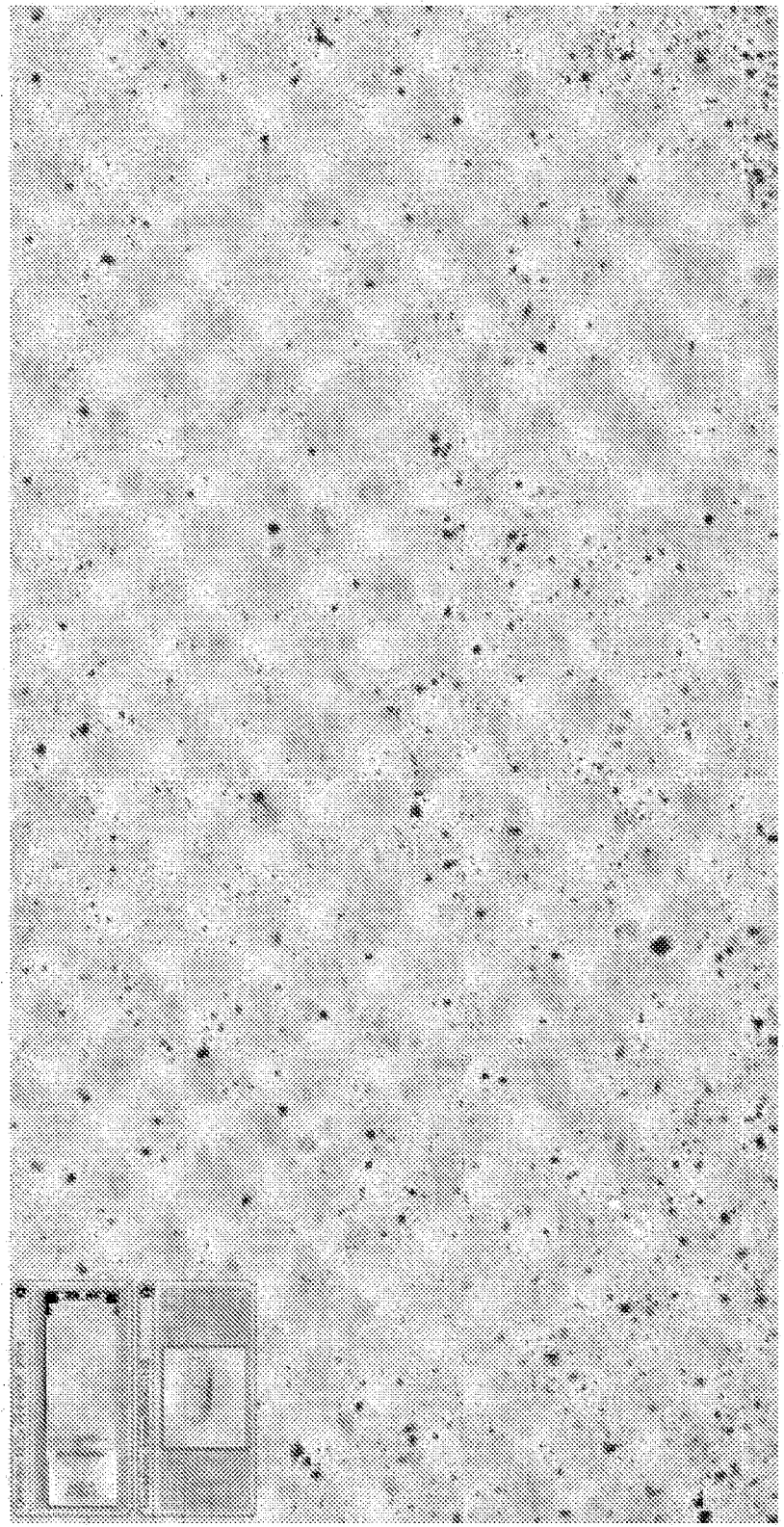
Figure 14A:
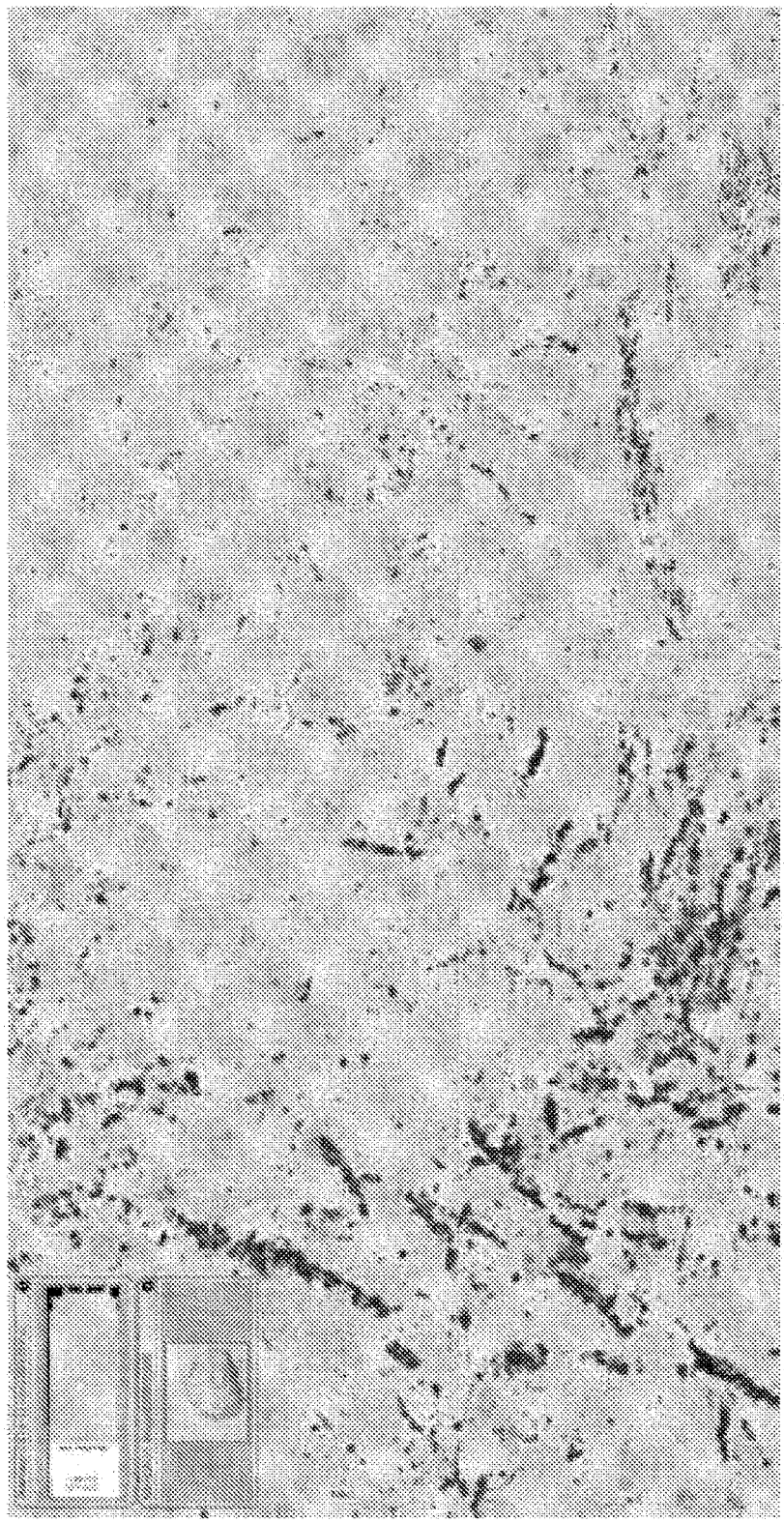
FIG. 14A-C illustrates multiplex nucleic acid in situ detection of human Survival of Motor Neuron (hSMN-1) mRNA in (A) Cervical, (B) Thoracic and (C) Lumbar spinal tissue, 24 hours post intrathecal delivery using liposome formulation 13.
Figure 14B:
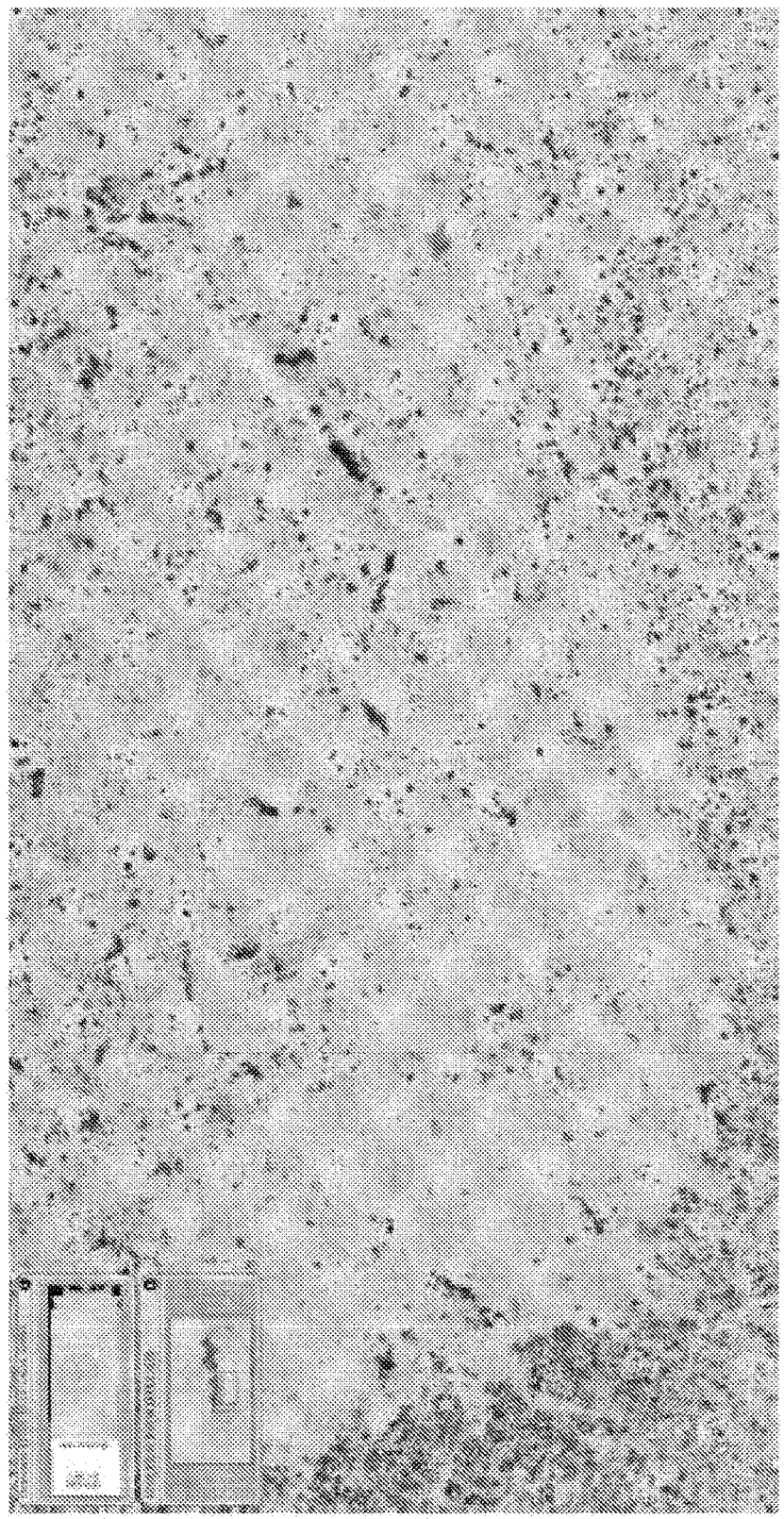
Figure 14C:
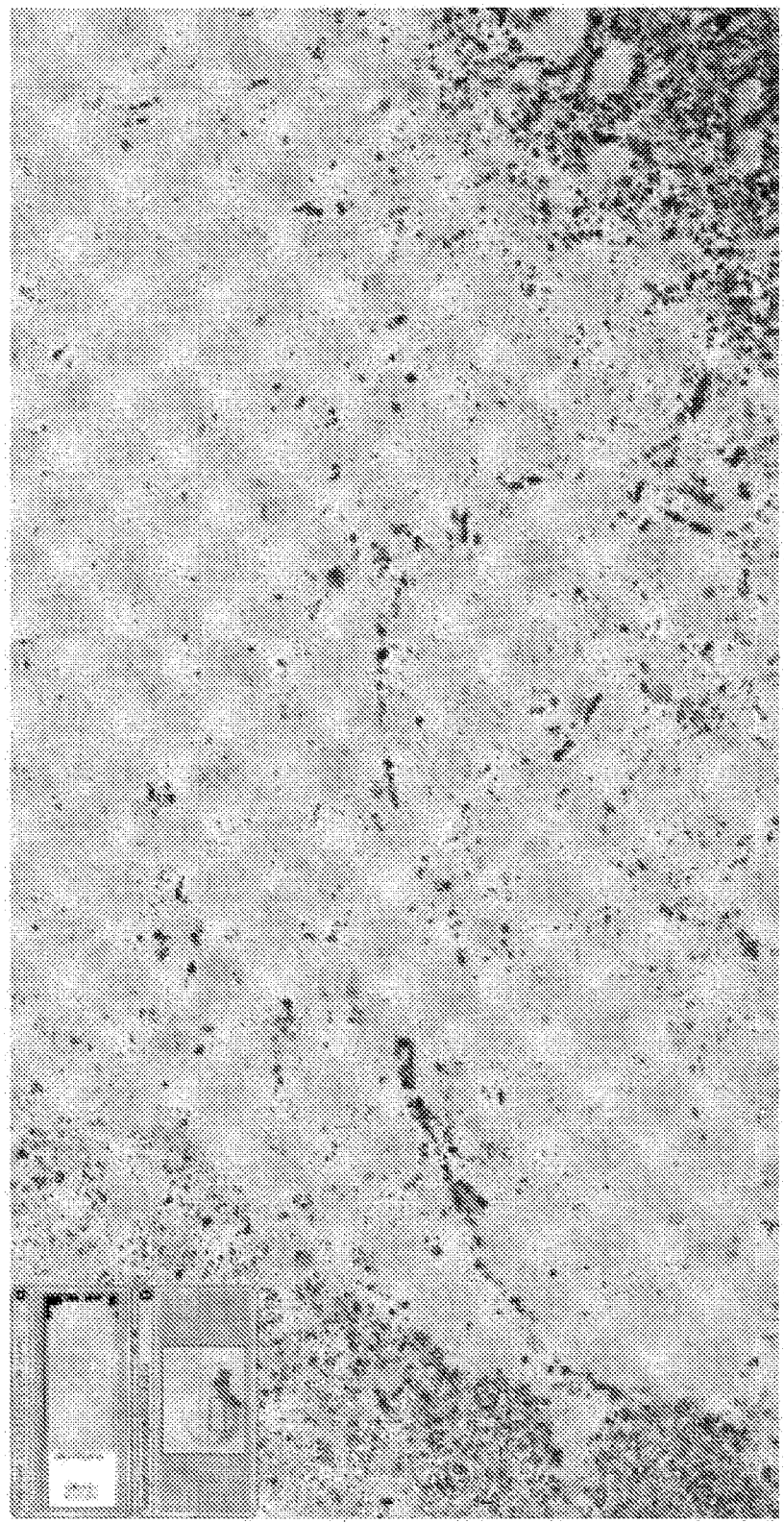

In order for the present invention to be more readily understood, certain terms are first defined below. Additional definitions for the following terms and other terms are set forth throughout the specification.

Alkyl: As used herein, "alkyl" refers to a radical of a straight-chain or branched saturated hydrocarbon group having from 1 to 15 carbon atoms ("$C_{1-15}$ alkyl"). In some embodiments, an alkyl group has 1 to 3 carbon atoms ("$C_{1-3}$ alkyl"). Examples of $C_{1-3}$ alkyl groups include methyl ($C_1$), ethyl ($C_2$), n-propyl ($C_3$), and isopropyl ($C_3$). In some embodiments, an alkyl group has 8 to 12 carbon atoms ("$C_{8-12}$ alkyl"). Examples of $C_{8-12}$ alkyl groups include, without limitation, n-octyl ($C_8$), n-nonyl ($C_9$), n-decyl ($C_{10}$), n-undecyl ($C_{11}$). n-dodecyl ($C_{12}$) and the like. The prefix "n-" (normal) refers to unbranched alkyl groups. For example, n-$C_8$ alkyl refers to —$(CH_2)$—$CH_3$, n-$C_{10}$ alkyl refers to —$(CH_2)_9CH_3$, etc.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%. or less in either direction (greater than or less than) of the stated reference value unless otherwise stated or otherwise evident from the context (except where such number would exceed 100% of a possible value).

Amelioration: As used herein, the term "amelioration" is meant the prevention, reduction or palliation of a state, or improvement of the state of a subject. Amelioration includes, but does not require complete recovery or complete prevention of a disease condition. In some embodiments, amelioration includes increasing levels of relevant protein or its activity that is deficient in relevant disease tissues.

Amino acid: As used herein, term "amino acid," in its broadest sense, refers to any compound and/or substance that can be incorporated into a polypeptide chain. In some embodiments, an amino acid has the general structure $H_2N$—$C(H)(R)$—$COOH$. In some embodiments, an amino acid is a naturally occurring amino acid. In some embodiments, an amino acid is a synthetic amino acid; in some embodiments, an amino acid is a d-amino acid; in some embodiments, an amino acid is an l-amino acid. "Standard amino acid" refers to any of the twenty standard l-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein, the term "animal" refers to any member of the animal kingdom. In some embodiments, "animal" refers to humans, at any stage development. In some embodiments, "animal" refers to non-human animals, at any stage of development. In certain embodiments, the non-human animal is a mammal (e.g., a rodent, a mouse, rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a protein or polypeptide is biologically active, a portion of that protein or polypeptide that shares at least one biological activity of the protein or polypeptide is typically referred to as a "biologically active" portion.

Delivery: The term "delivery", when used in connection with the CNS delivery, encompasses situations in which an mRNA is delivered intracellularly in neurons and the encoded protein is expressed and retained within the neurons, and situations in which an mRNA is delivered intracellularly in neurons and the encoded protein is expressed and secreted, e.g., to the CSF, and taken up by other neurons.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein. In this application, the terms "expression" and "production," and grammatical equivalent, are used inter-changeably.

Fragment: The term "fragment" as used herein refers to polypeptides and is defined as any discrete portion of a given polypeptide that is unique to or characteristic of that polypeptide. The term as used herein also refers to any discrete portion of a given polypeptide that retains at least a fraction of the activity of the full-length polypeptide. Preferably the fraction of activity retried is at least 10% of the activity of the full-length polypeptide. More preferably the fraction of activity retained is at least 20%, 30%, 40%, 50%, 60%, 70%, 80% or 90% of the activity of the full-length polypeptide. More preferably still the fraction of activity retained is at least 95%, 96%, 97%, 98% or 99% of the activity of the full-length polypeptide. Most preferably, the fraction of activity retained is 100% of the activity of the full-length polypeptide. The term as used herein also refers to any portion of a given polypeptide that includes at least an established sequence element found in the full-length polypeptide. Preferably, the sequence element spans at least 4-5, more preferably at least about 10, 15, 20, 25, 30, 35, 40, 45, 50 or more amino acids of the full-length polypeptide.

Functional: As used herein, a "functional" biological molecule is a biological molecule in a form in which it exhibits a property and/or activity by which it is characterized.

Half-life: As used herein, the term "half-life" is the time required for a quantity such as nucleic acid or protein concentration or activity to fall to half of its value as measured at the beginning of a time period.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Intrathecal administration: As used herein, the term "intrathecal administration" or "intrathecal injection" refers to an injection into the spinal canal (intrathecal space surrounding the spinal cord). Various techniques may be used including, without limitation, lateral cerebroventricular injection through a burrhole or cisternal or lumbar puncture or the like. In some embodiments, "intrathecal administration" or "intrathecal delivery" according to the present invention refers to IT administration or delivery via the lumbar area or region, i.e., lumbar IT administration or delivery. As used herein, the term "lumbar region" or "lumbar area" refers to the area between the third and fourth lumbar (lower back) vertebrae and, more inclusively, the L2-S1 region of the spine.

Lower motor neurons: As used herein, the tern "lower motor neuron" refers to the motor neurons connecting the brainstem and spinal cord to muscle fibers. In other words, lower motor neurons bring the nerve impulses from the upper motor neurons out to the muscles. Typically, a lower motor neuron's axon terminates on an effector (muscle). Lower motor neurons include "spinal neuron" and "Anterior horn cells".

Lysosomal enzyme: As used herein, the term "lysosomal enzyme" refers to any enzyme that is capable of reducing accumulated materials in mammalian lysosomes or that can rescue or ameliorate one or more lysosomal storage disease symptoms. Lysosomal enzymes suitable for the invention include both wild-type or modified lysosomal enzymes and can be produced using recombinant and synthetic methods or purified from nature sources. Exemplary lysosomal enzymes are listed in Table 2.

Lysosomal enzyme deficiency: As used herein, "lysosomal enzyme deficiency" refers to a group of genetic disorders that result from deficiency in at least one of the enzymes that are required to break macromolecules (e.g., enzyme substrates) down to peptides, amino acids, monosaccharides, nucleic acids and fatty acids in lysosomes. As a result, individuals suffering from lysosomal enzyme deficiencies have accumulated materials in various tissues (e.g., CNS, liver, spleen, gut, blood vessel walls and other organs).

Lysosomal Storage Disease: As used herein, the term "lysosomal storage disease" refers to any disease resulting from the deficiency of one or more lysosomal enzymes necessary for metabolizing natural macromolecules. These diseases typically result in the accumulation of un-degraded molecules in the lysosomes, resulting in increased numbers of storage granules (also termed storage vesicles). These diseases and various examples are described in more detail below.

messenger RNA (mRNA): As used herein, the term "messenger RNA (mRNA)" refers to a polynucleotide that encodes at least one polypeptide. mRNA as used herein encompasses both modified and unmodified RNA. mRNA may contain one or more coding and non-coding regions. mRNA can be purified from natural sources, produced using recombinant expression systems and optionally purified, chemically synthesized, etc. Where appropriate, e.g., in the case of chemically synthesized molecules, mRNA can comprise nucleoside analogs such as analogs having chemically modified bases or sugars, backbone modifications, etc. An mRNA sequence is presented in the 5' to 3' direction unless otherwise indicated. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine), chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

Nucleic acid. As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA as well as single and/or double-stranded DNA and/or cDNA.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre and post natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Pharmaceutically acceptable salt: Pharmaceutically acceptable salts are well known in the art. For example, S. M. Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulfate, phosphate, nitrate, sulfonate and aryl sulfonate. Further pharmaceutically acceptable salts include salts formed from the quarterniazation of an amine using an appropriate electrophile, e.g., an alkyl halide, to form a quarternized alkylated amino salt.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease of disorder but may or may not display symptoms of the disease or disorder.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treatment: As used herein, the term "treatment" (also "treat" or "treating") refers to any administration of a substance (e.g., provided compositions) that partially or completely alleviates, ameliorates, relives, inhibits, delays onset of, reduces severity of, and/or reduces incidence of one or more symptoms, features, and/or causes of a particular disease, disorder, and/or condition (e.g., influenza). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Upper motor neurons: As used herein, the terms "upper motor neuron" and "corticospinal neuron" are synonymously used to refer to motor neurons that originate in the motor region of the cerebral cortex or the brain stem and carry motor information down to the final common pathway. Typically, upper motor neurons refer to any motor neurons that are not directly responsible for stimulating the target muscle.

DETAILED DESCRIPTION

The present invention provides, among other things, methods and compositions for effective delivery of messenger RNA (mRNA) to the central nervous system (CNS). In particular, the present invention provides methods and compositions for administering intrathecally to a subject in need of delivery a composition comprising an mRNA encoding a protein, encapsulated within a liposome, such that the administering of the composition results in the intracellular delivery of mRNA in neurons in the brain and/or spinal cord. The present invention is particularly useful for the treatment of CNS diseases, disorders or conditions, such as spinal muscular atrophy. As used herein, the term "liposome" refers to any lamellar, multilamellar, or solid lipid nanoparticle vesicle. Typically, a liposome as used herein can be formed by mixing one or :more lipids or by mixing one or more lipids and polymer(s). Thus, the term "liposome" as used herein encompasses both lipid and polymer based nanoparticles. In some embodiments, a liposome suitable for the present invention contains cationic or non-cationic lipid(s), cholesterol-based lipid(s) and PEG-modified lipid(s).

Various aspects of the invention are described in detail in the following sections. The use of sections is not meant to limit the invention. Each section can apply to any aspect of the invention. In this application, the use of "or" means "and/or" unless stated otherwise.

mRNA Associated with CNS Diseases, Disorders or Conditions

The present invention can be used to deliver any mRNA to the central nervous system. In particular, the present invention is useful to deliver mRNA that encodes a protein associated with or implicated in a CNS disease, disorder or condition. As used herein, a "CNS disease, disorder or condition" refers to a disease, disorder or condition affecting one or more neuronal functions of the central nervous system (i.e., the brain and/or spinal cord). In some embodiments, a CNS disease, disorder or condition may be caused by a protein deficiency or dysfunction in neurons of the CNS (i.e., the brain and/or spinal cord).

Exemplary CNS diseases, disorders or conditions include, but are not limited to, Acid Lipase Disease, Acid Maltase Deficiency, Acquired Epileptiform Aphasia, Acute Disseminated Encephalomyelitis, ADHD, Adie's Pupil, Adie's Syndrome, Adrenoleukodystrophy, Agnosia, Aicardi Syndrome, Aicardi-Goutieres Syndrome Disorder, Alexander Disease, Alpers' Disease, Alternating Hemiplegia, Alzheimer's Disease, Amyotrophic Lateral Sclerosis (ALS), Anencephaly, Aneurysm, Angelman Syndrome, Angiomatosis, Anoxia, Antiphospholipid Syndrome, Aphasia, Apraxia, Arachnoiditis, Arnold-Chiari Malformation, Asperger Syndrome, Ataxia, Ataxia Telangiectasia, Ataxias and Cerebellar or Spinocerebellar Degeneration, Attention Deficit-Hyperactivity Disorder, Autism, Autonomic Dysfunction, Barth Syndrome, Batten Disease, Becker's Myotonia, Bechcet's Disease, Bell's Palsy, Bernhardt-Roth Syndrome, Binswanger's Disease, Bloch-Sulzberger Syndrome, Bradbury-Eggleston Syndrome, Brown-Sequard Syndrome, Bulbospinal Muscular Atrophy, CADASIL, Canavan Disease, Causalgia, Cavernomas, Cavernous Angioma, Central Cervical Cord Syndrome, Central Cord Syndrome, Central Pontine Myelinolysis, Ceramidate Deficiency, Cerebellar Degeneration, Cerebellar Hypoplasis, Cerebral Beriberi, Cerebral Gigantism, Cerebral Palsy, Cerebro-Oculo-Facio-Skeletal Syndrome (COFS), Cholesterol Ester Storage Disease, Chorea, Choreoacanthocytosis, Chronic Inflammatory Demyelinating Polyneuropathy (CIDP), Chronic Orthostatic Intolerance, Cockayne Syndrome Type II, Coffin Lowry Syndrome, Colpocephaly, Congenital Myasthenia, Corticobasal Degeneration, Cranial Arteritis, Cree encephalitis, Creutzfeldt-Jakob Disease, Cushing's Syndrome, Cytomegaic Inclusion Body Disease, Dancing Eyes-Dancing Feet Syndrome, Dandy-Walker Syndrome, Dawson Disease, De Morsier's Syndrome, Dejeriine-Klumpke Palsy, Dentate Cerebellar Ataxia, Dentatorubral Atrophy, Dematomyositis, Developmental Dyspraxia, Devic's Syndrome, Diffuse Sclerosis, Dravet Syndrome, Dysautonomia, Dysgraphia, Dyslexia, Dysphagis, Dyspraxia, Dyssynergia Cerebellaris Myoclonica, Dyssynergia Cerebellaris Progressiva, Fabry Disease, Fahr's Syndrome, Familial Dysautonimia, Familial Hemangioma, Familial Idiopathic Basal Ganglia Calcification, Familial Periodic Paralyses, Familial Spastic Paralysis, Farber's Disease, Fibromuscular Dysplasis, Fisher Syndrome, Floppy Infant Syndrome, Friedreich's Ataxia, Gaucher Disease, Generalized Gangliosidoses, Gerstmann's Syndrome, Gerstmann-Straussler-Scheinker Disease, Giant Axonal Neuropathy, Giant Cell Arteritis, Giant Cell Inclusion Disease, Globoid Cell Leukodystrophy, Glossopharyngeal Neuralgia, Glycogen Storage Disease, Guillain-Barré Syndrome, Hallervorden-Spatz Disease, Hemicrania Continua, Hemiplegia Alterans, Hereditary Spastic Paraplegia, Heredopathia Atactica Polyneuritiformis, Holmes-Adie syndrome, Holoprosencephaly, Hughes Syndrome, Hunting-ton's Disease, Hydranencephaly, Hydromyelia, Hypercortisolsim, Immune-Mediated, Encephalomyelitis, Inclusion Body Myositis, Incontinentia Pigmenti, Infantile Hypotonia, Infantile Neuroaxonal Dystrophy, Acid Storage Disease, Iniencephaly, Isaac's Syndrome, Joubert Syndrome, Kearns-Sayre Syndrome, Kennedy's Disease, Kinsbourne syndrome, Kleine-Levin Syndrome, Klippel-Feil Syndrome, Klippel-Trenaunay Syndrome (KTS), Klüver-Bucy Syndrome, Korsakoff's Amnesic Syndrome, Krabbe Disease, Kugelberg-Welander Disease, Lamber-Eaton Myasthenic Syndrome, Landau-Kleffner Syndrome, Lateral, Femoral Cutaneous Nerve Entrapment, Lateral Medullary Syndrome, Leigh'Disease, Lennox-Gastaut Syndrome, Lesch-Nyhan Syndrome, Levine-Critchely Syndrome, Lewy Body Dementia, Lipoid Proteinosis, Lissencephaly, Locked-In Syndrome, Lou Gehrig's Disease, Lupus-Neurological Sequelae, Lyme Disease, Machado-Joseph Disease, Macrencephaly, Melkerssoon-Rosenthal Syndrome, Menkes Disease, Meralgia Paresthetica, Metachromatic Leukodystrophy, Microcephaly, Miller Fisher Syndrome, Moebius Syndrom, Multiple Sclerosis, Muscular Dystrophy, Myasthenia Gravis, Myelinoclastic Diffuse Sclerosis, Narclepsy, Neuroacanthocytosis, Neurofibrmatosis, Neuroleptic Malignant Syndrome, Neurosarcoidosis, Niemann-Pick Disease, Ohtahara Syndrome, Olivopontocerebellar Atrophy, Opsoclonus Myoclonnus, O'Sullivan-McLeod Syndrome, Pantothenate Kinase-Associated Neurodegeneration, Paraneoplastic Syndromes, Paresthesia, Parkinson's Disease, Paroxysmal Choreoathetosis, Paroxysmal Hemicrania, Parry-Romber, Pelizaeus-Merzbacher Disease, Pena Shokeir II Syndrome, Periventricular Leukomalacia, Phytanic Acid Storage Disease, Pick's Disease, Piriformis Syndrome, Polymyositis, Pompe Disease, Post-Polio Syndrom, Primary Dentatum Atrophy, Primary Lateral Sclerosis, Primary Progressive Aphasia, Prion Diseases, Progressive Hemifacial Atrophy, Progressive Locomotor Ataxia, Progressive Multifocal Leukoencephalophathy, Progressive Sclerosing Poliodystrophy, Progressive Supranuclear Palsy, Prosopagnosia, Ramsay Hunt Syndrome I, Ramsay Hunt Syndrom II, Rasmussen's Encephalitis, Refsum Disease, Rett Syndrome, Reye's Syndrome, Riley-Day Syndrome, Sandhoff Disease, Schilder's Disease, Seitelberger Disease, Severe Myoclonic Epilepsy of Infancy (SMEI), Shy-Drager Syndrome, Sjögreb's Syndrome, Spasticity, Spina Bifida, Spinal Muscular Atrophy, Spinocerebellar Atrophy, Spinocerebellar Degeneration, Steele-Richardson-Olszewski Syndrome, Striatonigral Degeneration, Sturge-Weber Syndrome, Tardive Dyskinesia, Tay-Sachs Disease, Thoracic Outlet Syndrome, Thyrotoxic Myopathy, Tic Douloureux, Todd's Paralysis, Trigeminal Neuralgia, Tropical Spastic Paraparesis, Troyer Syndrome, Von Economo's Disease, Von Hippel-Lindau Disease (VHL), Von Recklinghausen's Disease, Wallenberg's Syndrome, Werdnig-Hoffman Disease, Wernicke-Korsakoff Syndrome, West Syndrome, Whipple's Disease, Williams Syndrome, Wilson Disease, Wolman's Disease, X-Linked Spinal and Bulbar Muscular Atrophy and Zellweger Syndrome.

Motor Neuron Diseases

In some embodiments, a CNS disease, disorder or condition is a disease, disorder condition that affects one or more functions of motor neuron., which is also referred to as a motor neuron disease. In some embodiments, a motor neuron disease may be caused by a protein deficiency or dysfunction in motor neurons of the CNS (i.e., the brain and/or spinal cord). As used herein, the term "motor neurons" refer to those neurons that control voluntary muscle activity. Typically, motor neurons include upper motor neurons and lower motor neurons. As used herein, the term "upper motor neuron" refers to motor neurons that originate in the motor region of the cerebral cortex or the brain stem and carry motor information down to the final common pathway. Upper motor neurons also referred to as "corticospinal neurons". Typically, upper motor neurons refer to any motor neurons that are not directly responsible for stimulating the target muscle. As used herein, the term "lower motor neuron" refers to the motor neurons connecting the brainstem and spinal cord to muscle fibers. In other words, lower motor neurons bring the nerve impulses from the upper motor neurons out to the muscles. Typically, a lower motor neuron's axon terminates on an effector (muscle). Lower motor neurons include "spinal neuron" and "Anterior horn cells".

Exemplary motor neuron diseases, disorders or conditions include, but are limited to, Amyotrophic Lateral Sclerosis (ALS), Primary Lateral Sclerosis (PLS), Pseudobulbar Pasly, Hereditary Spastic Paraplegia, Progressive Muscular Atrophy (PMA), Progressive Bulbar Palsy (PBP), Distal Hereditary Motor Neuropathies, and Spinal Muscular Atrophies.

In some embodiments, a motor neuron disease, disorder or condition is a form of spinal muscular atrophy. The family of spinal muscular atrophies are a genetically and clinically heterogeneous group of rare debilitating disorders characterized by degeneration of the lower motor neurons. Degeneration of the cells within the lower motor neurons, which are also known as the anterior horn cells of the spinal cord, leads to a loss of motor function resulting in atrophy and excessive wasting of various muscle groups within the body. Diseases that comprise the family can be divided into Proximal, Distal, Autosomal Recessive Proximal and Localized spinal muscular atrophies. However, given that protein deficiencies are the major cause of the various forms of spinal muscular atrophy, each disease member is usually classified according to the gene associated with the condition. Table 1 below describes six major groups of spinal muscular atrophies.

TABLE 1

Representative Groups of Spinal Muscular Atrophies

| Group | Name | Gene | Inheritance |
|---|---|---|---|
| SMA | Spinal muscular atrophy (SMA) | SMN-1 | Autosomal Recessive |
| XLSMA | X-linked spinal muscular atrophy type-1 (SMAX1) | NR3C4 | X-Linked Reccessive |
|  | X-linked spinal muscular atrophy type-2 (SMAX2) | UBA1 | X-Linked Reccessive |
|  | X-linked spinal muscular atrophy type-3 (SMAX3) | ATP7A | X-Linked Reccessive |
| DSMA | Distal spinal muscular atrophy type-1 (DSMA1) | IGHMBP2 | Autosomal Recessive |
|  | Distal spinal muscular atrophy type-2 (DSMA2) |  | Autosomal Recessive |
|  | Distal spinal muscular atrophy type-3 (DSMA3) |  | Autosomal Recessive |
|  | Distal spinal muscular atrophy type-4 (DSMA4) | PLEKHG5 | Autosomal Recessive |
|  | Distal spinal muscular atrophy type-5 (DSMA5) | DNAJB2 | Autosomal Recessive |
|  | Distal spinal muscular atro hy VA (DSMA VA) | GARS | Autosomal Dominant |
|  | Distal spinal muscular atrophy VB (DSMA VA) | REEP1 | Autosomal Dominant |
|  | Distal spinal muscular atrophy with vocal cord paralysis | SLC5A7 | Autosomal Dominant |
| ADSMA | Autosomal dominant distal spinal muscular atrophy | HSPB8 | Autosomal Dominant |
|  | Autosomal dominant juvenile distal spinal muscular atrophy |  | Autosomal Dominant |

TABLE 1-continued

Representative Groups of Spinal Muscular Atrophies

| Group | Name | Gene | Inheritance |
|---|---|---|---|
| NTMA | Congential distal spinal muscular atrophy | TRPV4 | Autosomal Dominant |
|  | Scapuloperoneal spinal muscular atrophy (SPSMA) | TRPV4 | Autosomal Dominant or X-linked Dominant |
|  | Juvenile segmental spinal muscular atrophy (JSSMA) |  |  |
|  | Finkel-type proximal spinal muscular atrophy (SMA-FK) | VAPB | Autosomal Dominant |
|  | Jokela-type spinal muscular atrophy (SMA-J) |  | Autosomal Dominant |
|  | Spinal muscular atrophy with lower extremity predominance (SMA-LED) | DYNC1H1 | Autosomal Dominant |
|  | Spinal muscular atrophy with progressive myoclonic epilepsy (SMA-PME) | ASAH1 | Autosomal Recessive |
|  | Spinal muscular atrophy with congenital bone fractures (SMA-CBF) |  | Autosomal Recessive |
| PCH | Spinal muscular atrophy with pontocerebellar hypoplasis (SMA-PCH) | VRK1 | Autosomal Dominant |
| MMA | Juvenile asymmetric segmental spinal muscular atrophy (JASSMA) |  |  |

Diseases with a CNS Component

In some embodiments, a CNS disease, disorder or condition is a disease with a CNS component. Typically, a disease with a CNS component is caused by a protein deficiency in one or more tissues, including both CNS and peripheral tissues, of the body, resulting in one or more CNS etiology and/or symptoms. For example, in some embodiments, a protein deficiency may result in the excess accumulation of an intracellular and/or extracellular component such as glucosaminoglycans (GAGs), lipids, plaque (i.e.; Beta-amyloid) or protein. Thus, in some embodiments, a disease with a CNS component is a lysosomal storage disease caused by a deficiency in a lysosomal enzyme, which results in the excess accumulation of glucosaminoglycans (GAGs) in both the CNS and peripheral tissues.

In some embodiments, lysosomal storage diseases having CNS etiology and/or symptoms include, but are not limited to, aspartylglucosaminuria, cholesterol ester storage disease, Wolman disease, cystinosis, Danon disease, Fabry disease, Farber lipogranulomatosis, Farber disease, fucostdosis, galactosialidosis types I/II, Gaucher disease types I/II/III, globoid cell leukodystrophy, Krabbe disease, glycogen storage disease II, Pompe disease, GM1-gangliosidosis types I/II/III, GM2-gangliosidosis type I, Tay Sachs disease, GM2-gangliosidosis type II, Sandhoff disease, GM2-gangliosiodosis, α-mannosidosis types I/II, beta-mannosidosis, metachromatic leukodystrophy, mucolipidosis type I, sialidosis types I/II, mucolipidosis types II/III, I-cell disease, mucolipidosis type IIIC pseudo-Hurler polydystrophy, mucopolysaccharidosis type I, mucopolysaccharidosis type II, mucopolysaccharidosis type IIIA, Sanfilippo syndrome, mucopolysaccharidosis type IIIB, mucopolysaccharidosis type IIIC, mucopolysaccharidosis type IIID, mucopolysaccharidosis type IVA, Morquio syndrome, mucopolysaccharidosis type IVB, mucopolysaccharidosis type VI, mucopolysaccharidosis type VII, Sly syndrome, mucopolysaccharidosis type IX, multiple sulfatase deficiency, neuronal ceroid lipofuscinosis, CLN1 Batten disease, CLN2 Batten disease, Niemann-Pick disease types A/B, Niemann-Pick disease type C1, Niemann-Pick disease type C2, pycnodysostosis, Schindler disease types I/II, Gaucherr disease and sialic acid storage disease.

A detailed review of the genetic etiology, clinical manifestations, and molecular biology of the lysosomal storage diseases are detailed in Scriver et al., eds., The Metabolic and Molecular Basis of Inherited Disease, 7.sup.th Ed., Vol. II, McGraw Hill, (1995). Thus, the enzymes deficient in the above diseases are known to those of skill in the art, some of these are exemplified in Table 2 below:

TABLE 2

Lysosomal Diseases and Enzyme Deficiency

| Disease Name | Enzyme Deficiency | Substance Stored |
| --- | --- | --- |
| Pompe Disease | Acid-α1, 4-Glucosidase | Glycogen α-1-4 linked Oligosaccharides |
| GM1 Gangliodsidosis | β-Galactosidase | $GM_1$ Gangliosides |
| Tay-Sachs Disease | β-Hexosaminidase A | $GM_2$ Ganglioside |
| GM2 Gangliosidosis: AB Variant | $GM_2$ Activator Protein | $GM_2$ Ganglioside |
| Sandhoff Disease | β-Hexosaminidase A&B | $GM_2$ Ganglioside |
| Fabry Disease | α-Galactosidase A | Globosides |
| Gaucher Disease | Glucocerebrosidase | Glucosylceramide |
| Metachromatic Leukodystrophy | Arylsulfatase A | Sulphatides |
| Krabbe Disease | Galactosylceramidase | Galactocerebroside |
| Niemann Pick, Types A & B | Acid Sphingomyelinase | Sphingomyelin |
| Niemann-Pick, Type C | Cholesterol Esterification Defect | Sphingomyelin |
| Niemann-Pick, Type D | Unknown | Sphingomyelin |
| Farber Disease | Acid Ceramidase | Ceramide |
| Wolman Disease | Acid Lipase | Cholesteryl Esters |
| Hurler Syndrome (MPS IH) | α-L-Iduronidase | Heparan & Dermatan Sulfates |
| Scheie Syndrome (MPS IS) | α-L-Iduronidase | Heparan & Dermatan, Sulfates |
| Hurler-Scheie (MPS IH/S) | α-L-Iduronidase | Heparan & Dermatan Sulfates |
| Hunter Syndrome (MPS II) | Iduronate Sulfatase | Heparan & Dermatan Sulfates |
| Sanfilippo A (MPS IIIA) | Heparan N-Sulfatase | Heparan Sulfate |
| Sanfilippo B (MPS IIIB) | α-N-Acetylglucosaminidase | Heparan Sulfate |
| Sanfilippo C (MPS IIIC) | Acetyl COA-Glucosaminide Acetyltransferase | Heparan Sulfate |
| Sanfilippo D (MPS IIID) | N-Acetylglucosamine-6-Sulfatase | Heparan Sulfate |
| Morquio B (MPS IVB) | β-Galactosidase | Keratan Sulfate |
| Maroteaux-Lamy (MPS VI) | Arylsulfatase B | Dermatan Sulfate |
| Sly Syndrome (MPS VID) | β-Glucuronidase | |
| α-Mannosidosis | α-Mannosidase | Mannose/Oligosaccharides |
| β-Mannosidosis | β-Mannosidase | Mannose/Oligosaccharides |
| Fucosidosis | α-L-Fucosidase | Fucosyl/Oligosaccharides |
| Aspartylglucosaminuria | N-Aspartyl-β-Glucosaminidase | Aspartylglucosamine Asparagines |
| Sialidosis (Mocolipidosis I) | α-Neuraminidase | Sialyloligosaccharides |
| Galactosialidosis (Goldberg Syndrome) | Lysosomal Protective Protein Deficiency | Sialyloligosaccharides |
| Schindler Disease | α-N-Acetyl-Galactosaminidase | |

TABLE 2-continued

Lysosomal Diseases and Enzyme Deficiency

| Disease Name | Enzyme Deficiency | Substance Stored |
| --- | --- | --- |
| Mucolipidosis II (I-Cell Disease) | N-Acetylglucosamine-1-Phosphotransferase | Heparan Sulfate |
| Mucolipidosis III (Pseudo-Hurler Polydystrophy) | Same as ML II | |
| Cystinosis | Cystine Transport Protein | Free Cystine |
| Salla Disease | Sialic Acid Transport Protein | Free Sialic Acid and Glucuronic Acid |
| Infantile Sialic Acid Storage Disease | Sialic Acid Transport Protein | Free Sialic Acid and Glucuronic Acid |
| Infantile Neuronal Ceroid Lipofuscinosis | Palmitoyl-Protein Thioesterase | Lipofuscins |
| Mucolipidosis IV | Unknown | Gangliosides & Hyaluronic Acid |
| Prosaposin | Saposins A, B, C or D | |

In various embodiments, the present invention may be used to deliver an mRNA encoding a protein that is deficient in any of the CNS diseases, disorders or conditions described herein. In some embodiments, the present invention may be used to deliver an mRNA encoding a protein that is deficient in a motor neuron disease, for example, a motor neuron disease shown in Table 1. In particular embodiments, the present invention may be used to deliver an mRNA encoding a protein that is deficient in Spinal muscular atrophy (SMA), e.g., SMN1, which is described in detail below. In some embodiments, the present invention may be used to deliver an mRNA encoding a lysosomal enzyme that is deficient in a lysosomal storage disease with a CNS component. In some embodiments, the present invention may be used to deliver an mRNA encoding a lysosomal enzyme selected from Table 2. In some embodiments, an mRNA suitable for the invention may encoded a wild-type or naturally occurring amino acid sequence. In some embodiments, an mRNA suitable for the invention may be a wild-type or naturally occurring sequence. In some embodiments, an mRNA suitable for the invention may be a codon-optimized sequence. In some embodiments, an mRNA suitable for the invention may encode an amino acid sequence having substantial homology or identify to the wild-type or naturally-occurring amino acid protein sequence (e.g., having at least 50%, 55%, 60%, 65%, 70%, 75%, 80%, 85%, 90%, 95%, 98% sequence identity to the wild-type or naturally-occurring sequence).

Survival of Motor Neuron

In some embodiments, inventive methods and compositions provided by the present invention are used to deliver an mRNA encoding a Survival of Motor Neuron protein to the CNS for treatment of spinal muscular atrophy (SMA).

A suitable SMN mRNA encodes any full length, fragment or portion of a SMN protein which can be substituted for naturally-occurring SMN protein activity or rescue one or more phenotypes or symptoms associated with spinal muscular atrophy. The mRNA sequence for human Survival of Motor Neuron-1 (hSMN-1) and corresponding amino acid sequence of a typical wild-type or naturally occurring hSMN-1 protein are shown in Table 3.

TABLE 3

| Human SMN-1 | |
|---|---|
| Human SMN-1 (mRNA) | GGGGACCCGCGGGUUUGCUAUGGCGAUGAGCAGCGGCGGCAGUGGUGGCGGCGU<br>CCCGGAGCAGGAGGAUUCCGUGCUGUUCCGGCGCGGCACAGGCCAGAGCGAUGA<br>UUCAGACAUUUGGGAUGAUACAGCACUGAUAAAAGCAUAUGAUAAAGCUGUGGC<br>UUCAUUUAAGCAUGCUCUAAAGAAUGGUGACAUUUGUGAAACUUCGGGUAAACC<br>AAAAACCACACCUAAAAGAAAACCUGCUAAGAAGAAUAAAAGCCAAAAGAAGAA<br>UACUGCAGCUUCCUUACAACAGUGGAAAGUUGGGGACAAAUGUUCUGCCAUUUG<br>GUCAGAAGACGGUUGCAUUUACCCAGCUACCAUUGCUUCAAUUGAUUUUAAGAG<br>AGAAACCUGUGUUGUGGUUUACACUGGAUAUGGAAAUAGAGAGGAGCAAAAUCU<br>GUCCGAUCUACUUUCCCCAAUCUGUGAAGUAGCUAAUAAUAUAGAACAAAAUGC<br>UCAAGAGAAUGAAAAUGAAAGCCAAGUUUCAACAGAUGAAAGUGAGAACUCCAG<br>GUCUCCUGGAAAUAAAUCAGAUAACAUCAAGCCCAAAUCUGCUCCAUGGAACUC<br>UUUUUCUCCCUCCACCACCCCCAUGCCAGGGCCAAGACUGGGACCAGGAAAGCC<br>AGGUCUAAAAUUCAUGGCCCACCACCGCCACCGCCACCACCACCACCCCACUU<br>ACUAUCAUGCUGGCUGGCUCCAUUUCCUUCUGGACCACCAAUAAUUCCCCCACC<br>ACCUCCCAUAUGUCCAGAUUCUCUUGAUGAUGCUGAUGCUUUGGGAAGUAUGUU<br>AAUUUCAUGGUACAUGAGUGGCUAUCAUACUGGCUAUUAUAUGGGUUUCAGACA<br>AAAUCAAAAGAAGGAAGGUGCUCACAUUCCUUAAAUUAAGGAGAAAUGCUGGC<br>AUAGAGCAGCACUAAAUGACACCACUAAAGAAACGAUCAGACAGAUCUGGAAUG<br>UGAAGCGUUAUAGAAGAUAACUGGCCUCAUUUCUUCAAAAUAUCAAGUGUUGGG<br>AAAGAAAAAAGGAAGUGGAAUGGGGUAACUCUUCUUGAUUAAAAGUUAUGUAAUA<br>ACCAAAUGCAAUGUGAAAUAUUUUACUGGACUCUAUUUUGAAAAACCAUCUGUA<br>AAAGACUGGGGUGGGGUGGGAGGCCAGCACGGUGGUGAGGCAGUUGAGAAAAU<br>UUGAAUGUGGAUUAGAUUUUGAAUGAUAUUGGAUAAUUAUUGGUAAUUUUUAUG<br>AGCUGUGAGAAGGGUGUUGUAGUUUAUAAAAGACUGUCUUAAUUUGCUACUUA<br>AGCAUUUAGGAAUGAAGUGUUAGAGUGUCUUAAAAUGUUUCAAAUGGUUUAACA<br>AAAUGUAUGUGAGGCGUAUGUGGCAAAAUGUUACAGAAUCUACUGGUUGGACAU<br>GGCUGUUCAUUGUACUGGUUUUUCUAUCUUCUAUAUGUUUAAAAGUAUAUAAU<br>AAAAAUAUUUAAUUUUUUUUUUAAAAAAAAAAAAAAAAAAACAAAAAAAAAAAA<br>(SEQ ID NO: 1) |
| Human SMN-1 (Amino Acid Seq.) | MAMSSGGSGGGVPEQEDSVLFRRGTGQSDDSDIWDDTALIKAYDKAVASFKHAL<br>KNGDTCETSGKPKTTPKPKPAKKNKSQKKNTAASLQQWKVGDKCSATWSEDGCT<br>YPATIASIDFKRETCVVVYTGYGNREEQNLSDLLSPICEVANNIEQNAQENENE<br>SQVSTDESENSRSPGNKSDNIKPKSAPWNSFLPPPPPMPGPRLGPGKPGLKFNG<br>PPPPPPPPPPHLLSCWLPPFPSGPPIIPPPPPICPDSLDDADALGSMLISWYMS<br>GYHTGYYMGFRQNQKEGRCSHSLN (SEQ ID NO: 2) |

Thus, in some embodiments, a suitable mRNA for the present invention is a wild-type hSMN-1 mRNA sequence (SEQ ID NO:1). In some embodiments, a suitable mRNA may be a codon optimized hSMN-1 mRNA sequence represented by (SEQ ID NO:3):

AUGGCCAUGAGCAGCGGAGGCAGCGGCGGAGGAGUGCCCGAGCAGGAGGA

CAGCGUGCUGUUCAGGAGAGGCACCGGCCAGAGCGAUGACAGCGAUAUCU

GGGACGAUACCGCUCUGAUGAAGGCCUACGACAAGGCCGUGGCCAGCUUC

AAGCACGCCCUGAAAAACGGCGACAUCUGCGAGACCAGCGGCAAGCCCAA

GACAACCCCCAAGAGAAAGCCCGCCAAGAAGAAUAAGAGCCAGAAAAAGA

ACACCGCCGCCAGCCUGCAGCAGUGGAAGGUGGGCGACAAGUGCAGCGCC

AUCUGGAGCGAGGACGGCUGCAUCUACCCCGCCACCAUCGCCAGCAUCGA

CUUCAAGAGAGAGACCUGCGUGGUCGUGUACACCGGCUACGGCAACAGAG

AGGAGCAGAACCUGAGCGACCUGCUGAGCCCCAUUUGUGAGGUGGCCAAU

AACAUCGAACAGAACGCCCAGGAGAACGAGAAUGAAAGCCAGGUGAGCAC

CGACGAGAGCGAGAACAGCAGAUCUCCUGGCAACAAGAGCGACAACAUCA

AGCCUAAGUCUGCCCCUUGGAACAGCUUCCUGCCCCCUCCUCCACCCAUG

CCCGGACCCAGACUGGGACCCGGAAAACCUGGCCUGAAGUUCAACGGACC

ACCUCCCCCUCCACCUCCUCCCCCACCUCAUCUCCUGAGCUGCUGGCUGC

CACCCUUCCCCAGCGGACCCCCUAUCAUCCCACCACCCCCUCCCAUCUGC

CCCGACAGCCUGGACGACGCCGAUGCCCUGGGCAGCAUGCUGAUCAGCUG

GUACAUGAGCGGCUACCACACAGGAUACUACAUGGGCUUCAGACAGAACC

AGAAGGAGGGCAGAUGCUCCCACUCCCUGAACUGA

Alternatively, in some embodiments, a suitable mRNA may be a codon optimized hSMN-1 mRNA sequence represented by (SEQ ID NO:4):

AUGGCCAUGAGCAGCGGAGGAAGCGGAGGAGGAGUGCCAGAACAGGAAGA

UAGCGUGCUGUUUCGCCGGGGCACCGGACAAUCGGACGACAGCGAUAUUU

GGGACGACACUGCGCUCAUCAAGGCCUACGACAAGGCGGUGGCUUCGUUC

AAGCACGCUCUGAAGAACGGGGAUAUCUGUGAAACCAGCGGUAAACCAAA

AACUACGCCGAAAAGGAAACCCGCCAAAAAGAACAAGUCACAGAAGAAGA

AUACCGCUGCGAGCUUGCAGCAGUGGAAGGUGGGCGACAAGUGCUCCGCG

AUUUGGUCGGAAGAUGGUUGCAUCUACCCGGCAACCAUCGCCUCCAUCGA

CUUUAAGCGGGAGACUUGCGUCGUGGUGUACACCGGAUACGGCAAUAGAG

AGGAACAGAAUCUGUCAGACCUUCUGUCGCCAAUCUGCGAGGUCGCCAAC

AAUAUCGAACAAAACGCCCAAGAGAACGAGAAUGAGUCCCAAGUGUCCAC

GGACGAAUCGGAAAACUCACGGUCCCCUGGGAACAAGUCAGAUAACAUCA

AGCCUAAAUCGGCACCAUGGAACUCCUUCCUGCCGCCUCCGCCUCCGAUG

CCGGGCCCGCGCCUGGGACCGGGUAAACCCGGGCUCAAGUUCAAUGGACC

```
                                 -continued
GCCACCCCCACCCCCGCCACCGCCGCCCCACCUCCUCUCGUGCUGGCUGC

CGCCGUUCCCUUCCGGACCGCCUAUCAUUCCGCCACCUCCACCUAUCUGC

CCAGACAGCCUGGAUGAUGCCGACGCAUUGGGCUCCAUGCUCAUCUCAUG

GUACAUGUCGGGAUACCAUACUGGGUAUUACAUGGGCUUCAGACAGAACC

AGAAGGAAGGACGCUGUUCCCAUAGCCUGAACUAG
```

In some embodiments, a suitable mRNA encodes a full length, fragment or portion of human Survival of Motor Neuron-2 (hSMN-2) protein. The mRNA sequence for hSMN-2 and corresponding amino acid sequence of a typical wild-type or naturally occurring hSMN-2 protein are shown in Table 4.

97%, 98%, 99% or more homologous to SEQ ID NO:2 or SEQ ID NO:6. In some embodiments, an mRNA suitable for the present invention encodes a protein substantially identical to human SMN-1 protein (SEQ ID NO:2) or human SMN-2 protein (SEQ ID NO:6). In some embodiments, an mRNA suitable for the present invention encodes an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:2 or SEQ ID NO:6. In some embodiments, an mRNA suitable for the present invention encodes a fragment or a portion of human SMN-1 or human SMN-2 protein, wherein the fragment or portion of the protein still maintains SMN-1 or SMN-2 activity similar to that of their respective wild-type proteins. In some embodiments, an mRNA suitable for the present

TABLE 4

Human SMN-2

| | |
|---|---|
| Human SMN-2 (mRNA) | GGGGCCCCACGCUGCGCACCCGCGGGUUUGCUAUGGCGAUGAGCAGCGGCGGCA GUGGUGGCGGCGUCCCGGAGCAGGAGGAUUCCGUGCUGUUCCGGCGCGGCACAG GCCAGAGCGAUGAUUCUGACAUUUGGGAUGAUACAGCACUGAUAAAAGCAUAUG AUAAAGCUGUGGCUUCAUUUAAGCAUGCUCUAAAGAAUGGUGACAUUUGUGAAA CUUCGGGUAAACCAAAAACCACACCUAAAAGAAAACCUGCUAAGAAGAAUAAAA GCCAAAAGAAGAAUACUGCAGCUUCCUUACAACAGUGGAAAGUUGGGGACAAAU GUUCUGCCAUUUGGUCAGAAGACGGUUGCAUUUACCCAGCUACCAUUGCUUCAA UUGAUUUUAAGAGAGAAACCUGUGUUGUGGUUUACACUGGAUAUGGAAAUGAGAG AGGAGCAAAAUCUGUCCGAUCUACUUUCCCCAAUCUGUGAAGUAGCUAAUAAUA UAGAACAGAAUGCUCAAGAGAAUGAAAAUGAAAGCCAAGUUUCAACAGAUGAAA GUGAGAACUCCAGGUCUCCUGGAAAUAAAUCAGAUAACAUCAAGCCCAAAUCUG CUCCAUGGAACUCUUUUCUCCCUCCACCACCCCCAUGCCAGGGCCAAGACUGG GACCAGGAAAGCCAGGUCUAAAAUUCAAUGGCCCACCACCGCCACCGCCACCAC CACCACCCCACUUACUAUCAUGCUGGCUGCCUCCAUUUCCUUCUGGACCACCAA UAAUUCCCCCACCACCUCCCAUAUGUCCAGAUUCUCUUGAUGAUGCUGAUGCUU UGGGAAGUAUGUUAAUUUCAUGGUACAUGAGUGGCUAUCAUACUGGCUAUUAUA UGGAAAUGCUGGCAUAGAGCAGCACUAAAUGACACCACUAAAGAAACGAUCAGA CAGAUCUGGAAUGUGAAGCGUUAUAGAAGAUAACUGGCCUCAUUUCUUCAAAAU AUCAAGUGUUGGGAAAGAAAAAAGGAAGUGGAAUGGGUAACUCUUCUUGAUUAA AAGUUAUGUAAUAACCAAAUGCAAUGUGAAAUAUUUUACUGGACUCUAUUUUGA AAAACCAUCUGUAAAAGACUGAGGUGGGGGUGGGAGGCCAGCACGGUGGUGAGG CAGUUGAGAAAAUUUGAAUGUGGAAUAGAUUUUGAAUGAUAUUGGAUAAUUAUU GGUAAUUUUAUGAGCUGUGAGAAGGGUGUUGUAGUUUAUAAAAGACUGUCUUAA UUUGCAUACUUAAGCAUUUAGGAAUGAAGUGUUAGAGUGUCUUAAAAUGUUUCA AAUGGUUUAACAAAAAUGUAUGUGAGGCGUAUGUGGCAAAAUGUUACAGAAUCUA ACUGGUGGACAUGGCUGUUCAUUGUACUGUUUUUUUCUAUCUUCUAUAUGUUUA AAAGUAUAUAAUAAAAAAUAUUUAAUUUUUUUUUUAAAAA (SEQ ID NO: 5) |
| Human SMN-2 (Amino Acid Seq.) | MAMSSGGSGGGVPEQEDSVLFRRGTGQSDDSDTWDDTALIKAYDKAVASFKHAL KNGDICETSGKPKTTPKRKPAKKNKSQKKNTAASLQQWKVGDKCSAIWSEDGCI YPATIASIDFKRETCVVVYTGYGNREEQNLSDLLSPICEVANNIEQNAQENENE SQVSTDESENSRSPGNKSDNIKPKSAPWNSFLPPPPPMPGPRLGPGKPGLKFNG PPPPPPPPPPHLLSCWLPPFPSGPPIIPPPPPICPDSLDDADALGSMLISWYMS GYHTGYYMEMLA (SEQ ID NO : 6) |

Thus, in some embodiments, a suitable mRNA for the present invention is a wild-type hSMN-2 mRNA sequence (SEQ ID NO:5). In some embodiments, a suitable mRNA may be a codon optimized hSMN-1 mRNA sequence.

In some embodiments, a suitable mRNA sequence may be an mRNA sequence encoding a homologue or an analogue of human SMN-1 (SEQ ID NO. 2) or human SMN-2 (SEQ ID NO. 6) proteins. For example, a homologue or an analogue of human SMN-1 or SMN-2 protein may be a modified human SMN-1 or SMN-2 protein containing one or more amino acid substitutions, deletions, and/or insertions as compared to a wild-type or naturally-occurring human SMN-1 protein (e.g., SEQ ID NO:2) or human SMN-2 protein (e.g., SEQ ID NO:6), while retaining substantial SMN-1 or SMN-2 protein activity. In some embodiments, an mRNA suitable for the present invention encodes an amino acid sequence at least 50%, 55%, 60%, 65%, 70%, 75%, 80%, 85%, 90%, 91%, 92%, 93%, 94%, 95%, 96%, invention comprises a nucleotide sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:1, SEQ ID NO:3, SEQ ID NO:4 or SEQ ID NO:5.

Human SMN-1 gene may undergo alternative processing and transcriptional modification to produce alternative splice isoforms. For example, there are five known hSMN-1 splice isoforms: hSMN-1 isoform b, c, e, f and g. Human SMN-2 gene can also undergo alternative processing and transcriptional modification to produce alternative splice isoforms. There are four known hSMN-2 splice isoforms: hSMN-2 isoform a, b, c and d. In some embodiments, the present invention is used to deliver an mRNA encoding an hSMN-1 isoform (e.g., isoform b, c, e, f, or g). In some embodiments, the present intention is used to deliver an mRNA encoding an hSMN-2 isoform (e.g., isoform a, b, c of d). The nucleotide and amino acid sequence of the hSMN-1 and hSMN-2 isoforms are known in the art. Thus, in some embodiments, the present invention can be used to deliver an mRNA encoding and hSMN-1 isoform or an hSMN-2 protein or an isoform thereof. In some embodiments, an mRNA suitable for the invention may be a wild-type or naturally occurring hSMN-1 or hSMN-2 isoform sequence. In some embodiments, an mRNA suitable for the invention may be a codon-optimized hSMN-1 or hSMN-2 isoform sequence. In some embodiments, an mRNA suitable for the invention may encode an amino acid sequence having substantial homology or identify to the wild-type or naturally-occurring hSMN-1 or hSMN-2 isoform sequence (e.g., having at least 50%, 55%, 60%, 65%, 70%, 75%, 80%, 85%, 90%, 95%, 98% sequence identity to the wild-type or naturally occurring hSMN-1 or hSMN-2 isoform sequence).

mRNA Synthesis mRNAs according to the present invention may be synthesized according to any of a variety of known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor. The exact conditions will vary according to the specific application.

In some embodiments, for the preparation of mRNA according to the invention, a DNA template is transcribed in vitro. A suitable DNA template typically has a promoter, for example a T3, T7 or SP6 promoter, for in vitro transcription, followed by desired nucleotide sequence for desired mRNA and a termination signal.

Desired mRNA sequence(s) according to the invention may be determined and incorporated into a DNA template using standard methods. For example, starting from a desired amino acid sequence (e.g., an enzyme sequence), a virtual reverse translation is carried out based on the degenerated genetic code. Optimization algorithms may then be used for selection of suitable codons. Typically, the G/C content can be optimized to achieve the highest possible G/C content on one hand, taking into the best possible account the frequency of the tRNAs according to codon usage on the other hand. The optimized RNA sequence can be established and displayed, for example, with the aid of an appropriate display device and compared with the original (wild-type) sequence. A secondary structure can also be analyzed to calculate stabilizing and destabilizing properties or, respectively, regions of the RNA.

Modified mRNA

In some embodiments, mRNA according to the present invention may be synthesized as unmodified or modified mRNA. Typically, mRNAs are modified to enhance stability. Modifications of mRNA can include, for example, modifications of the nucleotides of the RNA. An modified mRNA according to the invention can thus include, for example, backbone modifications, sugar modifications or base modifications. In some embodiments, mRNAs may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methyl-thio-N-6-isopentenyl-adeninie, N6-methyl-adeine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, beta.-D-mannosyl-queosine, wybutoxosine, and phosphoramidates, phosphorothioates, peptide nucleotides, methylphosphonates, 7-deazaguanosine, 5-methylcytosine and inosine. The preparation of such analogues is known to a person skilled in the art e.g. from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosures of which are incorporated by referece in their entirety.

In some embodiments, mRNAs may contain RNA backbone modifications. Typically, a backbone modification is a modification in which the phosphates of the backbone of the nucleotides contained in the RNA are modified chemically. Exemplary backbone modifications typically include, but are not limited to, modifications from the group consisting of methylphosphonates, methylphosphoramidates, phosphoramidates, phosphorothioates (e.g. cytidine 5'-O-(1-thiophosphate)), boranophosphates, positively charged guanidinium groups etc., which means by replacing the phosphodiester linkage by other anionic, cationic or neutral groups.

In some embodiments, mRNAs may contain sugar modifications. A typical sugar modification is a chemical modification of the sugar of the nucleotides it contains including, but not limited to, sugar modifications chosen from the group consisting of 2'-deoxy-2'-fluoro-oligoribonucleotide (2'-fluoro-2'-deoxycytidine 5'-triphosphate, 2'-fluoro-2'-deoxyuridine 5'-triphosphate), 2'-deoxy-2'-deamine-oligoribonucleotide (2'-amino-2'-deoxycytidine 5'-triphosphate, 2'-amino-2'-deoxyuridine 5'-triphosphate), 2'-O-alkyloligoribonucleotide, 2'-deoxy-2'-C-alkyloligoribonucleotide (2'-O-methylcytidine 5'-triphosphate, 2'-methyluridine 5'-triphosphate), 2'-C-alkyloligoribonucleotide, and isomers thereof (2'-aracytidine 5'-triphosphate, 2'-arauridine 5'-triphosphate), or azidotriphosphates (2'-azido-2'-deoxycytidine 5'-triphosphate, 2'-azido-2'-deoxyuridine 5'-triphosphate).

In some embodiments, mRNAs may contain modifications of the bases of the nucleotides (base modifications). A modified nucleotide which contains a base modification is also called a base-modified nucleotide. Examples of such base-modified nucleotides include, but are not limited to, 2-amino-6-chloropurine riboside 5'-triphosphate, 2-aminoadenosine 5'-triphosphate, 2-thiocytidine 5'-triphosphate, 2-thiouridine 5'-triphosphate, 4-thiouridine 5'-triphosphate, 5-aminoallylcytidine 5'-triphosphate, 5-aminoallyluridine 5'-triphosphate, 5'-bromocytidine 5'triphosphate, 5-bromouridine 5'-triphosphate, 5'-iodocytidine 5'-triphosphate, 5-iodouridine 5'-triphosphate, 5-methylcytidine 5'-triphosphate, 5-methyluridine 5'-triphosphate, 6-azacytidine 5'-triphosphate, 6-azauridine 5'-triphosphate, 6-chloropurine riboside 5'-triphosphate, 7-deazaadenosine 5'-triphosphate, 7-deazaguanosine 5'-triphosphate, 8-azaadenosine 5'-triphosphate, 8-azidoadenosine, 5'-triphosphate, benzimidazole riboside 5'-triphosphate, N1-methyladenosine 5'-triphosphate, N1-methylguanosine 5'-triphosphate, N6-methyladenosine 5'-triphosphate, O6-methlguanosine 5'-triphosphate, pseudouridine 5'-triphosphate, puromycin 5'-triphosphate or xanthosine 5'-triphosphate.

Typically, mRNA synthesis includes the addition of a "cap" on the N-terminal (5') end, and a "tail" on the C-terminal (3') end. The presence of the cap is important in providing resistance to nucleases found in most eukaryotic cells. The presence of a "tail" serves to protect the mRNA from exonuclease degradation.

Cap Structure

In some embodiments, mRNAs include a 5' cap structure. A 5' cap is typically added as follows: first, an RNA terminal phosphatase removes one of the terminal phosphate groups from the 5' nucleotide, leaving two terminal phosphates, guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp(5'(A,G(5')ppp(5')A and G(5')ppp(5')G.

Naturally occurring cap structures comprise a 7-methyl guanosine that is linked via a triphosphate bridge to the 5'-end of the first transcribed nucleotide, resulting in a dinucleotide cap of $m^7G(5')ppp(5')N$, where N is any nucleoside. In vivo, the cap is added enzymatically. The cap is added in the nucleus and is catalyzed by the enzyme guanylyl transferase. The addition of the cap to the 5' terminal end of RNA occurs immediately after initiation of transcription. The terminal nucleoside is typically a guanosine, and is in the reverse orientation to all the other nucleotides, i.e., G(5')ppp(5')GpNpNp.

A common cap for mRNA produced by in vitro transcription is $m^7G(5')ppp(5')G$, which has been used as the dinucleotide cap in transcription with T7 or SP6 RNA polymerase in vitro to obtain RNAs having a cap structure in their 5'-termini. The prevailing method for the in vitro synthesis of capped mRNA employs a pre-formed dinucleotide of the form $m^7G(5')ppp(5')G$ ("$m^7GpppG$") as an initiator of transcription.

To date, a usual form of a synthetic dinucleotide cap used in in vitro translation experiments is the Anti-Reverse Cap Analog ("ARCA") or modified ARCA, which is generally a modified cap analog in which the 2' or 3' OH group is replaced with —$OCH_3$.

Additional cap analogs include, but are not limited to, a chemical structures selected from the group consisting of $m^7GpppG$, $m^7GpppA$, $m^7GpppC$; unmethylated cap analogs (e.g., GpppG); dimethylated cap analog (e.g., $m^{2,7}GpppG$), trimethylated cap analog (e.g., $m^{2,2,7}GpppG$), dimethylated symmetrical cap analogs (e.g., $m^7Gpppm^7G$), or anti reverse cap analogs (e.g., ARCA; $m^{7,2'Ome}GpppG$, $m^{7,2'd}GpppG$, $m^{7,3'Ome}GpppG$, $m^{7,3'd}GpppG$ and their tetraphosphate derivatives) (see, e.g., Jemielity, J. et al., "Novel 'anti-reverse' cap analogs with superior translational properties", RNA, 9: 1108-1122 (2003)).

In some embodiments, a suitable cap is a 7-methyl guanylate ("$m^7G$") linked via a triphosphate bridge to the 5'-end of the first transcribed nucleotide, resulting in $m^7G(5')ppp(5')N$, where N is any nucleoside. A preferred embodiment of a $m^7G$ cap utilized in embodiments of the invention is $m^7G(5')ppp(5')G$.

In some embodiments, the cap is a Cap0 structure. Cap0 structures lack a 2'-O-methyl residue of the ribose attached to bases 1 and 2. In some embodiments, the cap is a Cap1 structure. Cap1 structures have a 2'-O-methyl residue at base 2. In some embodiments, the cap is a Cap2 structure. Cap2 structures have a 2'-O-methyl residue attached to both bases 2 and 3.

A variety of $m^7G$ cap analogs are known in the art, many of which are commercially available. These include the $m^7GpppG$ described above, as well as the ARCA 3'-$OCH_3$ and 2'-$OCH_3$ cap analogs (Jemielity, J. et al., RNA, 9: 1108-1122 (2003)). Additional cap analogs for use in embodiments of the invention include N7-benzylated dinucleoside tetraphosphate analogs (described in Grudzien, E. et al., RNA, 10: 1479-1487 (2004)), phosphorothioate cap analogs (described in Grudzien-Nogalska, E., et al., RNA, 13: 1745-1755 (2007)), and cap analogs (including biotinylated cap analogs) described in U.S. Pat. Nos. 8,093,367 and 8,304,529, incorporated by reference herein.

Tail Structure

Typically, the presence of a "tail" serves to protect the mRNA from exonuclease degradation. The poly A tail is thought to stabilize natural messengers and synthetic sense RNA. Therefore, in certain embodiments a long poly A tail can be added to an mRNA molecule thus rendering the RNA more stable. Poly A tails can be added using a variety of art-recognized techniques. For example, long poly A tails can be added to synthetic or in vitro transcribed RNA using poly A polymerase (Yokoe, et al. Nature Biotechnology. 1996; 14: 1252-1256). A transcription vector can also encode long poly A tails. In addition, poly A tails can be added by transcription directly from PCR products. Poly A may also be ligated to the 3' end of a sense RNA with RNA ligase (see, e.g., Molecular Cloning A Laboratory Manual, 2nd Ed., ed. by Sambrook, Fritsch and Maniatis (Cold Spring Harbor Laboratory Press: 1991 edition)).

In some embodiments, mRNAs include a 3' poly(A) tail structure. Typically, the length of the poly A tail can be at least about 10, 50, 100, 200, 300, 400 at least 500 nucleotides. In some embodiments, a poly-A tail on the 3' terminus of mRNA typically includes about 10 to 300 adenosine nucleotides (e.g., about 10 to 200 adenosine nucleotides, about 10 to 150 adenosine nucleotides, about 10 to 100 adenosine nucleotides, about 20 to 70 adenosine nucleotides, or about 20 to 60 adenosine nucleotides). In some embodiments, mRNAs include a 3' poly(C) tail structure. A suitable poly-C tail on the 3' terminus of mRNA typically include about 10 to 200 cytosine nucleotides (e.g., about 10 to 150 cytosine nucleotides, about 10 to 100 cytosine nucleotides, about 20 to 70 cytosine nucleotides, about 20 to 60 cytosine nucleotides, or about 10 to 40 cytosine nucleotides). The poly-C tail may be added to the poly-A tail or may substitute the poly-A tail.

In some embodiments, the length of the poly A or poly C tail is adjusted to control the stability of a modified sense mRNA molecule of the invention and, thus, the transcription of protein. For example, since the length of the poly A tail can influence the half-life of a sense mRNA molecule, the length of the poly A tail can be adjusted to modify the level of resistance of the mRNA to nucleases and thereby control the time course of polynucleotide expression and/or polypeptide production in a target cell.

5' and 3' Untranslated Region

In some embodiments, mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

Exemplary 3' and/or 5' UTR sequences can be derived from mRNA molecules which are stable (e.g., globin, actin, GAPDH, tubulin, histone, or citric acid cycle enzymes) to increase the stability of the sense mRNA molecule. For example, a 5' UTR sequence may include a partial sequence of a CMV immediate-early 1 (IE1) gene, or a fragment thereof to improve the nuclease resistance and/or improve the half-life of the polynucleotide. Also contemplated is the inclusion of a sequence encoding human growth hormone (hGH), or a fragment thereof to the 3' end or untranslated region of the polynucleotide (e.g., mRNA) to further stabilize the polynucleotide. Generally, these modifications improve the stability and/or pharmacokinetic properties (e.g., half-life) of the polynucleotide relative to their unmodified counterparts, and include, for example modifications made to improve such polynucleotides' resistance to in vivo nuclease digestion.

Delivery Vehicles

According to the present invention, mRNA may be delivered to the CNS as naked RNA (unpackaged) or via delivery vehicles. As used herein, the terms "delivery vehicle," "transfer vehicle," "Nanoparticle" or grammatical equivalent, are used interchangeably.

In some embodiments, mRNAs may be delivered via a single delivery vehicle. In some embodiments, mRNAs may be delivered via one or more delivery vehicles each of a different composition. According to various embodiments, suitable delivery vehicles include, but are not limited to, polymer based carriers, such as polyethyleneimine (PEI), lipid nanoparticles and liposomes, nanoliposomes, ceramide-containing nanoliposomes, proteoliposomes, both natural and synthetically-derived exosomes, natural, synthetic and semi-synthetic lamellar bodies, nanoparticulates, calcium phosphor-silicate-nanoparticulates, calcium phosphate nanoparticulates, silicon dioxide nanoparticulates, nanocrystalline particulates, semiconductor nanoparticulates, poly(D-arginine), sol-gels, nanodendrimers, starch-based delivery systems, micelles, emulsions, niosomes, multi-domain-block polymers (vinyl polymers, polypropyl acrylic acid polymers, dynamic polyconjugates), dry powder formulations, plasmids, viruses, calcium phosphate nucleotides, aptamers, peptides and other vectorial tags.

Liposomal Delivery Vehicles

In some embodiments, a suitable delivery vehicle is a liposomal delivery vehicle, e.g. a lipid nanoparticle. As used herein, liposomal delivery vehicles, e.g. lipid nanoparticles, are usually characterized as microscopic vesicles having an interior aqua space sequestered from an outer medium by a membrane of one or more bilayers. Bilayer membranes of liposomes are typically formed by amphiphilic molecules, such as lipids of synthetic or natural origin that comprise spatially separated hydrophilic and hydrophobic domains (Lasic, Trends Biotechnol., 16:307-321, 1998). Typically, a liposomal delivery vehicle (e.g., a lipid nanoparticle or liposome) suitable for the present invention is formed by combining one or more different lipids and/or polymers. In some embodiments, a liposomal delivery vehicle (e.g., a lipid nanoparticle or liposome) contains one or more cationic lipids, one or more non-cationic/helper lipids, one or more cholesterol based lipids, and/or one or more PEGylated lipids.

Cationic Lipids

In some embodiments, a suitable delivery vehicle contains a cationic lipid. As used herein, the phrase "cationic lipid" refers to any of a number of lipid species that have a net positive charge at a selected pH, such as physiological pH. Some cationic lipids, in particular, those known as titratable or pH-titratable cationic lipids are particularly effective in delivering mRNA. Several cationic (e.g., titratable) lipids have been described in the literature, many of which are commercially available. Particularly suitable cationic lipids for use in the compositions and methods of the invention include those described in international patent publications WO 2010/053572 (and particularly, CI 2-200 described at paragraph [00225]) and WO 2012/170930, both of which are incorporated herein by reference. In some embodiments, the cationic lipid N-[1-(2,3-dioleyloxy)propyl]-N,N,N-trimethylammonium chloride or "DOTMA" is used. (Feigner et al. (Proc. Nat'l Acad. Sci. 84, 7413 (1987); U.S. Pat. No. 4,897,355). DOTMA can be formulated alone or can be combined with the neutral lipid, dioleoylphosphatidylethanolamine or "DOPE" or other cationic or non-cationic lipids into a liposomal transfer vehicle or a lipid nanoparticle, and such liposomes can be used to enhance the delivery of nucleic acids into target cells. Other suitable cationic lipids include, for example, 5-carboxyspermylglycinedioctadecylamide or "DOGS," 2,3-dioleyloxy-N-[2 (spermine-carboxamido)ethyl]-N,N-dimethyl-1-propan-aminium or "DOSPA" (Behr et al. Proc. Nat'l Acad. Sci. 86, 6982 (1989); U.S. Pat. Nos. 5,171,678, 5,334,761), 1,2-Dioleoyl-3-Dimethylammonium-Propane or "DODAP", 1,2-Dioleoyl-3-Trimethylammonium-Propane or "DOTAP". Contemplated cationic lipids also include 1,2-distearyloxy-N,N-dimethyl-3-aminopropane or "DSDMA", 1,2-dioleyloxy-N,N-dimethyl-3-aminopropane or "DOTMA", 1,2-dilinoleyloxy-N,N-dimethyl-3-aminopropane or "DLinDMA", 1,2-dilinolenyloxy-N,N-dimethyl-3-aminopropane or "DLenDMA", N-dioleyl-N,N-dimethylammonium chloride or "DODAC", N,N-distearyl-N,N-dimethyl-arnmonium bromide or "DDAB", N-(1,2-dimyristyloxyprop-3-yl)-N,N-dimethyl-N-hydroxyethyl ammonium bromide or "DMRIE", 3-dimethylamino-2-(cholest-5-en-3-beta-oxybutan-4-oxy)-1-(cis,cis-9,12-octadecadienoxy)propane or "CLinDMA", 2-[5'(cholest-5-en-3-beta-oxy)-3'-oxapentoxy)-3-dimethyl-1-(cis,cis-9', 1-2'octadecadienoxy)propane or "CpLinDMA", N,N-dimethyl-3,4-dioleyloxybenzylamine or "DMOBA", 1,2 -N,N'-dioleylcarbamyl-3-dimethylaminopropane or "DOcarbDAP", 2,3-Dilinoleoyloxy-N,N-dimethylpropylamine or "DLinDAP", 1,2-N,N-Dilinoleylcarbamyl-3-dimethylaminopropane or "DLincarbDAP", 1,2-Dilinoleoylcarbamyl-3-dimethylaminopropane or "DLinCDAP", 2,2-dilinoleyl-4-dimethylaminomethyl-[1,3]-dioxolane or "DLin-K DMA", 2,2-dilinoleyl-4-dimethylaminoethyl-[1,3]-dioxolane or "DLin-K-XTC2-DMA", and 2-(2,2-di((9Z,12Z)-octadeca-9,12-dien-1-yl)-1,3-dioxolan-4-yl)-N,N-dimethyl-ethanamine (DLin-KC2-DMA)) (See, WO 2010/042877; Semple et al., Nature Biotech. 28: 172-176 (2010)), or mixtures thereof (Heyes, J., et al., J Controlled Release 107: 276-287 (2005); Morrissey. D V., et al., Nat. Biotechnol. 23(8): 1003-1007 (2005); PCT Publication WO2005/121348A1).

In some embodiments, one or more of the cationic lipids present in such a composition are chosen from XTC (2,2-Dilinoleyl-4-dimethylaminoethyl-[1,3]-diaxolane), MC3

(((6Z,9Z,28Z,31Z)-heptatriaconta-6,9,28,31-tetraen-19-yl 4-(dimethylamino)butanoate), ALNY-100 ((3aR,5s,6aS)-N,N-dimethyl-2,2-di((9Z,12Z)-octadeca-9,12-dientl)tetrahydro-3aH-cyclopenta[d][1,3]dioxol-5-amine)), NC98-5 (4,7,13-tris(3-oxo-3-(undecylamino)propyl)-N1,N16-diundecyl-4,7,10,13-tetraazahexadecane-1,16-diamide), DODAP (1,2-dioleyl-3-dimethylammonium propane), HGT4003 (WO 2012/170889, the teachings of which are incorporated herein by reference in their entirety), ICE (WO 2011/068810, the teachings of which are incorporated herein by reference in their entirety).

In certain embodiments, the compositions and methods of the invention employ a lipid nanoparticles comprising an ionizable cationic lipid described in U.S. provisional patent application 61/617,468, filed Mar. 29, 2012 (incorporated herein by reference), such as, e.g., (15Z,18Z)-N,N-dimethyl-6-(9Z,12Z)-octadeca-9, 12-dien-1-yl)tetracosa-15,18-dien-1-amine (HGT5000), (15Z,18Z)-N,N-dimethyl-6-((9Z,12Z)-octadeca-9,12-dien-1-yl)tetracosa-4,15,18-trien-1-amine (HGT500l), and (15Z,18Z)-N,N-dimethyl-6-((9Z,12Z)-octadeca-9,12-dien-1-yl)tetracosa-5,15,18-trien-1-amine (HGT5002).

In some embodiments, provided liposomes include a cationic lipid described in WO 2013063468 and in U.S. provisional application entitled "Lipid Formulations for Delivery of Messenger RNA" filed concurrently with the present application on even date, both of which are incorporated by reference herein. In some embodiments, a cationic lipid comprises a compound formula I-c1-a:

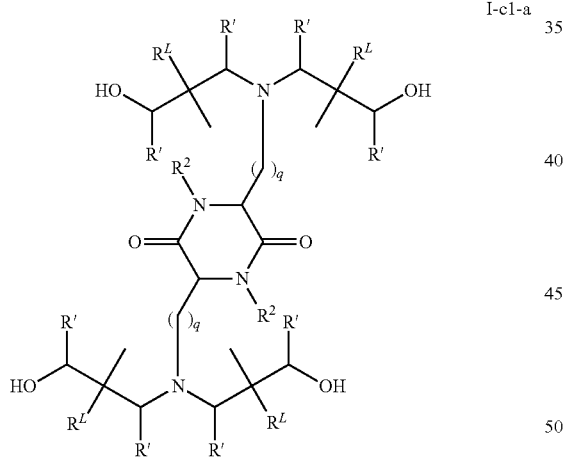

or a pharmaceutically acceptable salt thereof, wherein:
each $R^2$ independently is hydrogen or $C_{1-3}$ alkyl;
each q independently is 2 to 6;
each R' independently is hydrogen or $C_{1-3}$ alkyl;
and each $R^L$ independently is $C_{8-12}$ alkyl.

In some embodiments, each $R^2$ independently is hydrogen, methyl or ethyl. In some embodiments, each $R^2$ independently is hydrogen or methyl. In some embodiments, each $R^2$ is hydrogen.

In some embodiments, each q independently is 3 to 6. In some embodiments, each q independently is 3 to 5. In some embodiments, each q is 4.

In some embodiments, each R' independently is hydrogen, methyl or ethyl. In some embodiments, each R' independently is hydrogen or methyl. In some embodiments, each R' independently is hydrogen.

In some embodiments, each $R^L$ independently is $C_{8-12}$ alkyl. In some embodiments, each $R^L$ independently is n-$C_{8012}$ alkyl. In some embodiments, each $R^L$ independently is $C_{9-11}$ alkyl. In some embodiments, each $R^L$ independently is n-$C_{9-11}$ alkyl. In some embodiments, each $R^L$ independently is $C_{10}$ alkyl. In some embodiments, each $R^L$ independently isn-$C_{10}$ alkyl.

In some embodiments, each $R^2$ independently is hydrogen or methyl; each q independently is 3 to 5; each R' independently is hydrogen or methyl; and each $R^L$ independently is $C_{8-12}$ alkyl.

In some embodiments, each $R^2$ is hydrogen; each q independently is 3 to 5; each R' is hydrogen; and each $R^L$ independently is $C_{8-12}$ alkyl.

In some embodiments, each $R^2$ is hydrogen; each q is 4; each R' is hydrogen; and each $R^L$ independently is $C_{8-12}$ alkyl.

In some embodiments, a cationic lipid comprises a compound of formula I-g:

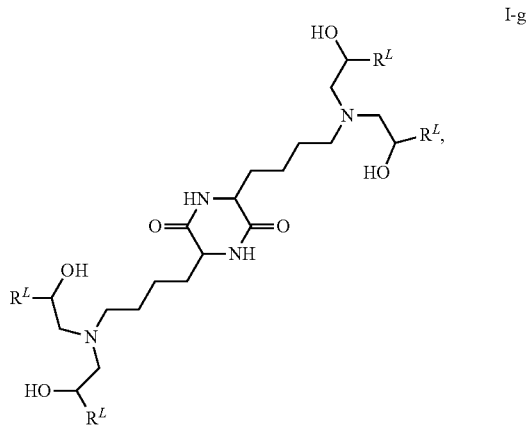

or a pharmaceutically acceptable salt thereof, wherein each $R^L$ independently is $C_{8-12}$ alkyl. In some embodiments, each $R^L$ independently is n-$C_{8-12}$ alkyl. In some embodiments, each $R^L$ independently is $C_{9-11}$ alkyl. In some embodiments, each $R^L$ independently is n-$C_{9-11}$ alkyl. In some embodiments, each $R^L$ independently is $C_{10}$ alkyl. In some embodiments, each $R^L$ is n-$C_{10}$ alkyl.

In particular embodiments, provided liposomes include a cationic lipid cKK-E12, or (3,6-bis(4-(bis(2-hydroxydodecyl)amino)butyl)piperazine-2,5-dione). Structure of cKK-E12 is shown below.

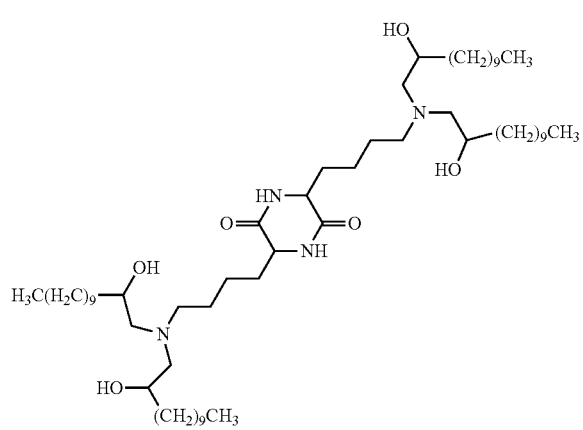

In some embodiments, suitable lipid nanoparticles of the invention comprise at least one of the following cationic lipids: C12-200, DLin-KC2-DMA, cKK-E12, Re-1, DODMA, DODAP, HGT4003, ICE, XTC, DSPC, MC3, HGT5000, or HGT5001.

In some embodiments, the percentage of cationic lipid in a liposome may be greater than about 10%, greater than about 20%, greater than about 30%, greater than about 40%, greater than about 50%, greater than about 60%, or greater than about 70% by molar ratio. In some embodiments, cationic lipid(s) constitute(s) about 30-50% (e.g., about 30-45%, about 30-40%, about 35-50%, about 35-45%, or about 35-40%) of the liposome by molar ratio. In some embodiments, the cationic lipid constitutes about 30%, about 35%, about 40%, about 45%, or about 50% of the liposome by molar ratio.

Non-Cationic/Helper Lipids

In some embodiments, provided liposomes contain one or more non-cationic ("helper") lipids. As used herein, the phrase "non-cationic lipid" refers to any neutral, zwitterionic or anionic lipid. As used herein, the phrase "anionic lipid" refers to any of a number of lipid species that carry a net negative charge at a selected H, such as physiological pH. In some embodiments, a non-cationic lipid is a neutral lipid, i.e., a lipid that does not carry a net charge in the conditions under which the composition is formulated and/ or administered. Non-cationic lipids include, but are not limited to distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidyletbanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl--oleoyl-phosphatidyethanolamine (SOPE), or a mixture thereof.

In some embodiments, suitable non-cationic ("helper") lipids include one or more phosphatidyl lipids, for example, the phosphatidyl compounds (e.g., phosphatidylglycerol, phosphatidylcholine, phosphatidylserine and phosphatidylethanolamine).

In some embodiments, suitable non-cationic ("helper") lipids include one or more Sphingolipids, for example, sphigosine, ceramide, sphingomyelin, cerebroside and ganglioside.

In some embodiments, non-cationic ("helper") lipids may constitute about 5% about 90% (e.g., about 10-80%, 10-70%, 10-60%, 10-50%, 10-40%, 10-30%, or 10-20%) of the total lipid present in a liposome by molar ratio. In some embodiments, the percentage of non-cationic ("helper") lipids in a liposome may be greater than about 5%, greater than about 10%, greater than about 15%, greater than 20%, greater than about 25%, greater than 30%, greater than about 35%, or greater than 40% by molar ratio.

Cholesterol-Based Lipids

In some embodiments, provided liposomes comprise one or more cholesterol-based lipids. For example, suitable cholesterol-based cationic lipids include, for example, cholesterol, PEGylated cholesterol, DC-Choi (N,N-dimethyl-N-ethylcarboxamidocholesterol), 1,4-bis(3-N-oleylamino-propyl)piperazine (Gao, et al. Biochem. Biophys. Res. Comm. 179, 280 (1991), Wolf et al. BioTechniques 23, 139 (1997); U.S. Pat. No. 5,744,335), or ICE. In some embodiments, cholesterol-based lipids may constitute about 2% to about 30%, or about 5% to about 20% of the total lipid present in a liposome by molar ratio. In some embodiments, The percentage of cholesterol-based lipid in the lipid nanoparticle may be greater than 5%, 10%, greater than 20%, greater than 30%, or greater than 40% by molar ratio.

PEGylated Lipids

In some embodiments, provided lipid nanoparticles comprise one or more PEGylated lipids. For example, the use of polyethylene glycol (PEG)-modified phospholipids and derivatized lipids such as derivatized ceramides (PEG-CER), including N-Octanoyl-Sphingosine-1-[Succinyl (Methoxy Polyethylene Glycol)-2000] (C8 PEG-2000 ceramide) is contemplated by the present invention in combination with one or more of the cationic and, in some embodiments, other lipids. In some embodiments, suitable PEGylated lipids comprise PEG-ceramides having shorter acyl chains (e.g., $C_{14}$ or $C_{18}$). In some embodiments, the PEGylated lipid DSPE-PEG-Maleimide-Lectin may be used. Other contemplated PEG-modified lipids include, but are not limited to, a polyethylene glycol chain of up to 5 kDa in length covalently attached to a lipid with alkyl chain(s) of $C_6$-$C_{20}$ length. Without wishing to be bound by a particular theory, it is contemplated that the addition of PEGylated lipids may prevent complex aggregation and increase circulation lifetime to facilitate the delivery of the liposome encapsulated mRNA to the target cell.

In some embodiments, PEG-modified phospholipids and/ or derivitized lipids may constitute from about 0% to about 20%, about 0% to about 15%, about 0% to about 10%, about 1% to about 10%, about 1% to about 8%, 1% to about 6%, 1% to about 5%, about 2% to about 10%, about 4% to about 10%, of the total lipids present in the liposome by molar ratio. In some embodiments, the percentage of PEG-modified phospholipids and/or derivitized lipids may be of or less than about 20%, about 15%, about 10%, about 9%, about 8%, about 7%, about 6%, about 5%, about 4%, about 3%, about 2%, or about 1% of the total lipids present in the liposome by molar ratio. In some embodiments, the percentage of PEG-muddied phospholipids and/or derivitized lipids may be of or greater than about 1%, about 2%, about 3%, about 4%, about 5%, about 6%, about 7%, about 8%, about 9%, about 10%, about 15%, or about 20% of the total lipids present in the liposome by molar ratio.

Polymers

In some embodiments, a suitable delivery vehicle is formulated using a polymer as a carrier, alone or in combination with other carriers including various lipids described herein. Thus, in some embodiments, liposomal delivery vehicles, as used herein, also encompass polymer containing nanoparticles. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, protamine, PEGylated protamine, PLL, PEGylated PLL and polyethylenimine (PEI). When PEI is present, it may be linear or branched PEI of a molecular weight ranging from 10 to 40 kDA, e.g., 25 kDA branched PEI (Sigma #408727).

In various embodiments, a suitable delivery vehicle (e.g., a lipid nanoparticle) is prepared by combining one or more lipids and/or polymer components described herein. For example, a lipid nanoparticle may be prepared by combining C12-200, sphingomyelin, DOPE, Cholesterol, and DMG PEG; or C12-200, DOPE, cholesterol and DMG-PEG2K; or cKK-E12, DOPE, cholesterol and DMG-PEG2K; or cKK-E12, sphingomyelin, DOPE, cholesterol and DMG-PEG2K; or HGT5001, DOPE, cholesterol and DMG-PEG2K; or HGT4003, DOPE, cholesterol and DMG-PEG2K; or DLinKC2DMA, DOPE, cholesterol and DMG-PEG2K; or ICE, DOPE, cholesterol and DMG-PEG2K; or DODMA, DOPE, cholesterol and DMG-PEG2K; or DODMA, sphingomyelin, DOPE, cholesterol and DMG-PEG2K; or Re-1, DOPE, cholesterol, DMG-PEG2K; or cKK-EE12, DOPE, cholesterol, DMG-PEG2K and/or DSPE-PEG-Maleimide-Lectin.

In various embodiments, the cationic lipids, non-cationic lipids, cholesterol and/or PEG-modified lipids can be combined at various relative molar ratios. For example, the ratio of cationic lipid (e.g., cKK-E12, C12-200, etc.) to non-cationic lipid (e.g., DOPE, sphingomyelin, etc.) to cholesterol-based lipid (e.g., cholesterol) to PEGylated lipid (e.g., DMG-PEG2K) may be between about 30-60:25-30:20-30:1-15, respectively. In some embodiments, the ratio of cationic lipid (e.g., cKK-E12, C12-200, etc.) to non-cationic lipid (e.g., DOPE, sphingomyelin, etc.) to cholesterol-based lipid (e.g., cholesterol) to PEGylated lipid (e.g., DMG-PEG2K) is approximately 40:30:20:10, respectively. In some embodiments, the ratio of cationic lipid (e.g., cKK-E12, C12-200, etc.) to non-cationic lipid (e.g., DOPE, sphingomyelin, etc.) to cholesterol-based lipid (e.g., cholesterol) to PEGylated lipid (e.g., DMG-PEG2K) is approximately 40:30:25:5, respectively. In some embodiments, the ratio of cationic lipid (e.g., cKK-E12, C12-200, etc.) to non-cationic lipid (e.g., DOPE, sphingomyelin, etc.) to cholesterol-based lipid (e.g., cholesterol) to PEGylated lipid (e.g., DMC-PEG2K) is approximately 40:32:25:3, respectively. In some embodiments, the ratio of cationic lipid (e.g., cKK-E12, C12-200, etc.) to non-cationic lipid (e.g., DOPE, sphingomyelin, etc.) to cholesterol-based lipid (e.g., cholesterol) to PEGylated lipid (e.g., DMG-PEG2K) is approximately 50:25:20:5.

Lipid Nanoparticle Preparation

Delivery vehicles, such as lipid nanoparticles, for use in the present invention can be prepared by various techniques which are presently known in the art. Multilamellar vesicles (MLV) may be prepared conventional techniques, for example, by depositing a selected lipid on the inside wall of a suitable container or vessel by dissolving the lipid in an appropriate solvent, and then evaporating the solvent to leave a thin film on the inside of the vessel or by spray drying. An aqueous phase may then added to the vessel with a vortexing motion which results in the formation of MLVs. Uni-lamellar vesicles (ULV) can then be formed by homogenization, sonication or extrusion of the multi-lamellar vesicles. In addition, unilamellar vesicles can be formed by detergent removal techniques.

In certain embodiments of this invention, the compositions of the present invention comprise a transfer vehicle wherein the mRNA is associated on both the surface of the transfer vehicle and encapsulated within the same transfer vehicle. For example, during preparation of the compositions of the present invention, cationic liposomal transfer vehicles may associate with the mRNA through electrostatic interactions.

Bilayer membranes of the liposomes can also be formed by amphophilic polymers and surfactants (e.g., polymerosomes, niosomes, etc.). the process of incorporation of a desired mRNA into a liposome is often referred to as "loading". Exemplary methods are described in Lasic, et al., FEBS Lett., 312: 255-258, 1992, which is incorporated herein by reference. The liposome-incorporated nucleic acids may be completely or partially located in the interior space of the liposome, within the bilayer membrane of the liposome, or associated with the exterior surface of the liposome membrane. The incorporation of a nucleic acid into liposomes is also referred to herein as "encapsulation" wherein the nucleic acid is entirely contained within the interior space of the liposome. The purpose of incorporating a mRNA into a transfer vehicle, such as a liposome, is often to protect the nucleic acid from an environment which may contain enzymes or chemicals that degrade nucleic acids and/or systems or receptors that cause the rapid excretion of the nucleic acids. Accordingly, in some embodiments, a suitable delivery vehicle is capable of enhancing the stability of the mRNA contained therein and facilitate the delivery of mRNA to the target CNS cell or tissue.

Suitable liposomal delivery vehicles according to the present invention may be made in various sizes. In some embodiments, the size of a liposome is determined by the length of the largest diameter of the liposome particle. In some embodiments, a suitable liposomal delivery vehicle has a size no greater than about 250 nm (e.g., no greater than about 225 nm, 200 nm, 175 nm, 150 nm, 125 nm, 100 nm, 90 nm, 80 nm, 70 nm, 60 nm, 50 nm, or 40 nm). In some embodiments, a suitable liposomal delivery vehicle has a size ranging from about 40-100 nm (e.g., ranging from about 40-90 nm, about 40-80 nm, about 40-70 nm, about 40-60 nm, about 40-50 nm, about 50-100 nm, about 50-90 nm, about 50-80 nm, about 50-70 nm, about 50-60 nm, about 60-100 nm, about 60-90 nm, about 60-80 nm, about 60-70 nm, about 70-100 nm, about 70-90 nm, about 70-80 nm, about 80-100 nm, about 80-90 nm, or about 90-100 nm).

A variety of methods known in the art are available for sizing of a population of liposomal transfer vehicles. One such sizing method is described in U.S. Pat. No. 4,737,323, incorporated herein by reference. Sonicating a liposome suspension either by bath or probe sonication can produces a progressive size reduction down to desired small ULV. Homogenization is another method that relies on shearing energy to fragment large liposomes into smaller ones. In a typical homogenization procedure, MLV are recirculated through a standard emulsion homogenizer until selected liposome sizes. The size of the liposomal vesicles may be determined by quasi-electric light scattering (QELS) as described in Bloomfield, Ann. Rev. Biophys. Bioeng., 10:421-150 (1981), incorporated herein by reference. Average liposome diameter may be reduced by sonication of formed liposomes. Intermittent sonication cycles may be alternated with QELS assessment to guide efficient liposome synthesis.

CNS Delivery mRNAs or mRNA containing deliver vehicles (e.g., mRNA loaded lipid nanoparticles) as described herein, are suitable for CNS deliver. In some embodiments, mRNA loaded lipid nanoparticles can be delivered to the CNS via various techniques and routes including, but not limited to, intraparenchymal, intracerebral, intravetricular cerebral (ICV), intrathecal (e.g., IT-Lumbar, IT-cisterna magna) administrations and any other techniques and routes for injection directly or indirectly to the CNS and/or CSF.

Intrathecal Delivery

In some embodiments, mRNA loaded lipid nanoparticles are delivered to the CNS by injecting into the cerebrospinal fluid (CSF) of a subject in need of treatment. In some embodiments, intrathecal administration is used for injecting mRNA or mRNA loaded nanoparticles to the CSF. As used herein, intrathecal administration (also referred to as intrathecal injection) refers to an injection into the spinal canal (intrathecal space surrounding the spinal cord). Various techniques may be used including, without limitation, lateral cerebroventricular injection through a burrhole or cisternal or lumbar puncture or the like. Exemplary methods are described in Lazorthes et al. Advances in Drug Delivery Systems and Applications in Neurosurgery, 143-192 and Omaya et al., Cancer Drug Delivery, 1: 169-179, the contents of which are incorporated herein by reference.

According to the present invention, mRNA or mRNA loaded nanoparticles may be injected at any region surrounding the spinal canal. In some embodiments, mRNA or mRNA loaded nanoparticles are injected into the lumbar area or cisterna magna or intraventricularly into a cerebral ventricle space. As used herein, the term "lumbar region" or "lumbar area" refers to the area between the third and fourth lumbar (lower back) vertebrae and, more inclusively, the L2-S1 region of the spine. Typically, intrathecal injection via the lumbar region or lumber area is also referred to as "lumbar IT delivery" or "lumbar IT administration." The term "cisterna magna" refers to the space around and below the cerebellum via the opening between the skull and the top of the spine. Typically, intrathecal injection via cisterna magna is also referred to as "cisterna magna delivery." The term "cerebral ventricle" refers to the cavities in the brain that are continuous with the central canal of the spiral cord. Typically, injections via the cerebral ventricle cavities are referred to as intravetricular Cerebral (ICV) delivery.

In some embodiments, "intrathecal administration" or "intrathecal delivery" according to the present invention refers to lumbar IT administration or delivery, for example, delivered between the third and fourth lumbar (lower back) vertebrae and, more inclusively, the L2-S1 region of the spine.

In some embodiments, intrathecal administration may be performed by either lumbar puncture (i.e., slow bolus) or via a port-catheter delivery system (i.e., infusion or bolus). In some embodiments, the catheter is inserted between the laminate of the lumbar vertebrae and the tip is threaded up the thecal space to the desired level (generally L3-L4).

Administration

The present invention contemplate single as well as multiple administrations of a therapeutically effective amount of mRNA or mRNA loaded nanoparticles described herein. mRNA or mRNA loaded nanoparticles can be administered at regular intervals, depending on the nature, severity and extent of the subject's CNS disease or condition. In some embodiments, a therapeutically effective amount of mRNA or mRNA loaded nanoparticles may be administered intrathecally periodically at regular intervals (e.g., once every year, once every six months, once every five months, once every three months, bimonthly (once every two months), monthly (once every month), biweekly (once every two weeks), weekly, daily or continuously).

In some embodiments, the CNS disease is associated with peripheral symptoms. Thus, in some embodiments, intrathecal administration may be used in conjunction with other routes of administration (e.g., intravenous, subcutaneously, intramuscularly, parenterally, transdermally, or transmucously (e.g., orally or nasally).

As used herein, the term "therapeutically effective amount" is largely determined base on the total amount of mRNA contained in the pharmaceutical compositions of the present invention. Generally, a therapeutically effective amount is sufficient to achieve a meaningful benefit to the subject (e.g., treating, modulating, curing, preventing and/or ameliorating the underlying disease or condition). For example, a therapeutically effective amount may be an amount sufficient to achieve a desired therapeutic and/or prophylactic effect. Generally, the amount of mRNA administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays may optionally be employed to identify optimal dosage ranges.

In some embodiments, a therapeutically effective dose ranges from about 0.001 mg/kg body weight to 10 mg/kg body weight, from about 0.005 mg/kg body weight to 10 mg/kg body weight, from about 0.01 mg/kg body weight to 10 mg/kg body weight, from about 0.01 mg/kg body weight to 9 mg/kg body weight, from about 0.01 mg/kg body weight to 8 mg/kg body weight, from about 0.01 body weight to 7 mg/kg body weight, from about 0.01 mg/kg body weight to 6 mg/kg body weight, from about 0.01 mg/kg body weight to 5 mg/kg body weight, from about 0.01 mg/kg body weight to 4 mg/kg body weight, from about 0.01 mg/kg body weight to 3 mg/kg body weight, from about 0.01 mg/kg body weight to 2 mg/kg body weight, from about 0.01 mg/kg body weight to 1 mg/kg body weight, from about 0.01 mg/kg body weight to 0.5 mg/kg body weight, from about 0.1 mg/kg body weight to 10 mg/kg body weight, from about 0.1 mg/kg body weight to 5 mg/kg body weight, from about 0.5 mg/kg body weight to 10 mg/kg body weight, or from about 0.5 mg/kg body weight to 5 mg/kg body weight.

In some embodiments, a therapeutically effective dose ranges from about 0.001 mg/kg brain weight to 100 mg/kg brain weight, from about 0.001 mg/kg brain weight to 90 mg/kg brain weight, from about 0.001 mg/kg brain weight to 80 mg/kg brain weight, from about 0.001 mg/kg brain weight to 70 mg/kg brain weight, from about 0.001 mg/kg brain weight to 60 mg/kg brain weight, from about 0.001 mg/kg brain weight to 50 mg/kg brain weight, from about 0.001 mg/kg brain weight to 40 mg/kg brain weight, from about 0.001 mg/kg brain weight to 30 mg/kg brain weight, from about 0.001 mg/kg brain weight to 20 mg/kg brain weight, from about 0.001 mg/kg brain weight to 10 mg/kg brain weight, from about 0.001 mg/kg brain weight to 5 mg/kg brain weight, from about 0.001 mg/kg brain weight to 1 mg/kg brain weight, from about 0.01 mg/kg brain weight to 100 mg/kg brain weight, from about 0.05 mg/kg brain weight to 100 mg/kg brain weight, from about 0.1 mg/kg brain weight to 100 mg/kg brain weight, or from about 0.5 mg/kg brain weight to 100 mg/kg brain weight.

As one skilled in the art would appreciate, the brain weights and body weights can be correlated. Dekaban A S. "Changes in brain weights during the span of human life: relation of brain weights to body heights and body weights," Ann Neurol 1978; 4:345-56. Thus, in some embodiments, the dosages can be converted as shown in Table 5.

TABLE 5

Correlation between Brain Weights body weights and ages of males

| Age (year) | Brain weight (kg) | Body weight (kg) |
|---|---|---|
| 3 (31-43 months) | 1.27 | 15.55 |
| 4-5 | 1.30 | 19.46 |

Delivery to Neurons and Other Cell Types in the Brain and/or Spinal Cord

Inventive methods according to the present invention result in delivery of mRNA in various neurons and other cell types in the brain and/or spinal cord. In some embodiments, mRNA encoding a therapeutic protein is delivered to various cells in the brain including, but not limited to, neurons, glial cells, perivascular cells and/or meningeal cells. In particular, inventive methods according to the present invention result in delivery of mRNA in various neurons and other cell types affected by a CNS disease and/or deficiency, or various neurons and other cell types in which the deficient protein associated with the CNS disease is normally expressed. In some embodiments, inventive methods according to the present invention result in delivery of mRNA in various neurons and other cell types in the CNS in which there is a detectable or abnormally high amount of enzyme substrate, for example stored in the cellular lysosomes of the tissue, in patients suffering from or susceptible to the lysosomal storage disease. In some embodiments, inventive methods according to the present invention result in delivery of mRNA in various neurons and other cell types that display disease-associated pathology, symptom, or feature. For example, mRNA may be delivered to neurons or other cell types that are deteriorating, degenerating or undergoing apoptosis such as those neurons or non-neuronal cells associated with neurodenegrative diseases (e.g., Alzheimer's disease, Parkinson's disease, and Huntington's disease) or motor neurons associated with motor neuron diseases (e.g., Amyotrophic Lateral Sclerosis (ALS), Primary Lateral Sclerosis (PLS), Pseudobulbar Pasly, Hereditary Spastic Paraplegia, Progressive Muscular Atrophy (PMA), Progressive Bulbar Palsy (PBP), Distal Hereditary Motor Neuropathies, and Spinal Muscular Atrophies).

In some embodiments, mRNA is delivered to neurons and/or non-neuronal cells located within the brain. In some embodiments, mRNA is delivered to neurons and/or non-neuronal cells located within the spinal cord. In some embodiments, mRNA is delivered to motor neurons. In some embodiments, the mRNA is delivered to upper motor neurons and/or lower motor neurons. In some embodiments, the motor neurons are located within the anterior horn and/or dorsal root ganglia of the spinal cord.

In some embodiments, mRNA is delivered intracellularly in various neurons and other cell types in the brain and/or spinal cord. In some embodiments, mRNA is delivered to the axons of neurons. In some embodiments, mRNA delivery according to the present invention results in intracellular expression of the protein encoded by the mRNA within cytosol of the neurons. In some embodiments, mRNA delivery according to the present invention results in expression of the protein encoded by the mRNA in subcellular compartment of the neurons, e.g., lysosomes, mitochondria, transmembrane, and the like. In some embodiments, mRNA delivery according to the present invention results in expression of the protein encoded by the mRNA and secretion extracellularly from the neurons.

Additional exemplary neurons and other cell types in the brain and/or spinal cord are described below.

Brain

In general, inventive methods according to the present invention can be used to deliver mRNA and encoded protein to neurons and other cell types in various regions of the brain. Typically, brain can be divided into different regions, layers and tissues. For example, meningeal tissue is a system of membranes which envelops the central nervous system, including the brain. The meninges contain three layers, including dura mater. arachnoid mater, and pia mater. In general, the primary function of the meninges and of the cerbrospinal fluid is to protect the central nervous system. In some embodiments, mRNA and the encoded protein is delivered to neurons or non-neuronal cells in one or more layers of the meninges.

The brain has three primary subdivisions, including the cerebrum, cerebellum, and brain stem. The cerebral hemispheres, which are situated above most other brain structures, are covered with a cortical layer. Underneath the cerebrum lies the brainstem, which resembles a stalk on which the cerebrum is attached. At the rear of the brain, beneath the cerebrum and behind the brainstem, is the cerebellum.

The diencephalon, which is located near the midline of the brain and above the mesencephalon, contains the thalamus, metathalamus, hypothalamus, epithalamus, prethalamus, and pretectum. The mesencephalon, also called the midbrain, contains the tectum, tegumentum, ventricular mesocoelia, and cerebral peduncels, the red nucleus, and the cranial nerve III nucleus. The mesencephalon is associated with vision, hearing, motor control, sleep/wake, alertness, and temperature regulation.

In some embodiments, mRNA and the encoded protein is delivered to neurons and/or non-neuronal cells of one or more tissues of the cerebellum. In certain embodiments, the targeted one or more tissues of the cerebellum are selected from the group consisting of tissues of the molecular layer, tissues of the Purkinje cell layer, tissues of the Granular cell layer, cerebellar peduncles, and combination thereof. In some embodiments, mRNA and the encoded protein is delivered to one or more deep tissues of the cerebellum including, but not limited to, tissues of the Purkinje cell layer, tissues of the Granular cell layer, deep cerebellar white matter tissue (e.g., deep relative to the Granular cell layer), and deep cerebellar nuclei tissue.

In some embodiments, mRNA and the encoded protein is delivered to one or more tissues of the brainstem.

In some embodiments, mRNA and encoded protein is delivered to various brain tissues including, but not limited to, gray matter, white matter, periventricular areas, pia-arachnoid, meninges, neocortex, cerebellum, deep tissue in cerebral cortex, molecular layer, caudate/putamen region, midbrain, deep regions of the pons or medulla, and combinations thereof. In some embodiments, mRNA and encoded protein is delivered to oligodendrocytes of deep white matter.

Spinal Cord

In some embodiments, inventive methods according to the present invention can be used to deliver mRNA and encoded protein to neurons and other cell types in various regions of the spinal cord. In general, regions or tissues of the spinal cord can be characterized based on the depth of the tissues. For example, spinal cord tissues can be characterized as surface or shallow tissues, mid-depth tissues, and/or deep tissues.

In some embodiments, mRNA and the encoded protein is delivered to one or more surface or shallow tissues of the spinal cord. In some embodiments, a targeted surface or shallow tissue of the spinal cord contains pia mater and/or the tracts of white matter.

In some embodiments, mRNA and the encoded protein is delivered to one or more deep tissues of the spinal cord. In some embodiments, a targeted deep tissue of the spinal cord contains spinal cord grey matter and/or ependymal cells.

The invention will be more fully understood by reference to the following examples. They should not, however, be construed as limiting the scope of the invention. All literature citations are incorporated by reference.

EXAMPLES

Example 1. Formulations and Messenger RNA Material

This example provides exemplary liposome formulations for effective delivery and expression of mRNA in the CNS. In general, the formulations described herein include a multi-component lipid mixture of varying ratios employing one or more cationic lipids, neutral lipids, cholesterol and/or PEGylated lipids designed to encapsulate various nucleic acid-based materials.

Messenger RNA Material

Codon-optimized human Survival of Motor Neuron-1 (hSMN-1) messenger RNA was synthesized by in vitro transcription from a plasmid DNA template encoding the gene, which was followed by the addition of a 5' cap structure (Cap 1) (Fechter, P.; Brownlee, G. G. "Recognition of mRNA cap structures by viral and cellular proteins" J. Gen. Virology 2005, 86, 1239-1249) and a 3' poly(A) tail of approximately 250 nucleotides in length as determined by gel electrophoresis. The 5' and 3' untranslated regions present in each mRNA product are represented as X and Y, respectively and defined as stated.
Survival of Motor Neuron (hSMN-1) mRNA:
X—SEQ ID NO:3—Y.
5' and 3' UTR Sequences
X (5'UTR Sequence)=

(SEQ ID NO: 7)
GGACAGAUCGCCUGGAGACGCCAUCCACGCUGUUUUGACCUCCAUAGAAG

ACACCGGGACCGAUCCAGCCUCCGCGGCCGGGAACGGUGCAUUGGAACGC

GGAUUCCCCGUGCCAAGAGUGACUCACCGUCCUUGACACG

Y (3' UTR Sequence)=

(SEQ ID NO: 8)
CGGGUGGCAUCCCUGUGACCCCUCCCCAGUGCCUCUCCUGGCCCUGGAAG

UUGCCACUCCAGUGCCCACCAGCCUUGUCCUAAUAAAAQUAAGUUGCAUC

AAGCU

OR (SEQ ID NO: 9)
GGGUGGCAUCCCUGUGACCCCUCCCCAGUGCCUCUCCUGGCCCUGGAAGU

UGCCACUCCAGUGCCCACCAGCCUUGUCCUAAUAAAAUUAAGUUGCAUCA

AAGCU

For example, the codon-optimized human Survival of Motor Neuron-1 (hSMN-1) messenger RNA comprises:

(SEQ ID NO: 10)
GGACAGAUCGCCUGGAGACGCCAUCCACGCUGUUUUGACCUCCAUAGAAG

ACACCGGGACCGAUCCAGCCUCCGCGGCCGGGAACGGUGCAUUGGAACGC

GGAUUCCCCGUGCCAAGAGUGACUCACCGUCCUUGACACGAUGGCCAUGA

GCAGCGGAGGCAGCGGCGGAGGAGUGCCCGAGCAGGAGGACAGCGUGCUG

UUCAGGAGAGGCACCGGCCAGAGCGAUGACAGCGAUAUCUGGGACGAUAC

CGCUCUGAUCAAGGCCUACGACAAGGCCGUGGCCAGCUUCAAGCACGCCC

UGAAAAACGGCGACAUCUGCGAGACCAGCGGCAAGCCCAAGACAACCCCC

AAGAGAAAGCCCGCCAAGAAGAAUAAGAGCCAGAAAAAGAACACCGCCGC

CAGCCUGCAGCAGUGGAAGGUGGGCGACAAGUGCAGCGCCAUCUGGAGCG

AGGACGGCUGCAUCUACCCCGCCACCAUCGCCAGCAUCGACUUCAAGAGA

GAGACCUGCGUGGUCGUGUACACCGGCUACGGCAACAGAGAGGAGCAGAA

CCUGAGCGACCUGCUGAGCCCCAUUUGUGAGGUGGCCAAUAACAUCGAAC

AGAACGCCCAGGAGAACGAGAAUGAAAGCCAGGUGAGCACCGACGAGAGC

GAGAACAGCAGAUCUCCUGGCAACAAGAGCGACAACAUCAAGCCUAAGUC

UGCCCCUUGGAACAGCUUCCUGCCCCUCCUCCACCCAUGCCCGGACCCA

GACUGGGACCCGGAAAACCUGGCCUGAAGUUCAACGGACCACCUCCCCCU

CCACCUCCUCCCCCACCUCAUCUCCUGAGCUGCUGGCUGCCACCCUUCCC

CAGCGGACCCCCUAUCAUCCCACCACCCCCUCCCAUCUGCCCCGACAGCC

UGGACGACGCCGAUGCCCUGGGCAGCAUGCUGAUCAGCUGGUACAUGAGC

GGCUACCACACAGGAUACUACAUGGGCUUCAGACAGAACCAGAAGGAGGG

CAGAUGCUCCCACUCCCUGAACUGACGGGUGGCAUCCCUGUGACCCCUCC

CCAGUGCCUCUCCUGGCCCUGGAAGUUGCCACUCCAGUGCCCACCAGCCU

UGUCCUAAUAAAAUUAAGUUGCAUCAAGCU or the codon-optimized human Survival of Motor Neuron-1 (hSMN-1) messenger RNA comprised:

(SEQ ID NO: 11)
GGACAGAUCGCCUGGAGACGCCAUCCACGCUGUUUUGACCUCCAUAGAAG

ACACCGGGACCGAUCCAGCCUCCGCGGCCGGGAACGGUGCAUUGGAACGC

GGAUUCCCCGUGCCAAGAGUGACUCACCGUCCUUGACACGAUGGCCAUGA

GCAGCGGAGGCAGCGGCGGAGGAGUGCCCGAGCAGGAGGACAGCGUGCUG

UUCAGGAGAGGCACCGGCCAGAGCGAUGACAGCGAUAUCUGGGACGAUAC

CGCUCUGAUCAAGGCCUACGACAAGGCCGUGGCCAGCUUCAAGCACGCCC

UGAAAAACGGCGACAUCUGCGAGACCAGCGGCAAGCCCAAGACAACCCCC

-continued

AAGAGAAAGCCCGCCAAGAAGAAUAAGAGCCAGAAAAAGAACACCGCCGC

CAGCCUGCAGCAGUGGAAGGUGGGCGACAAGUGGAGCGCCAUCUGGAGCG

AGGACGGCUGCAUCUACCCCGCCACCAUCGCCAGCAUCGACUUCAAGAGA

GAGACCUGCGUGGUCGUGUACACCGGCUACGGCAACAGAGAGGAGCAGAA

CCUGAGCGACCUGCUGAGCCCCAUUUGUGAGGUGGCCAAUAACAUCGAAC

AGAACGCCCAGGAGAACGAGAAUGAAAGCCAGGUGAGCACCGACGAGAGC

GAGAACAGCAGAUCUCCUGGCAACAAGAGCGACAACAUCAAGCCUAAGUC

UGCCCCUUGGAACAGCUUCCUGCCCCCUCCUCCACCCAUGCCCGGACCCA

GACUGGGACCCGGAAAACCUGGCCUGAAGUUCAACGGACCACCUCCCCCU

CCACCUCCUCCCCCACCUCAUCUCCUGAGCUGCUGGCUGCCACCCUUCCC

CAGCGGACCCCCUAUCAUCCCACCACCCCCUCCCAUCUGCCCCGACAGCC

UGGACGACGCCGAUGCCCUGGGCAGCAUGCUGAUCAGCUGGUACAUGAGC

GCCUACCACACAGGAUACUACAUGGGCUUCAGACAGAACCAGAAGGAGGG

CAGAUGCUCCCACUCCCUGAACUGAGGGUGGCAUCCCUGUGACCCCUCCC

CAGUGCCUCUCCUGGCCCUGGAAGUUGCCACUCCAGUGCCCACCAGCCUU

GUCCUAAUAAAAUUAAGUUGCAUCAAAGCU.

Exemplary Formulation Protocol

Lipid nanoparticles (LNP) were formed via standard ethanol injection methods (Ponsa, M.; Foradada, M.; Estelrich, J. "Liposomes obtained by the ethanol injection method" *Int. J. Pharm.* 1993, 95, 51-56). For the various lipid components, a 50 mg/ml ethanolic stock solutions was prepared and stored at −20° C. In preparation of each exemplary formulation listed in Table 5 below, the indicated lipid components were added to an ethanol solution to achieve a predetermined final concentration and molar ratio, and scaled to a 3 ml final volume of ethanol. Separately, an aqueous buffered solution (10 mM citrate/150 mM NaCl, pH 4.5) of hSMN-1 mRNA was prepared from a 1 mg/ml stock. The lipid solution was injected rapidly into the aqueous mRNA solution, either manually or via syringe pump, and shaken to yield a final suspension in 20% ethanol. The resulting nanoparticle suspension was filtered and dialysed against 1× PBS (pH 7.4), concentrated and stored between 2-8° C. SMN-1 mRNA concentration was determined via the Ribogreen assay (Invitrogen). Encapsulation of mRNA was calculated by performing the Ribogreen assay with and without the presence of 0.1% Triton-X 100. Particle sizes (dynamic light scattering (DLS)) and zeta potentials were determined using a Malvern Zetasizer instrument 1× PBS and 1 mM KCl solutions, respectively.

TABLE 6

Exemplary Lipid Nanoparticle Formulations

| Formulations | Components | Molar Ratio of lipids | Final mRNA Concentration | Zeta Parameters |
|---|---|---|---|---|
| 1 | C12-200 DOPE Cholesterol DMG-PEG2K hSMN-1 mRNA | 40:30:25:5 | 2.5 mg/ml | $Z_{ave}$ = 82 nm; $Dv_{(50)}$ = 53 nm; $Dv_{(90)}$ = 97 nm |
| 2 | C12-200 Sphingomyelin DOPE Cholesterol DMG-PEG-2K hSMN-1 mRNA | 40:15:20:20:5 | 1.28 mg/ml | $Z_{ave}$ = 90 nm; $Dv_{(50)}$ = 75 nm; $Dv_{(90)}$ = 104 nm |
| 3 | DLin-KC2-DMA DOPE Cholesterol DMG-PEG-2K hSMN-1mRNA | 40:30:25:5 | 2.05 mg/ml | $Z_{ave}$ = 72 nm; $Dv_{(50)}$ = 48 nm; $Dv_{(90)}$ = 85 nm |
| 4 | cKK-E12 DOPE Cholesterol DMG-PEG-2K hSMN-1 mRNA | 40:30:25:5 | 1.85 mg/ml | $Z_{ave}$ = 71 nm; $Dv_{(50)}$ = 44 nm; $Dv_{(90)}$ = 93 nm |
| 5 | cKK-E12 DOPE Cholesterol DMG-PEG-5K hSMN-1 mRNA | 40:30:25:5 | 1.8 mg/ml | $Z_{ave}$ = 72 nm; $Dv_{(50)}$ = 49 nm; $Dv_{(90)}$ = 90 nm |
| 6 | Re-1 DOPE Cholesterol DMG-PEG-SK hSMN-1 mRNA | 40:30:25:5 | 1.8 mg/ml | $Z_{ave}$ = 81 nm; $Dv_{(50)}$ = 66 nm; $Dv_{(90)}$ = 97 nm |
| 7 | HGT5001 DOPE Cholesterol DMG-PEG-5K hSMN-1 mRNA | 40:30:25:5 | 1.5 mg/ml | $Z_{ave}$ = 82 nm; $Dv_{(50)}$ = 53 nm; $Dv_{(90)}$ = 99 nm |
| 8 | ICE DOPE Cholesterol DMG-PEG-5K hSMN-1 mRNA | 40:30:25:5 | 1.96 mg/ml | $Z_{ave}$ = 63 nm; $Dv_{(50)}$ = 41 nm; $Dv_{(90)}$ = 83 nm |
| 9 | HGT4003 DOPE Cholesterol DMG-PEG-SK hSMN-1 mRNA | 40:30:25:5 | 1.5 mg/ml | $Z_{ave}$ = 82 nm; $Dv_{(50)}$ = 53 nm; $Dv_{(90)}$ = 99 nm |
| 10 | DODMA DOPE Cholesterol DMG-PEG-5K hSMN-1 mRNA | 40:30:25:5 | 1.6 mg/ml | $Z_{ave}$ = 78 mm; $Dv_{(50)}$ = 49 nm; $Dv_{(90)}$ = 96 nm |
| 11 | cKK-EE12 DOPE Cholesterol DMO-PEG-2K DSPE-PBG-Maleimide-Lectin hSMN-1 mRNA | 40:30:25:2:3 | 14 mg/ml | $Z_{ave}$ = 95 mm; $Dv_{(50)}$ = 72 mm; $Dv_{(90)}$ = 103 nm |
| 12 | C12-200 DOPE Cholesterol DOG-PEG-2K hSMN-1 mRNA | 40:30:25:5 | 1.2 mg/ml | $Z_{ave}$ = 74 nm; $Dv_{(50)}$ = 50 nm; $Dv_{(90)}$ = 93 nm |
| 13 | cKK-EE12 Sphingomyelin DOPE Cholesterol DMG-PEG-2K hSMN-1 mRNA | 40:15:20:20:5 | 16 mg/ml | $Z_{ave}$ = 74 nm; $Dv_{(50)}$ = 41 nm; $Dv_{(90)}$ = 90 nm |

Example 2. Intrathecal Administration of mRNA Loaded Liposome Nanoparticles

This example illustrates exemplary methods of administering intrathecally mRNA-loaded liposome nanoparticles and methods for analyzing delivered mRNA in neurons.

All studies were performed with either rats or mice of approximately 6-8 weeks of age at the beginning of each experiment. At the start of the experiment, each animal was anesthetized with isoflurane (1-3%, to effect) by inhalation. Once anesthetized, each animal was shaved at the exact injection site (L4-L5 or L5-L6). Following insertion a the needle, reflective flick of the tail was used to indicate puncture of the dura and confirm intrathecal placement. Each animal received a single bolus intrathecal injection of one of the test formulations listed in Table 6. All animals were sacrificed 24 hours post injection and perfused with saline.

Isolation of Organ Tissues for Analysis

All animals had the whole brain and spinal cord harvested. The brain was cut longitudinally and placed in one histology cassette per animal. The whole spinal cord was stored ambient in a 15 ml tube containing 10% neutral buffered formalin (NBF) for at least 24 hours and no more than 72 hours before transfer into 70% histology grade alcohol solution. Each spinal cord sample was cut into cervical, thoracic and lumbar sections. Each spinal cord section cut in half and both halves were placed in individual cassettes per section (cervical, thoracic and lumbar) for processing. All three cassettes were embedded into one paraffin block per animal. When applicable, portions of brain and spinal cord were snap frozen and stored at −80° C.

hSMN-1 Western Blot Analysis

Standard western blot procedures were followed employing various antibodies that recognizes hSMN protein, such as: (A) anti-SMN 4F11 antibody at 1:1,000 dilution; (B) Pierce PA5-27309 a-SMN antibody at 1:1,000 dilution; and (C) LSBio C138149 a-SMN antibody at 1:1,000 dilution. For each experiment one microgram of hSMN mRNA was transfected into ~1×10$^6$ BHK-21 cells using Lipofectamine 2000. Cells were treated with OptiMem and harvested 16-18 hours post-transfection. Cell lysates were harvested, processed and loaded on to an 8-16% Tris Glycine gel. The gel was transferred using a PVDF membrane and treated with the respective primary antibody. Goat anti-mouse HRP antibody was used as the secondary antibody at 1:10,000 dilution for 45 minutes at room temperature followed by washing and development. The data demonstrates that each antibody tested showed a strong signal for hSMN-1 and was specific for human SMN, as indicated by an absence in a cross-reactive signal for untreated BHK cells (FIG. 1).

In Situ Hybridization (ISH) Analysis

Tissue from each representative sample, was assayed for hSMN-1 mRNA using two different in situ hybridization methods. For the first approach, manual in situ hybridization analysis was performed using RNAscope® (Advanced Cell Diagnostic) "ZZ" probe technology. Probes were generated based on the codon-optimized sequence of human SMN messenger RNA (SEQ ID NO:3). Briefly, the RNAscope® assay is an in situ hybridization assay designed to visualize single RNA molecules per cell in formalin-fixed, paraffin-embedded (FFPE) tissue mounted on slides. Each embedded tissue sample was pretreated according to the manufacturers protocol and incubated with a target specific hSMN-1 RNA probe. The hSMN-1 probe was shown to be specific for human SMN-1 and had little to no cross reactivity with mouse or rat SMN-1. Once bound, the hSMN-1 probe is hybridized to a cascade of signal amplification molecules, through a series of 6 consecutive rounds of amplification. The sample was then treated with an HRP-labeled probe specific to the signal amplification cassette and assayed by chromatic visualization using 3,3'-diaminobenzidine (DAB). A probe specific for Ubiquitin C was used as the positive control. Positive SMN signal was compared to that of untreated and vehicle control treated rat or mouse tissue. Stained samples were visualized under a standard bright field microscope.

Figure 17:
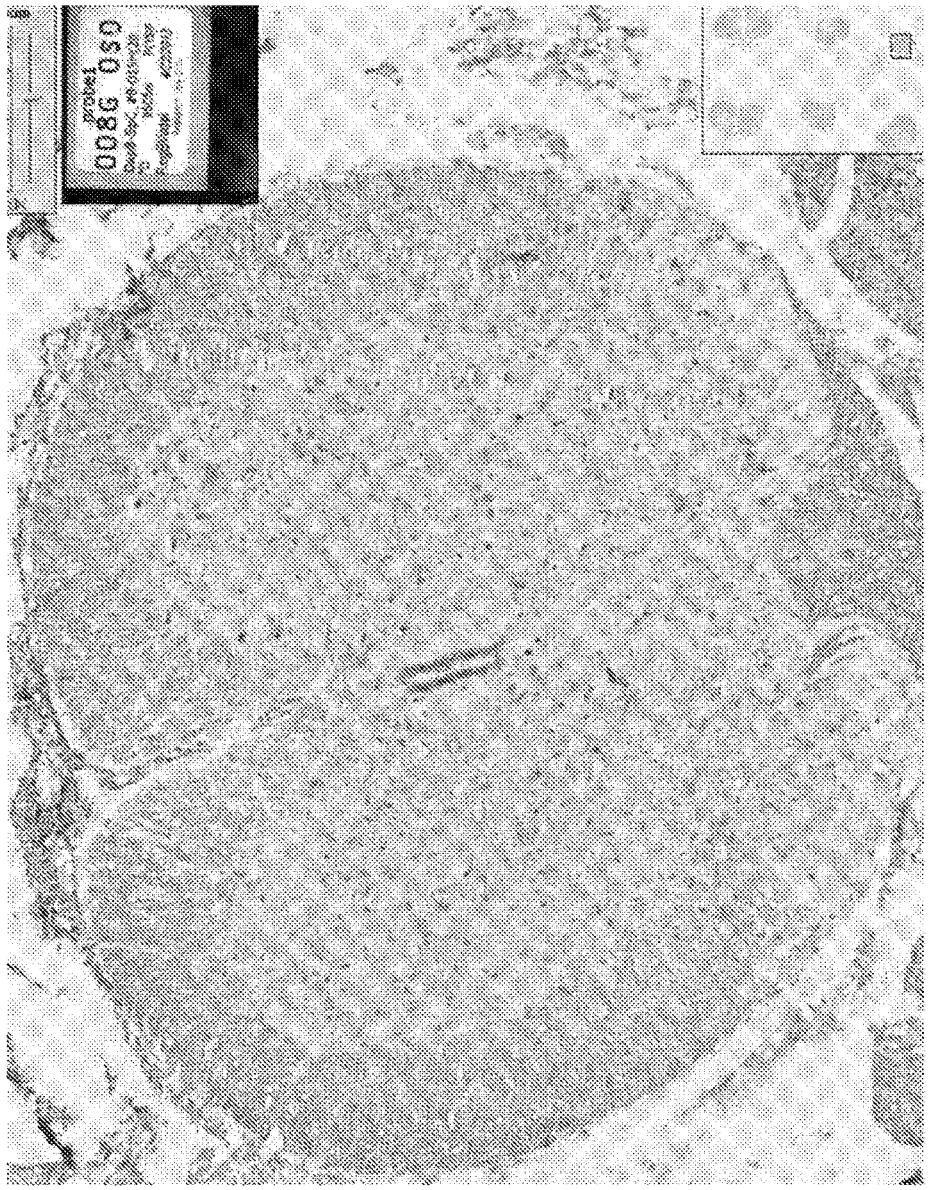
FIG. 17 illustrates in situ detection of UbC mRNA in spinal tissue, 24 hours post intrathecal delivery of vehicle control.
Figure 18:
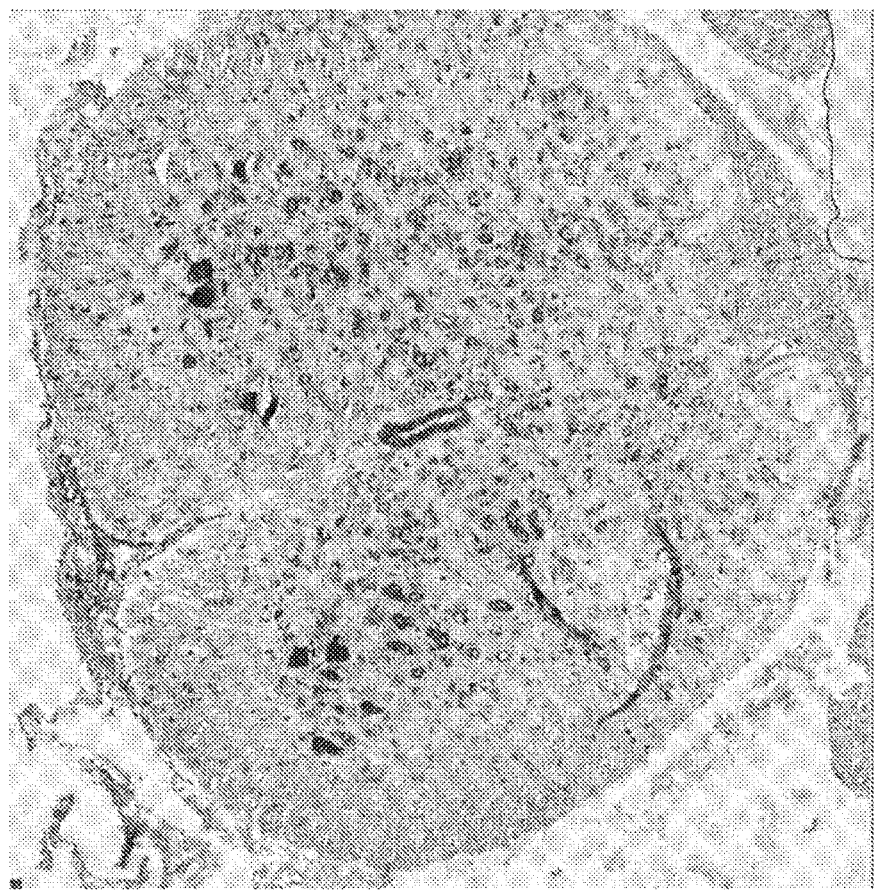
FIG. 18 illustrates in situ detection of human Survival Motor Neuron (hSMN-1) mRNA in spinal tissue, 24 hours post intrathecal delivery of vehicle control. Image is shown at 5× magnification.
Figure 19:
FIG. 19 illustrates in situ detection of human Survival Motor Neuron (hSMN-1) mRNA in spinal tissue, 24 hours post intrathecal delivery. Image is shown at 5× magnification.
Figure 20:
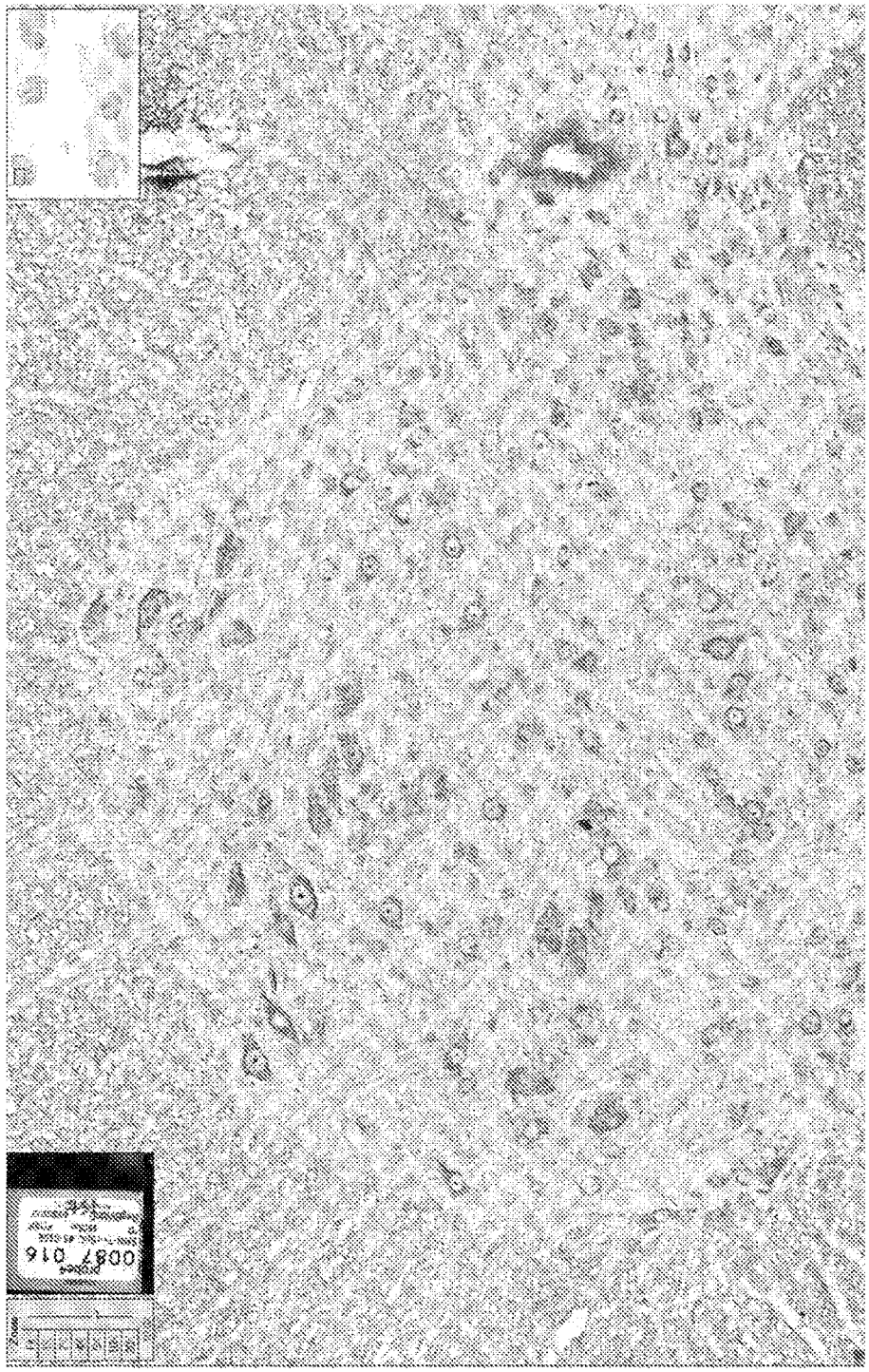
FIG. 20 illustrates in situ detection of human Survival Motor Neuron (hSMN-1) mRNA in spinal tissue, 24 hours post intrathecal delivery. Image is shown at 10× magnification.
Figure 21:
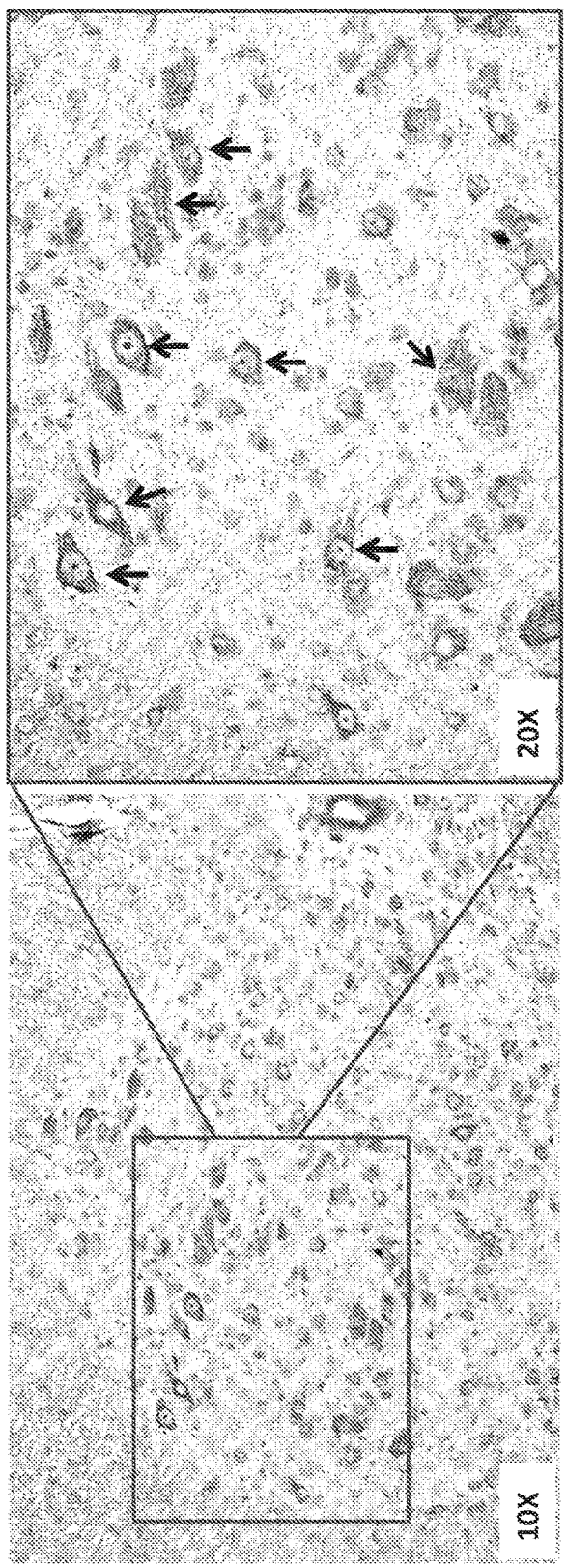
FIG. 21 illustrates in situ detection of human Survival Motor Neuron (hSMN-1) mRNA in spinal tissue, 24 hours post intrathecal delivery. Image is shown at 10× and 20× magnification.

For the second approach, a fully automated in situ hybridization analysis was performed using the Leica Bond Rx detection system. Probes were generated based on the codon-optimized sequence of human SMN messenger RNA (SEQ ID NO:3). Briefly, each embedded tissue sample was pretreated according to the manufacturers protocol and incubated with a target specific HRP-labeled hSMN-1 RNA probe. A Ubiquitin C probe was used as the positive control (FIG. 18) and a DapB probe was used as the negative probe control (FIG. 17). Hybridized was assayed using Fast-Red, a chromatic substrate for alkaline phosphatase.

Immunohistochemical Analysis

Figure 22:
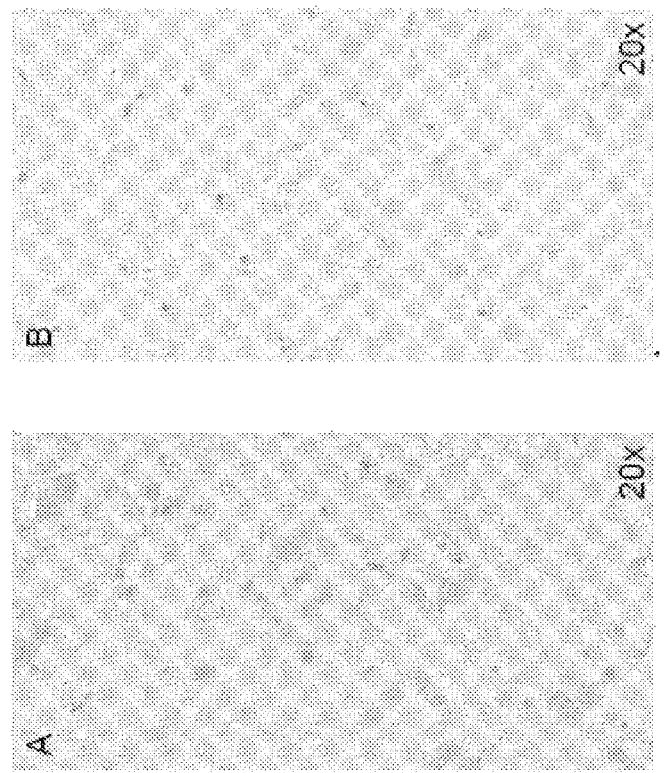
FIG. 22 illustrates positive detection of human SMN-1 protein produced in the spinal cord of a rat 24 hours post-intrathecal administration of human SMN-1 mRNA-loaded lipid nanoparticles. Anti-human SMN 4F11 antibody was employed at 1:2500 dilution. Panel A represents treated rat spinal cord tissue and panel B represents untreated rat spinal cord tissue.

Human SMN-1 mRNA-loaded lipid nanoparticles were administered to rats via intrathecal injection, and tissue samples collected and processed 24 hours post administration in accordance with the methods described above. Rat spinal tissue samples were then assayed for hSMN-1 protein expression. Briefly, fixed tissue embedded in paraffin was processed and placed on slides. The slides were dewaxed, rehydrated and antigen retrieval was performed using a pressure cooker with citrate buffer. Several blocking buffers were employed followed by primary antibody incubation overnight at 4° C., using the 4F11 antibody at a 1:2500 dilution. The resulting slides were washed and incubated at ambient temperature with the secondary antibody polymer followed by washing and subsequent chromagen development. The data demonstrates that in as little as 24 hours post intrathecal administration of hSMN-1 mRNA, staining is observed for human SMN-1 protein when compared to no-treatment control (FIG. 22). This supports the previous findings which demonstrate delivery of hSMN-1 mRNA to the spinal tissue. Furthermore, the data demonstrates that once delivered to the cell hSMN-1 mRNA is effectively expressed to generate hSMN-1 protein.

Example 3. Effective Intracellular Delivery of mRNA in Neurons

The data presented in this example demonstrates that intrathecal administration of hSMN-1 mRNA loaded liposomes (e.g., lipid or polymer-based nanoparticles) results in successful intracellular delivery of mRNA in neurons in the brain and spinal cord, including those difficult to treat cells, such as anterior horn cells and dorsal root ganglia.

Figure 15:
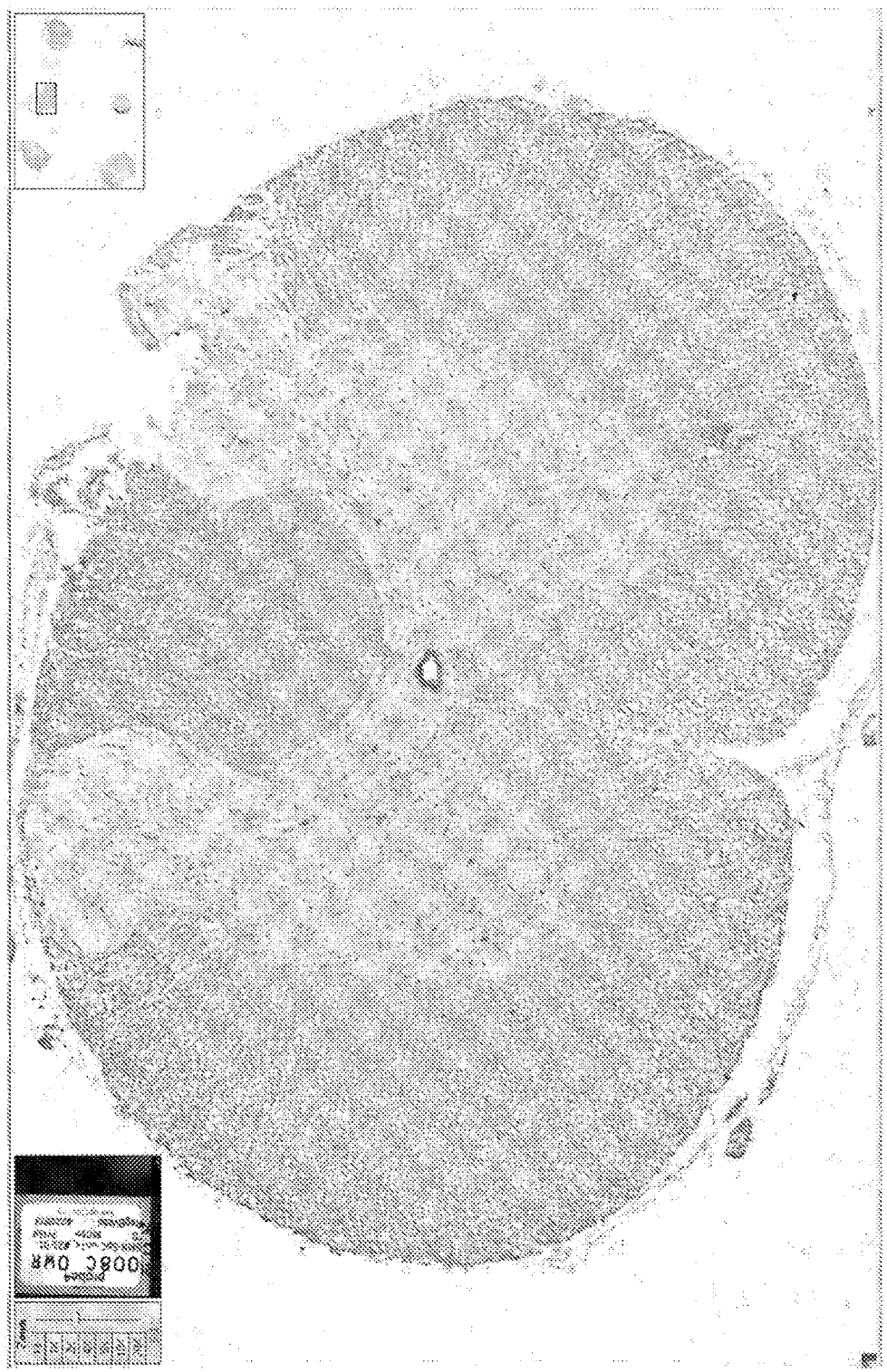
FIG. 15 illustrates in situ detection of human Survival Motor Neuron (hSMN-1) mRNA in spinal tissue, 24 hour post intrathecal delivery of vehicle control. Image is shown at 5× magnification.
Figure 16:
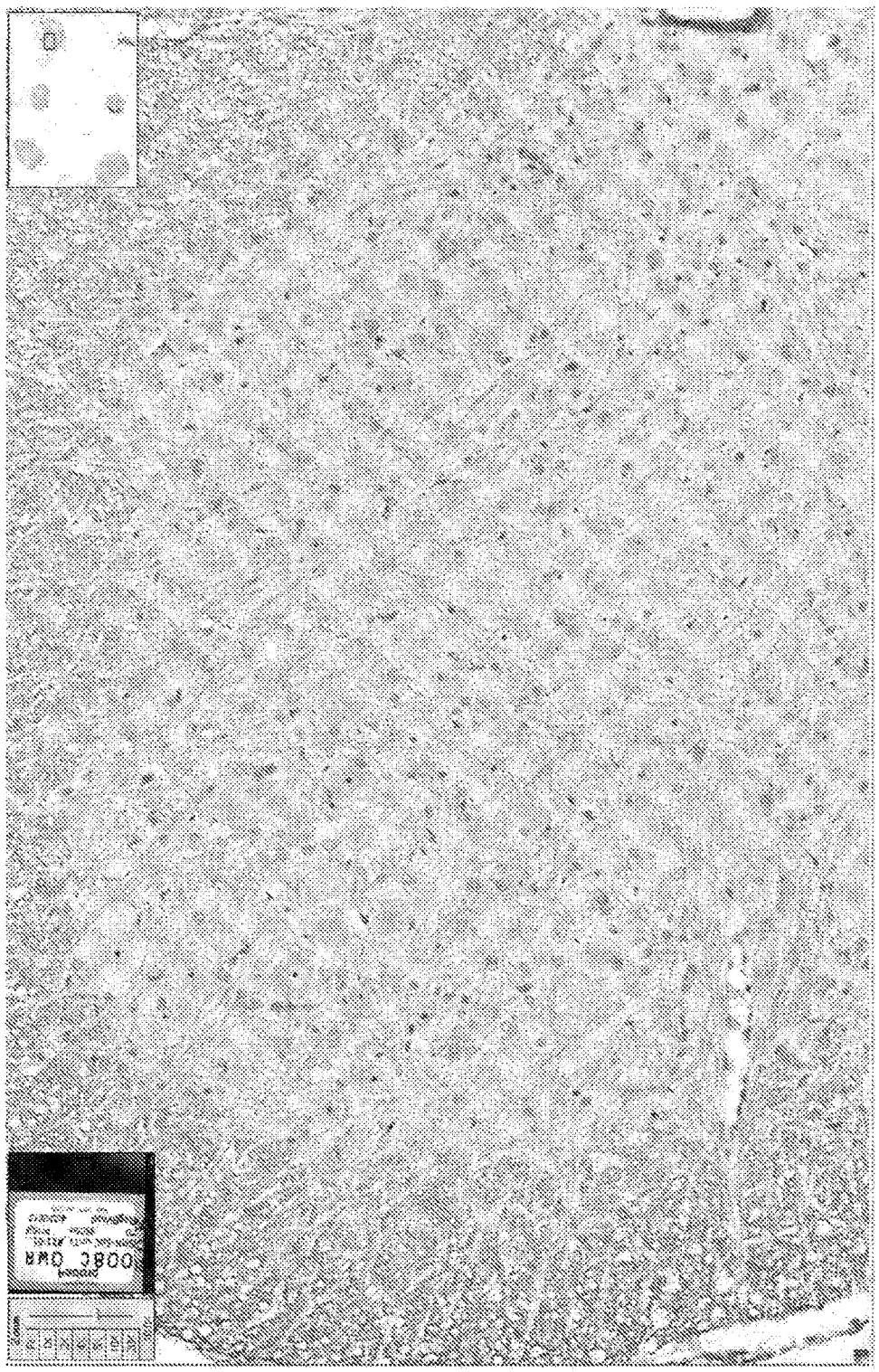
FIG. 16 illustrates in situ detection of human Survival Motor Neuron (hSMN-1) mRNA in spinal tissue, 24 hours post intrathecal delivery of vehicle control. Image is shown at 10× magnification.

The results have shown that mRNA encapsulated within a lipid nanoparticle can be effectively delivered to various tissues of the CNS following interthecal administrations. Using the thirteen different formulations disclosed in Table 6, mRNA was effectively delivered and internalized within various neurons of the spinal cord (FIGS. 2A-14C), as verified by two independent in situ hybridization assays. Surprisingly, intracellular mRNA delivery was demonstrated in the difficult to reach neuronal cells of the anterior horn, located deep within the tissues of the spinal column, were it was expressed as protein (FIGS. 19-22). Little to no background was observed with mouse or rat SMN-1, indicating specificity for the human SMN-1 probe (FIGS. 15-17). Positive SMN signal was compared to that of untreated and vehicle control treated rat or mouse tissue. Stained samples were visualized under a standard bright field microscope.

These data demonstrates that the lipid or polymer nanoparticle based mRNA delivery approach described herein were able to successfully permeate the complex and dense cell membrane of the spinal cord neurons and deliver the mRNA payload for the production of encoded proteins inside neurons. It was particularly surprising that the mRNA delivery approach described herein was equally successful in permeate those difficult to treat neurons such as anterior horn cell and dorsal root ganglia. Thus, the data presented herein demonstrates that lipid or polymer nanoparticles based mRNA delivery approach is a promising option for treating a CNS disease. In particular, the present invention demonstrates that hSMN mRNA loaded nanoparticles can be effectively delivered to neurons including those difficult to treat motor neurons in the spinal cord for the production of SMN protein and treatment of spinal muscular atrophy.

Example 4. Effective Intracellular Delivery of mRNA in Brain White and Grey Matter The data presented in this example demonstrate that intrathecal administration of hSMN-1 mRNA loaded liposomes (e.g., lipid or polymer-based nanoparticles) results in successful intracellular delivery of mRNA in neurons in the brain, including difficult to treat tissues located deep within the brain, such a white matter.

The study was performed with rats of approximately 6-8 weeks of age at the beginning of each experiment, using the methods and techniques described above. Briefly, at the start of the experiment, each animal was anesthetized with isoflurane (1-3%, to effect) by inhalation. Once anesthetized, each animal was shaved at the exact injection site (L4-L5 or L5-L6). Following insertion of the needle, reflexive flick of the tail was used to indicate puncture of the dura and confirm intrathecal placement. Each animal received a single bolus intrathecal injection of one of the test formulations listed in Table 6. All animals were sacrificed 30 minutes of 24 hours post injection and perfused with saline. The data presented in Example 4, demonstrate the results of mRNA delivery using formulation 13 of Table 6 above.

In Situ Hybridization (ISH) Analysis

Figure 23:
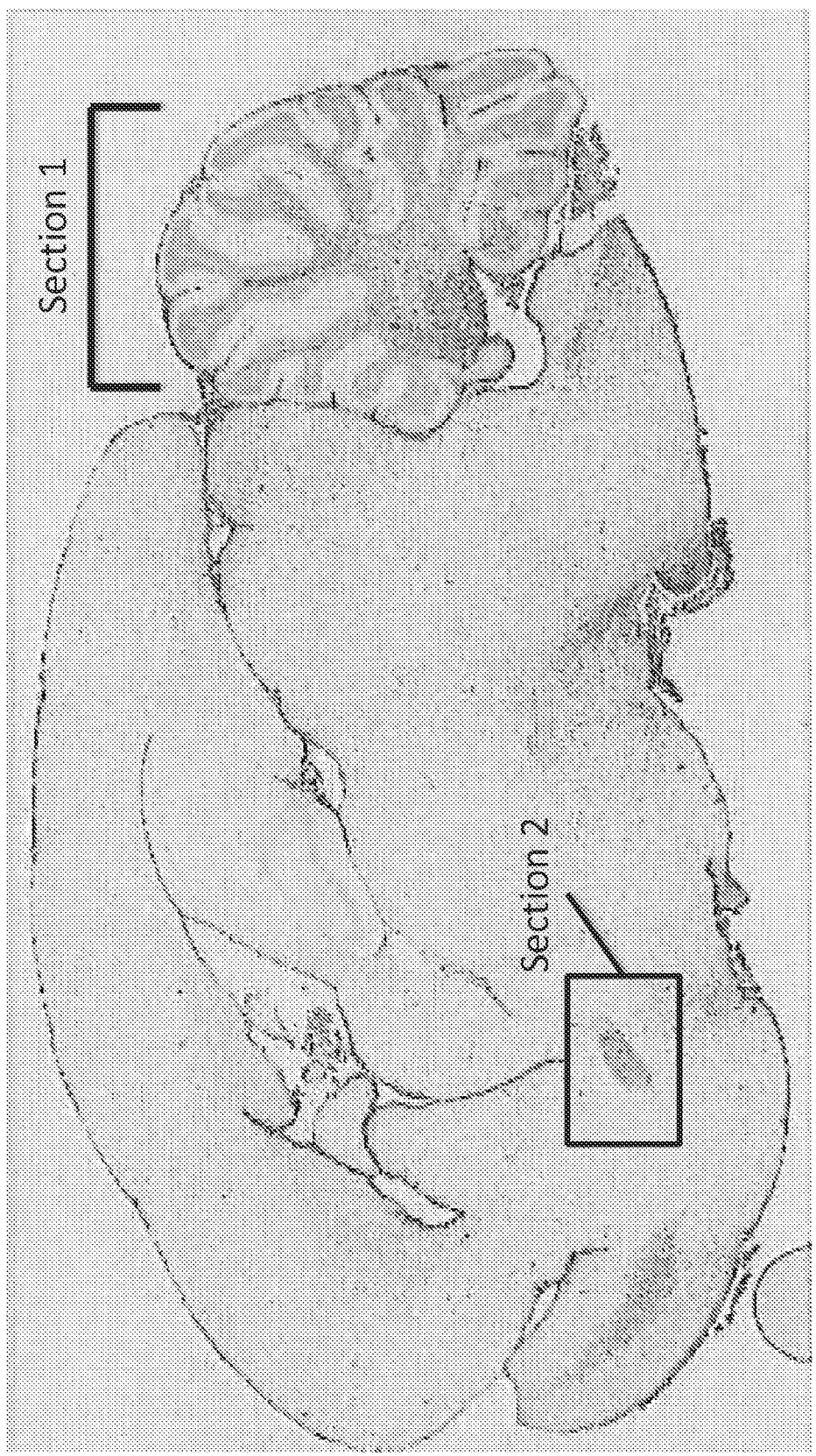
FIGS. 23A-C illustrates in situ detection of human Survival Motor Neuron (hSMN-1) mRNA in brain tissue, 30 minutes post intrathecal delivery. In situ detection of the brain (A) demonstrates a strong signal observed both within the gray and white matter of the brain. Two regions of the brain (B) Section 1 and (C) Section 2 were further magnified for closer analysis.
Figure 23B:
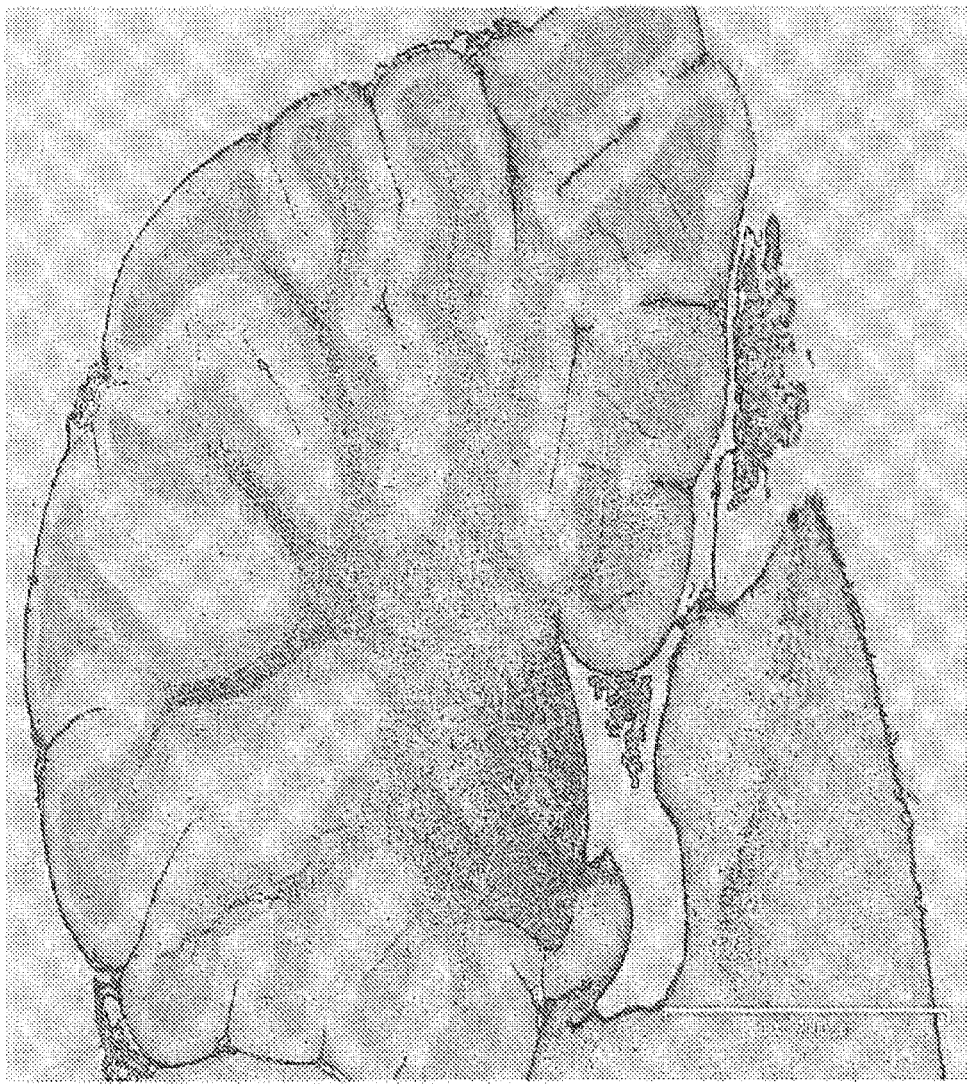

Human SMN-1 mRNA-loaded lipid nanoparticles were administered to rats via intrathecal injection, and tissue samples collected 30 min and 24 hours post administration, processed and assayed for hSMN-1 mRNA using RNAscope® (Advanced Cell Diagnostic) "ZZ" probe technology, as described above. Each embedded tissue sample was pretreated according to the manufacturers protocol and incubated with a target specific hSMN-1 RNA probe. The data demonstrates that in as little as 30 minutes post intrathecal administration of hSMN-1 mRNA, staining is observed for human SMN-1 mRNA throughout the tissue of the brain, compared to no-treatment control (FIG. 23A). This supports the previous findings and highlights the speed and effectiveness of the mRNA delivery method, which results in mRNA delivery in as little as 30 minutes post IT delivery. Furthermore, the data clearly demonstrates the surprising and unexpected discovery that mRNA delivery in accordance with the invention, results in effective mRNA delivery to both grey matter tissue (located at the external periphery of the brain) and white matter tissue (located deep within the brain). Thus suggesting that the current approach can serve as an viable therapy in treating neurological or neuromuscular diseases, which manifest as a result of dysregution of cells located deep within the hard to reach white matter tissue of the brain.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A composition for treating spinal muscular atrophy, comprising a codon optimized mRNA encoding the Survival of Motor Neuron (SMN) protein, encapsulated within a liposome; wherein the codon optimized mRNA comprises the full-length sequences of SEQ ID NO:3, SEQ ID NO: 4, SEQ ID NO: 10 or SEQ ID NO: 11, and further wherein the liposome comprises one or more cationic or non-cationic lipids, cholesterol-based lipids and polyethylene glycol (PEG)-modified lipids.

2. The composition of claim 1, wherein the one or more cationic lipids are selected from the group consisting of C12-200, MC3, DLinDMA, DLinkC2DMA, cKK-E12, ICE (Imidazol-based), HGT5000, HGT5001, DODAC, DDAB, DMRIE, DOSPA, DOGS, DODAP, DODMA, DLenDMA, CLinDMA, CpLinDMA, DMOBA, DOcarbDAP, DLinDAP, DLincarbDAP, DLinCDAP, DLin-KDMA, DLin-K-XTC2-DMA, HGT4003, and combinations thereof.

3. The composition of claim 1, wherein the cationic lipid is cKK-E12:

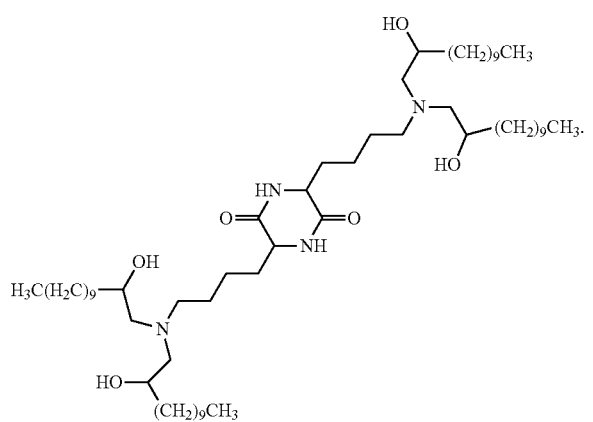

4. The composition of claim 1, wherein the one or more PEG-modified lipids constitute about 1-10% by molar ratio of the total lipid composition.

5. The composition of claim 1, wherein the liposome has a size ranging from about 40-100 nm.

6. The composition of claim 1, wherein the codon optimized mRNA has a length of or greater than about 0.5 kb, 1 kb, 1.5 kb, 2 kb, 2.5 kb, 3 kb, 3.5 kb, 4 kb, 4.5 kb, or 5 kb.

7. The composition of claim 1, wherein administration of the composition results in intracellular expression of the SMN protein within the cytosol of the neurons.

8. The composition of claim 1, wherein administration of the composition results in expression of the SMN protein and secretion extracellularly from the neurons after expression.

9. The composition of claim 1, wherein the codon optimized mRNA comprises one or more modified nucleotides.

10. The composition of claim 1, wherein the codon optimized mRNA is unmodified.

11. The composition of claim 1, wherein the amount of codon optimized mRNA is from about 0.01 mg/kg to about 10 mg/kg body weight of a subject.

12. The composition of claim 1, wherein administration of the composition results in expression of the SMN protein encoded by the codon optimized mRNA that is detectable in brain and/or spinal tissue at least 24 hours after administration.

13. A composition for treating spinal muscular atrophy, comprising a codon optimized mRNA encoding the Survival of Motor Neuron (SMN) protein, encapsulated within a liposome; wherein the codon optimized mRNA comprises the full-length sequences of SEQ ID NO:3, SEQ ID NO: 4, SEQ ID NO: 10 or SEQ ID NO: 11, and wherein the liposome comprises one or more cationic or non-cationic lipids, cholesterol-based lipids, polyethylene glycol (PEG)-modified lipids, and sphingomyelin.

14. The composition of claim 13, wherein the one or more cationic lipids are selected from the group consisting of C12-200, MC3, DLinDMA, DLinkC2DMA, cKK-E12, ICE (Imidazol-based), HGT5000, HGT5001, DODAC, DDAB, DMRIE, DOSPA, DOGS, DODAP, DODMA, DLenDMA, CLinDMA, CpLinDMA, DMOBA, DOcarbDAP, DLinDAP, DLincarbDAP, DLinCDAP, DLin-KDMA, DLin-K-XTC2-DMA, HGT4003, and combinations thereof.

15. The composition of claim 13, wherein the cationic lipid is cKK-E12:

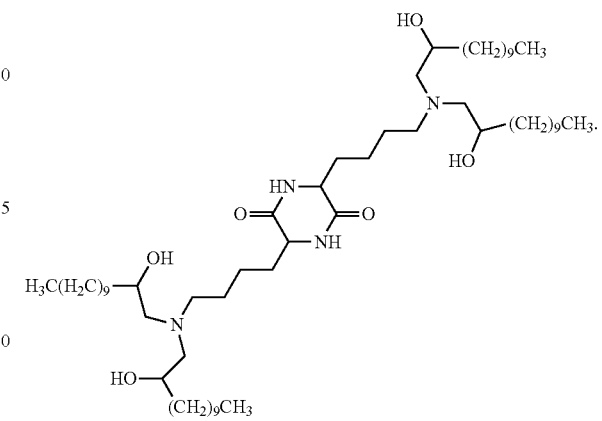

16. The composition of claim 13, wherein the one or more PEG-modified lipids constitute about 1-10% by molar ratio of the total lipid composition.

17. The composition of claim 13, wherein the liposome has a size ranging from about 40-100 nm.

18. The composition of claim 13, wherein the codon optimized mRNA has a length of or greater than about 0.5 kb, 1 kb, 1.5 kb, 2 kb, 2.5 kb, 3 kb, 3.5 kb, 4 kb, 4.5 kb, or 5 kb.

19. The composition of claim 13, wherein administration of the composition results in intracellular expression of the SMN protein within the cytosol of the neurons.

20. The composition of claim 13, wherein administration of the composition results in expression of the SMN protein and secretion extracellularly from the neurons after expression.

21. The composition of claim 13, wherein the codon optimized mRNA comprises one or more modified nucleotides.

22. The composition of claim 13, wherein the codon optimized mRNA is unmodified.

23. The composition of claim 13, wherein the amount of codon optimized mRNA is from about 0.01 mg/kg to about 10 mg/kg body weight of a subject.

24. The composition of claim 13, wherein administration of the composition results in expression of the SMN protein encoded by the codon optimized mRNA that is detectable in brain and/or spinal tissue at least 24 hours after administration.

* * * * *

SEQUENCE LISTING

```
<160> NUMBER OF SEQ ID NOS: 15

<210> SEQ ID NO 1
<211> LENGTH: 1511
<212> TYPE: RNA
<213> ORGANISM: Homo sapiens

<400> SEQUENCE: 1
ggggacccgc ggguuugcua uggcgaugag cagcggcggc aguggguggcg gcgucccgga      60 gcaggaggau uccgugcugu uccggcgcgg cacaggccaa agcgaugauu cugacauuug     120
ggaugauaca gcacugauaa aagcauauga uaaagcugug gcuucauuua agcaugcucu     180
aaagaauggu gacauuugug aaacuucggg uaaaccaaaa accacaccua aaagaaaacc     240
ugcuaagaag aauaaaagcc aaaagaagaa uacugcagcu uccuuacaac aguggaaagu     300
uggggacaaa uguucugcca uuuggucaga agacgguugc auuuacccag cuaccauugc     360
uucaauugau uuuaagagag aaaccugugu ugugguuuac acuggauaug gaaauagaga     420
```

```
ggagcaaaau cugaccgauc uacuuucccc aaucugugaa guagcuaaua auauagaaca    480
aaaugcucaa gagaaugaaa augaaagcca aguuucaaca gaugaaagug agaacuccag    540
gucuccugga aauaaaucag auaacaucaa gcccaaaucu gcuccaugga acucuuuucu    600
cccuccacca cccccaugc cagggccaag acugggacca ggaaagccag gucuaaaauu     660
caauggccca ccaccgccac cgccaccacc accaccccac uuacuaucau gcuggcugcc    720
uccauuccu ucuggaccac caauaauucc cccaccaccu cccauaugac cagauucucu     780
ugaugaugcu gaugcuuugg gaaguauguu aauuucaugg uacaugagug gcaucauac     840
uggcuauuau auggguuuca gacaaaauca aaaagaagga aggugcucac auuccuaaaa    900
uuaaggagaa augcuggcau agagcagcac uaaaugacac cacuaaagaa acgaucagac    960
agaucuggaa ugugaagcgu auagaagau aacuggccuc auucuucaa aauaucaagu      1020
guugggaaag aaaaaaggaa guggaauggg uaacucuucu ugauuaaaag uuauguaaua    1080
accaaaugca augugaaaua uuuuacugga cucuauuuug aaaaaccauc uguaaaagac    1140
uggggugggg gugggaggcc agcacggugg ugaggcaguu gagaaaauuu gaaugguggau 1200
uagauuuuga augauauugg auaauuauug guaauuuuua ugagcuguga aagggguguu   1260
guaguuuaua aaagacuguc uuaauuugca uacuuaagca uuuaggaaug aaguguuaga    1320
gugucuaaaa auguucaaa ugguuuaaca aaauguaugu gaggcguaug uggcaaaaug     1380
uuacagaauc uaacugguug acauggcugu ucauuguacu guuuuuucu aucuucuaua     1440
uguuaaaaag uauauaauaa aaauauuuaa uuuuuuuuua aaaaaaaaa aaaaaaaaca     1500
aaaaaaaaaa a                                                        1511
```

<210> SEQ ID NO 2
<211> LENGTH: 294
<212> TYPE: PRT
<213> ORGANISM: Homo sapiens

<400> SEQUENCE: 2

```
Met Ala Met Ser Ser Gly Gly Ser Gly Gly Gly Val Pro Glu Gln Glu
1               5                   10                  15

Asp Ser Val Leu Phe Arg Arg Gly Thr Gly Gln Ser Asp Asp Ser Asp
            20                  25                  30

Ile Trp Asp Asp Thr Ala Leu Ile Lys Ala Tyr Asp Lys Ala Val Ala
        35                  40                  45

Ser Phe Lys His Ala Leu Lys Asn Gly Asp Ile Cys Glu Thr Ser Gly
    50                  55                  60

Lys Pro Lys Thr Thr Pro Lys Arg Lys Pro Ala Lys Lys Asn Lys Ser
65                  70                  75                  80

Gln Lys Lys Asn Thr Ala Ala Ser Leu Gln Gln Trp Lys Val Gly Asp
                85                  90                  95

Lys Cys Ser Ala Ile Trp Ser Glu Asp Gly Cys Ile Tyr Pro Ala Thr
            100                 105                 110

Ile Ala Ser Ile Asp Phe Lys Arg Glu Thr Cys Val Val Val Tyr Thr
        115                 120                 125

Gly Tyr Gly Asn Arg Glu Glu Gln Asn Leu Ser Asp Leu Leu Ser Pro
    130                 135                 140

Ile Cys Glu Val Ala Asn Asn Ile Glu Gln Asn Ala Gln Glu Asn Glu
145                 150                 155                 160

Asn Glu Ser Gln Val Ser Thr Asp Glu Ser Glu Asn Ser Arg Ser Pro
                165                 170                 175
```

```
Gly Asn Lys Ser Asp Asn Ile Lys Pro Lys Ser Ala Pro Trp Asn Ser
            180                 185                 190

Phe Leu Pro Pro Pro Pro Met Pro Gly Pro Arg Leu Gly Pro Gly
        195                 200                 205

Lys Pro Gly Leu Lys Phe Asn Gly Pro Pro Pro Pro Pro Pro Pro
210                 215                 220

Pro Pro His Leu Leu Ser Cys Trp Leu Pro Pro Phe Pro Ser Gly Pro
225                 230                 235                 240

Pro Ile Ile Pro Pro Pro Pro Ile Cys Pro Asp Ser Leu Asp Asp
            245                 250                 255

Ala Asp Ala Leu Gly Ser Met Leu Ile Ser Trp Tyr Met Ser Gly Tyr
            260                 265                 270

His Thr Gly Tyr Tyr Met Gly Phe Arg Gln Asn Gln Lys Glu Gly Arg
            275                 280                 285

Cys Ser His Ser Leu Asn
            290

<210> SEQ ID NO 3
<211> LENGTH: 885
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 3
auggccauga gcagcggagg cagcggcgga ggagugcccg agcaggagga cagcgugcug      60
uucaggagag gcaccggcca gagcgaugac agcgauaucu gggacgauac cgcucugauc     120
aaggccuacg acaaggccgu ggccagcuuc agcacgccc ugaaaaacgg cgacaucugc     180
gagaccagcg gcaagcccaa gacaaccccc aagagaaagc ccgccaagaa gaauaagagc     240
cagaaaaaga caccgccgc cagccugcag caguggaagg ugggcgacaa gugcagcgcc     300
aucuggagcg aggacggcug caucuacccc gccaccaucg ccagcaucga cuucaagaga     360
gagaccugcg uggucgugua caccggcuac ggcaacagag aggagcagaa ccugagcgac     420
cugcugagcc ccauuuguga gguggccaau aacaucgaac agaacgccca ggagaacgag     480
aaugaaagcc aggugagcac cgacgagagc gagaacagca gaucuccugg caacaagagc     540
gacaacauca agccuaaguc ugccccuugg aacagcuucc ugccccucc uccacccaug     600 cccggaccca dacugggacc cggaaaaaccu ggccugaagu caacggacc accuccccu      660 ccaccuccuc ccccaccuca ucuccugagc ugcuggcugc cacccuuccc cagcggaccc     720
ccuaucaucc caccacccc ucccaucugc ccgacagcc uggacgacgc cgaugcccug     780
ggcagcaugc ugaucagcug guacaugagc ggcuaccaca caggauacua caugggcuuc     840
agacagaacc agaaggaggg cagaugcucc cacuccuga acuga                     885

<210> SEQ ID NO 4
<211> LENGTH: 885
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 4
auggccauga gcagcggagg aagcggagga ggagugccag aacaggaaga uagcgugcug      60
```

| | |
|---|---|
| uuucgccggg gcaccggaca aucggacgac agcgauauuu gggacgacac ugcgcucauc | 120 |
| aaggccuacg acaaggcggu ggcuucguuc aagcacgcuc ugaagaacgg ggauaucugu | 180 |
| gaaaccagcg guaaaccaaa aacuacgccg aaaaggaaac ccgccaaaaa gaacaaguca | 240 |
| cagaagaaga auaccgcugc gagcuugcag caguggaagg ugggcgacaa gugcuccgcg | 300 |
| auuuggucgg aagaugguug caucuacccg gcaaccaucg ccuccaucga cuuuaagcgg | 360 |
| gagacuugcg ucguggucua caccggauac ggcaauagag aggaacagaa ucugucagac | 420 |
| cuucugucgc caaucugcga ggucgccaac aauaucgaac aaaacgccca agagaacgag | 480 |
| aaugagcccc aaguguccac ggacgaaucg gaaaacucac ggucccugg aacaaguca | 540 |
| gauaacauca agccuaaauc ggcaccaugg aacuccuucc ugccgccucc gccuccgaug | 600 |
| ccgggcccgc gccugggacc ggguaaaccc gggcucaagu caauggacc gccacccca | 660 |
| cccccgccac cgccgcccca ccuccucucg ugcuggcugc cgccguuccc uuccggaccg | 720 |
| ccuaucauuc cgccaccucc accaucugcc ccagacagcc uggaugaugc cgacgcauug | 780 |
| ggcuccaugc ucaucucaug guacaugucg ggauaccaua cugggauuua caugggcuuc | 840 |
| agacagaacc agaaggaagg acgcuguucc cauagccuga acuag | 885 |

<210> SEQ ID NO 5
<211> LENGTH: 1442
<212> TYPE: RNA
<213> ORGANISM: Homo sapiens

<400> SEQUENCE: 5

| | |
|---|---|
| ggggccccac gcugcgcacc cgcggguuug cuauggcgau gagcagcggc ggcaguggug | 60 |
| gcggcguccc ggagcaggag gauuccgugc uguuccggcg cggcacaggc cagagcgaug | 120 |
| auucugacau uugggaugau acagcacuga uaaaagcaua ugauaaagcu guggcuucau | 180 |
| uuaagcaugc ucuaaagaau ggugacauuu gugaaacuuc ggguaaacca aaaaccacac | 240 |
| cuaaaagaaa accugcuaag aagaauaaaa gccaaagaa gaauacugca gcuuccuuac | 300 |
| aacaguggaa aguuggggac aaauguucug ccauuggguc agaagacggu ugcauuuacc | 360 |
| cagcuaccau ugcuucaauu gauuuuaaga gagaaaccug uguugugguu uacacuggau | 420 |
| auggaaauag agaggagcaa aaucuguccg aucuacuuuc cccaaucugu gaaguagcua | 480 |
| auaauauaga acagaaugcu caagagaaug aaaaugaaag ccaaguuuca acagaugaaa | 540 |
| gugagaacuc caggucuccu ggaaauaaau cagauaacau caagcccaaa ucugcuccau | 600 |
| ggaacucuuu ucucccucca ccaccccca ugcaggggcc aagacuggga ccaggaaagc | 660 |
| caggucuaaa auucaauggc ccaccaccgc caccgccacc accaccaccc cacuuacuau | 720 |
| caugcuggcu gccuccauuu ccuucuggac caccauaauu ccccacca ccucccauau | 780 |
| guccagauuc ucuugaugau gcugaugcuu ugggaaguau guuaauuuca ugguacauga | 840 |
| guggcuauca uacuggcuau uauauggaaa ugcuggcaua gagcagcacu aaaugacacc | 900 |
| acuaaagaaa cgaucagaca gaucuggaau gugaagcguu auagaagaua acuggccuca | 960 |
| uuucuucaaa auaucaagug uugggaaaga aaaaggaag uggaaugggu aacucuucuu | 1020 |
| gauuaaaagu uauguaauaa ccaaaugcaa ugugaaauau uuacuggac ucuauuuuga | 1080 |
| aaaaccaucu guaaaagacu gaggugggg ugggaggcca gcacgguggu gaggcaguug | 1140 |
| agaaauuuug aaugggauu agauuuugaa ugauauugga uaauauugg uaauuuuaug | 1200 |
| agcugugaga agggguuugu aguuuauaaa agacugcucu aauuugcaua cuuaagcauu | 1260 |
| uaggaaugaa guguuagagu gucuuaaaau guuucaaaug guuuaacaaa auguaugua | 1320 |

```
ggcguaugug gcaaaauguu acagaaucua acuggggac auggcuguuc auuguacugu    1380
uuuuuucuau cuucuauaug uuuaaaagua uauaauaaaa auauuuaauu uuuuuuuaaa    1440
aa                                                                   1442
```

<210> SEQ ID NO 6
<211> LENGTH: 282
<212> TYPE: PRT
<213> ORGANISM: Homo sapiens

<400> SEQUENCE: 6

```
Met Ala Met Ser Ser Gly Gly Ser Gly Gly Gly Val Pro Glu Gln Glu
1               5                   10                  15

Asp Ser Val Leu Phe Arg Arg Gly Thr Gly Gln Ser Asp Asp Ser Asp
            20                  25                  30

Ile Trp Asp Asp Thr Ala Leu Ile Lys Ala Tyr Asp Lys Ala Val Ala
        35                  40                  45

Ser Phe Lys His Ala Leu Lys Asn Gly Asp Ile Cys Glu Thr Ser Gly
    50                  55                  60

Lys Pro Lys Thr Thr Pro Lys Arg Lys Pro Ala Lys Lys Asn Lys Ser
65                  70                  75                  80

Gln Lys Lys Asn Thr Ala Ala Ser Leu Gln Gln Trp Lys Val Gly Asp
                85                  90                  95

Lys Cys Ser Ala Ile Trp Ser Glu Asp Gly Cys Ile Tyr Pro Ala Thr
            100                 105                 110

Ile Ala Ser Ile Asp Phe Lys Arg Glu Thr Cys Val Val Val Tyr Thr
        115                 120                 125

Gly Tyr Gly Asn Arg Glu Glu Gln Asn Leu Ser Asp Leu Leu Ser Pro
    130                 135                 140

Ile Cys Glu Val Ala Asn Asn Ile Glu Gln Asn Ala Gln Glu Asn Glu
145                 150                 155                 160

Asn Glu Ser Gln Val Ser Thr Asp Glu Ser Asn Ser Arg Ser Pro
                165                 170                 175

Gly Asn Lys Ser Asp Asn Ile Lys Pro Lys Ser Ala Pro Trp Asn Ser
            180                 185                 190

Phe Leu Pro Pro Pro Pro Met Pro Gly Pro Arg Leu Gly Pro Gly
        195                 200                 205

Lys Pro Gly Leu Lys Phe Asn Gly Pro Pro Pro Pro Pro Pro
    210                 215                 220

Pro Pro His Leu Leu Ser Cys Trp Leu Pro Pro Phe Pro Ser Gly Pro
225                 230                 235                 240

Pro Ile Ile Pro Pro Pro Pro Ile Cys Pro Asp Ser Leu Asp Asp
                245                 250                 255

Ala Asp Ala Leu Gly Ser Met Leu Ile Ser Trp Tyr Met Ser Gly Tyr
            260                 265                 270

His Thr Gly Tyr Tyr Met Glu Met Leu Ala
        275                 280
```

<210> SEQ ID NO 7
<211> LENGTH: 140
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 7

| | |
|---|---|
| ggacagaucg ccuggagacg ccauccacgc uguuuugacc uccauagaag acaccgggac | 60 |
| cgauccagcc uccgcggccg ggaacggugc auuggaacgc ggauuccccg ugccaagagu | 120 |
| gacucaccgu ccuugacacg | 140 |

<210> SEQ ID NO 8
<211> LENGTH: 105
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 8

| | |
|---|---|
| cggguggcau cccugugacc ccucccccagu gccucuccug gcccuggaag uugccacucc | 60 |
| agugcccacc agccuugucc uaauaaaauu aaguugcauc aagcu | 105 |

<210> SEQ ID NO 9
<211> LENGTH: 105
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 9

| | |
|---|---|
| ggguggcauc ccugugaccc cuccccagug ccucuccugg cccuggaagu ugccacucca | 60 |
| gugcccacca gccuuguccu aauaaaauua aguugcauca aagcu | 105 |

<210> SEQ ID NO 10
<211> LENGTH: 1130
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 10

| | |
|---|---|
| ggacagaucg ccuggagacg ccauccacgc uguuuugacc uccauagaag acaccgggac | 60 |
| cgauccagcc uccgcggccg ggaacggugc auuggaacgc ggauuccccg ugccaagagu | 120 |
| gacucaccgu ccuugacacg auggccauga gcagcgagg cagcggcgga ggagugcccg | 180 |
| agcaggagga cagcgugcug uucaggagag gcaccggcca gagcgaugac agcgauaucu | 240 |
| gggacgauac cgcucugauc aaggccuaca caaggccgu ggccagcuuc aagcacgccc | 300 |
| ugaaaacgg cgacaucugc gagaccagcg gcaagcccaa gacaaccccc aagagaaagc | 360 |
| ccgccaagaa gaauaagagc cagaaaaaga caccgccgc cagccugcag caguggaagg | 420 |
| ugggcgacaa gugcagcgcc aucuggagcg aggacggcug caucuacccc gccaccaucg | 480 |
| ccagcaucga cuucaagaga gagaccgccg uggucguguua caccggcuac ggcaacagag | 540 |
| aggagcagaa ccugagcgac cugcugagcc ccauuuguga ggguggccaau aacaucgaac | 600 |
| agaacgccca ggagaacgag aaugaaagcc aggugagcac cgacgagagc gagaacagca | 660 |
| gaucuccugg caacaagagc gacaacauca agcuaaguc ugccccuugg aacagcuucc | 720 |
| ugcccccucc uccacccaug cccggaccca gacugggacc cggaaaaccu ggccugaagu | 780 |
| ucaacggacc accucccccu ccaccuccuc cccaccuca ucuccugagc ugcuggcugc | 840 |
| cacccuuccc cagcggaccc ccuaucaucc caccaccccc ucccaucugc cccgacagcc | 900 |
| uggacgacgc cgaugcccug ggcagcaugc ugaucagcug guacauagc ggcuaccaca | 960 |

```
caggauacua caugggcuuc agacagaacc agaaggaggg cagaugcucc cacucccuga    1020
acugacgggu ggcaucccug ugaccccucc ccagugccuc uccuggcccu ggaaguugcc    1080
acuccagugc ccaccagccu uguccuaaua aauuaaguu gcaucaagcu                1130
```

<210> SEQ ID NO 11
<211> LENGTH: 1130
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 11

```
ggacagaucg ccuggagacg ccauccacgc uguuuugacc uccauagaag acaccgggac    60
cgauccagcc uccgcggccg ggaacggugc auuggaacgc ggauccccg ugccaagagu     120 gacucaccgu ccuugacacg auggccauga gcagcggagg cagcggcgga ggagugcccg    180
agcaggagga cagcgugcug uucaggagag gcaccggcca gagcgaugac agcgauaucu    240
gggacgauac cgcucugauc aaggccuacg acaaggccgu ggccagcuuc aagcacgccc    300
ugaaaaacgg cgacaucugc gagaccagcg gcaagcccaa gacaaccccc aagagaaagc    360
ccgccaagaa gaauaagagc cagaaaaaga cacccgccgc cagccugcag caguggaagg    420
ugggcgacaa gugcagcgcc aucuggacg aggacggcug caucuacccc gccaccaucg     480
ccagcaucga cuucaagaga gagaccugcg uggucguga caccggcuac ggcaacagag    540
aggagcagaa ccugagcgac cugcugagcc cauuuguga gguggccaau aacaucgaac    600
agaacgccca ggagaacgag aaugaaagcc aggugagcac cgacgagagc gagaacagca    660
gauccccugg caacaagagc gacaacauca agccuaaguc ugccccuugg aacagcuucc    720 ugccccccucc uccacccaug cccggaccca gacugggacc cggaaaaccu ggccugaagu    780
ucaacggacc accuccccu ccaccuccuc cccaccuca ucuccugagc ugcuggcugc      840 caccuuccc cagcggaccc ccuaucaucc caccacccc ucccaucugc ccgacagcc      900 uggacgacgc cgaugcccug ggcagcaugc ugaucagcug guacaugagc ggcuaccaca    960
caggauacua caugggcuuc agacagaacc agaaggaggg cagaugcucc cacucccuga    1020
acugagggug gcaucccugu gaccccuccc cagugccucu ccuggcccug gaaguugcca    1080
cuccagugcc caccagccuu guccuaauaa aauuaaguug caucaaagcu                1130
```

<210> SEQ ID NO 12
<211> LENGTH: 500
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(500)
<223> OTHER INFORMATION: This sequence may encompass 10-500 nucleotides
<220> FEATURE:
<223> OTHER INFORMATION: See specification as filed for detailed
      description of substitutions and preferred embodiments

<400> SEQUENCE: 12

```
aaaaaaaaaa aaaaaaaaaa aaaaaaaaaa aaaaaaaaaa aaaaaaaaaa aaaaaaaaaa    60
aaaaaaaaaa aaaaaaaaaa aaaaaaaaaa aaaaaaaaaa aaaaaaaaaa aaaaaaaaaa    120
aaaaaaaaaa aaaaaaaaaa aaaaaaaaaa aaaaaaaaaa aaaaaaaaaa aaaaaaaaaa    180
```
aaaaaaaaaa aaaaaaaaaa aaaaaaaaaa aaaaaaaaaa aaaaaaaaaa aaaaaaaaaa        240
aaaaaaaaaa aaaaaaaaaa aaaaaaaaaa aaaaaaaaaa aaaaaaaaaa aaaaaaaaaa        300
aaaaaaaaaa aaaaaaaaaa aaaaaaaaaa aaaaaaaaaa aaaaaaaaaa aaaaaaaaaa        360
aaaaaaaaaa aaaaaaaaaa aaaaaaaaaa aaaaaaaaaa aaaaaaaaaa aaaaaaaaaa        420
aaaaaaaaaa aaaaaaaaaa aaaaaaaaaa aaaaaaaaaa aaaaaaaaaa aaaaaaaaaa        480
aaaaaaaaaa aaaaaaaaaa                                                    500

<210> SEQ ID NO 13
<211> LENGTH: 300
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(300)
<223> OTHER INFORMATION: This sequence may encompass 10-300 nucleotides
<220> FEATURE:
<223> OTHER INFORMATION: See specification as filed for detailed
      description of substitutions and preferred embodiments

<400> SEQUENCE: 13
aaaaaaaaaa aaaaaaaaaa aaaaaaaaaa aaaaaaaaaa aaaaaaaaaa aaaaaaaaaa         60
aaaaaaaaaa aaaaaaaaaa aaaaaaaaaa aaaaaaaaaa aaaaaaaaaa aaaaaaaaaa        120
aaaaaaaaaa aaaaaaaaaa aaaaaaaaaa aaaaaaaaaa aaaaaaaaaa aaaaaaaaaa        180
aaaaaaaaaa aaaaaaaaaa aaaaaaaaaa aaaaaaaaaa aaaaaaaaaa aaaaaaaaaa        240
aaaaaaaaaa aaaaaaaaaa aaaaaaaaaa aaaaaaaaaa aaaaaaaaaa aaaaaaaaaa        300

<210> SEQ ID NO 14
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(200)
<223> OTHER INFORMATION: This sequence may encompass 10-200 nucleotides
<220> FEATURE:
<223> OTHER INFORMATION: See specification as filed for detailed
      description of substitutions and preferred embodiments

<400> SEQUENCE: 14
cccccccccc cccccccccc cccccccccc cccccccccc cccccccccc cccccccccc         60
cccccccccc cccccccccc cccccccccc cccccccccc cccccccccc cccccccccc        120
cccccccccc cccccccccc cccccccccc cccccccccc cccccccccc cccccccccc        180
cccccccccc cccccccccc                                                    200

<210> SEQ ID NO 15
<211> LENGTH: 250
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: See specification as filed for detailed
      description of substitutions and preferred embodiments

```
<400> SEQUENCE: 15
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180
aaaaaaaaaa aaaaaaaaaa aaaaaaaaaa aaaaaaaaaa aaaaaaaaaa aaaaaaaaaa     240
aaaaaaaaaa                                                            250
```